US008222188B2

(12) United States Patent
Bremel et al.

(10) Patent No.: US 8,222,188 B2
(45) Date of Patent: Jul. 17, 2012

(54) ANTIBODY LIBRARIES

(75) Inventors: Robert D. Bremel, Hillpoint, WI (US);
Kurt Eakle, Prairie du Sac, WI (US);
Michael Imboden, Madison, WI (US)

(73) Assignee: Catalent Pharma Solutions, LLC, Somerset, NJ (US)

( * ) Notice: Subject to any disclaimer, the term of this patent is extended or adjusted under 35 U.S.C. 154(b) by 0 days.

(21) Appl. No.: 12/493,851

(22) Filed: Jun. 29, 2009

(65) Prior Publication Data
US 2010/0009869 A1    Jan. 14, 2010

Related U.S. Application Data

(63) Continuation of application No. 10/401,000, filed on Mar. 27, 2003, now abandoned.

(60) Provisional application No. 60/368,808, filed on Mar. 28, 2002, provisional application No. 60/371,299, filed on Apr. 10, 2002.

(51) Int. Cl.
C40B 40/02    (2006.01)
C12Q 1/70    (2006.01)

(52) U.S. Cl. ............................................. 506/14; 435/5
(58) Field of Classification Search ............... 506/14; 435/5
See application file for complete search history.

(56) References Cited

U.S. PATENT DOCUMENTS

| 4,560,655 A | 12/1985 | Baker |
| 4,657,866 A | 4/1987 | Kumar |
| 4,677,066 A | 6/1987 | Takahashi et al. |
| 4,743,548 A | 5/1988 | Crossway et al. |
| 4,767,704 A | 8/1988 | Cleveland et al. |
| 4,816,567 A | 3/1989 | Cabilly et al. |
| 4,927,762 A | 5/1990 | Darfler |
| 4,937,190 A | 6/1990 | Palmenberg et al. |
| 4,946,778 A * | 8/1990 | Ladner et al. ............... 435/69.6 |
| 5,122,469 A | 6/1992 | Mather et al. |
| 5,139,941 A | 8/1992 | Muzyczka et al. |
| 5,149,645 A | 9/1992 | Hoekema et al. |
| 5,168,062 A | 12/1992 | Stinski |
| 5,173,414 A | 12/1992 | Lebkowski et al. |
| 5,215,904 A | 6/1993 | Gould et al. |
| 5,225,347 A | 7/1993 | Goldberg et al. |
| 5,385,839 A | 1/1995 | Stinski |
| 5,508,184 A | 4/1996 | Negrutiu et al. |
| 5,512,421 A | 4/1996 | Burns et al. |
| 5,512,443 A | 4/1996 | Schlom et al. |
| 5,591,624 A | 1/1997 | Barber et al. |
| 5,618,682 A | 4/1997 | Scheirer |
| 5,627,058 A | 5/1997 | Ruley et al. |
| 5,670,113 A | 9/1997 | Akong et al. |
| 5,674,713 A | 10/1997 | McElroy et al. |
| 5,686,120 A | 11/1997 | Mertz et al. |
| 5,686,279 A | 11/1997 | Finer et al. |
| 5,716,832 A | 2/1998 | Barber et al. |
| 5,719,055 A | 2/1998 | Cooper |
| 5,721,121 A | 2/1998 | Etcheverry et al. |
| 5,780,225 A * | 7/1998 | Wigler et al. ............... 435/6 |
| 5,807,689 A | 9/1998 | Daggett et al. |
| 5,817,491 A | 10/1998 | Yee et al. |
| 5,834,256 A | 11/1998 | Finer et al. |
| 5,843,742 A | 12/1998 | Natsoulis et al. |
| 5,850,000 A | 12/1998 | Bleck et al. |
| 5,858,740 A | 1/1999 | Finer et al. |
| 5,866,400 A | 2/1999 | Palsson et al. |
| 5,874,540 A | 2/1999 | Hensen et al. |
| 5,876,946 A | 3/1999 | Burbaum et al. |
| 5,892,019 A | 4/1999 | Schlom et al. |
| 5,914,267 A | 6/1999 | Mertz et al. |
| 5,922,601 A | 7/1999 | Baetscher et al. |
| 5,948,675 A | 9/1999 | Klatzmann et al. |
| 5,952,212 A | 9/1999 | Moller et al. |
| 5,955,592 A | 9/1999 | Ullrich et al. |
| 5,958,719 A | 9/1999 | Ullrich et al. |
| 5,958,775 A | 9/1999 | Wickstrom et al. |
| 5,965,443 A | 10/1999 | Reznikoff et al. |
| 5,968,785 A | 10/1999 | Devine et al. |
| 5,976,796 A | 11/1999 | Szalay et al. |
| 5,976,852 A | 11/1999 | Cheng et al. |
| 5,976,853 A | 11/1999 | Guthridge et al. |
| 5,981,251 A | 11/1999 | Ullrich et al. |
| 5,993,813 A | 11/1999 | Mezes et al. |
| 5,994,074 A | 11/1999 | Beach et al. |
| 5,994,136 A | 11/1999 | Naldini et al. |
| 6,004,791 A | 12/1999 | Aoki et al. |
| 6,013,455 A | 1/2000 | Bandman et al. |
| 6,013,464 A | 1/2000 | Abo et al. |
| 6,013,516 A | 1/2000 | Verma et al. |
| 6,015,807 A | 1/2000 | Engel et al. |
| 6,020,306 A | 2/2000 | Boyd et al. |
| 6,025,192 A | 2/2000 | Beach et al. |
| 6,027,722 A | 2/2000 | Hodgson |
| 6,027,875 A | 2/2000 | Weinberger |
| 6,030,788 A | 2/2000 | Gerhold |
| 6,030,822 A | 2/2000 | Lechner et al. |
| 6,034,228 A | 3/2000 | Norris et al. |
| 6,051,427 A | 4/2000 | Finer et al. |
| 6,061,427 A | 5/2000 | Ryoo |

(Continued)

FOREIGN PATENT DOCUMENTS

EP    117058    1/1984

(Continued)

OTHER PUBLICATIONS

Buchschacher, 2001, Introduction to Retroviruses and Retroviral Vectors, Somatic Cell and Molecular Genetics, 26: 1-11.*

(Continued)

Primary Examiner — Amber D Steele
(74) Attorney, Agent, or Firm — Casimir Jones S.C.

(57) ABSTRACT

The present invention relates to the production of antibody libraries. In particular, the present invention relates to the use of integrating retroviral vectors to generate libraries comprising a plurality of combinations of antibody light chains and heavy chains. The present invention thus provides improved methods of generating and screening antibody libraries comprising large numbers of unique antibodies.

1 Claim, 56 Drawing Sheets

U.S. PATENT DOCUMENTS

| | | | |
|---|---|---|---|
| 6,074,859 | A | 6/2000 | Hirokawa et al. |
| 6,080,912 | A | 6/2000 | Bremel et al. |
| 6,136,597 | A | 10/2000 | Hope et al. |
| 6,187,287 | B1 | 2/2001 | Leung et al. |
| 6,255,071 | B1 | 7/2001 | Beach et al. |
| 6,291,740 | B1 | 9/2001 | Bremel et al. |
| 6,319,707 | B1 | 11/2001 | Adam et al. |
| 6,331,415 | B1 | 12/2001 | Cabilly et al. |
| 6,333,195 | B1 | 12/2001 | Respess et al. |
| 6,368,862 | B1 | 4/2002 | Palmer et al. |
| 6,410,316 | B1 | 6/2002 | Sheridan et al. |
| 6,852,510 | B2 * | 2/2005 | Bremel et al. ............... 435/69.1 |
| 7,393,632 | B2 * | 7/2008 | Cheo et al. ........................ 435/6 |
| 2001/0018203 | A1 | 8/2001 | Iba et al. |
| 2001/0034393 | A1 | 10/2001 | Wang et al. |
| 2001/0043921 | A1 | 11/2001 | Gunzburg et al. |
| 2002/0007051 | A1 * | 1/2002 | Cheo et al. .................. 536/23.1 |

FOREIGN PATENT DOCUMENTS

| | | |
|---|---|---|
| WO | 87/00195 | 1/1987 |
| WO | 90/03430 | 4/1990 |
| WO | 92/01070 | 1/1992 |
| WO | 93/02108 | 2/1993 |
| WO | 93/03143 | 2/1993 |
| WO | 93/03769 | 3/1993 |
| WO | 94/05786 | 3/1994 |
| WO | 94/24870 | 11/1994 |
| WO | 96/11013 | 4/1996 |
| WO | 99/14310 | 3/1999 |
| WO | 99/43795 | 9/1999 |

OTHER PUBLICATIONS

Markowitz et al., 1988, "A safe packaging line for gene transfer: separating viral genes on two different plasmids". J. Virol. 62(4):1120-1124.

Martial et al., 1979, "Human growth hormone: complementary DNA cloning and expression in bacteria". Science. 205(4406): 602-607.

Masters et al., 1989, "Structure and Expression of the Glycoprotein Gene of Chandipura Virus", Virology 171:285-290.

Mastromarino et al., 1987, "Characterization of Membrane Components of the Erythrocyte Involved in Vesicular Stomatitis Virus Attachment and Fusion at Acidic pH", J. Gen. Virol. 68:2359-2369.

Mather et al., 1982, "Culture of testicular cells in hormone-supplemented serum-free medium". Annals N.Y. Acad. Sci., 383:44 68.

Mather, 1980, "Establishment and characterization of two distinct mouse testicular epithelial cell lines". Biol. Reprod. 23(1):243 252.

Mathor et al., 1996, "Clonal analysis of stably transduced human epidermal stem cells in culture". PNAS 93 (19):10371-10376.

McBurney et al., 1994, "Unstable integration of transfected DNAs into embryonal carcinoma cells". Somatic Cell Molec. Genet. 20(6):529-40.

Mebatsion et al., 1995, "Mokola virus glycoprotein and chimeric proteins can replace rabies virus glycoprotein in the rescue of infectious defective rabies virus particles". J. Virol. 69(3):1444-1451.

Mehtali et al., 1990, "The methylation-free status of a housekeeping transgene is lost at high copy number". Gene 91(2):179-84.

Meyer et al., 1995, "Interaction of eukaryotic initiation factor eIF-4B with a picornavirus internal translation initiation site". J. Virol. 69 (5): 2819 2824.

Mielke et al., 1996, "Anatomy of highly expressing chromosomal sites targeted by retroviral vectors". Biochem. 35 (7):2239-2252.

Miller and Buttimore, 1986, "Redesign of retrovirus packaging cell lines to avoid recombination leading to helper virus production". Mol. Cell. Biol. 6(8):2895.

Miller et al., 1990, "Gene transfer by retrovirus vectors occurs only in cells that are actively replicating at the time of infection". Mol. Cell. Biol. 10(8):4239-4242.

Miller, 1990, "Human gene therapy comes of age", Nature 357: 455-460.

Mizushima and Nagata, 1990, "pEF-BOS, a powerful mammalian expression vector". Nuc. Acids. Res., 18 (17):5322.

Morisato and Kleckner, 1987, "Tn10 transposition and circle formation in vitro". Cell 51(1):101-111.

Muzyczka, 1992, "Use of adeno-associated virus as a general transduction vector for mammalian cells".Current Topics in Microbiol. and Immunol. 158:97-129.

Naldini et al., 1996, "In vivo gene delivery and stable transduction of nondividing cells by a lentiviral vector".Science 272(5259):263-267.

Neer, 1995, "Heterotrimeric G proteins: organizers of transmembrane signals". Cell. 80(2):249 257.

O'Gorman et al., 1991, "Recombinase-mediated gene activation and site-specific integration in mammalian cells". Science 251(4999):1351-1355.

Potrykus and Shillito, 1986, Methods in Enzymology, vol. 118, Plant Molecular Biology, A. and H. Weissbach eds., Academic Press, Orlando.

Poul et al., 1995, "Design of cassette baculovirus vectors for the production of therapeutic antibodies in insect cells". Immunotechnology, 1(3-4):189-196.

Quade, 1979, "Transformation of mammalian cells by avian myelocytomatosis virus and avian erythroblastosis virus". Virol. 98(2):461-465.

Roe et al., 1993, "Integration of murine leukemia virus DNA depends on mitosis". EMBO J. 12(5):2099-2108.

Rogers et al.,2000, "Versatile Reporter Vectors for Monitoring Viral Transduction", Strategies Newsletter, 13:97-99.

Saito et al., 1991, "Molecular Characterization of Protein Tyrosine Phosphatases", Cell Growth and Diff. 2:59 65.

Sambrook et al., 1989, Molecular Cloning: A Laboratory Manual, 2nd ed., Cold Spring Harbor Laboratory Press, New York pp. 16.7-16.15.

Scheper et al., 1994, "Binding of eukaryotic initiation factor-2 and trans-acting factors to the 5' untranslated region of encephalomyocarditis virus RNA", Biochimie, 76: 801 809.

Schroder and Friedl, 1997, "Overexpression of recombinant human antithrombin III in Chinese hamster ovary cells results in malformation and decreased secretion of recombinant protein". Biotech. Bioeng. 53(6):547-559.

Schroeder and Neagle, 1996, "FLIPR: A New Instrument for Accurate, High Throughput Optical Screening", J. Biomol. Screening 1:75-80.

Shelling and Smith, 1994, "Targeted integration of transfected and infected adeno-associated virus vectors containing the neomycin resistance gene". Gene Therapy 1(3):165-169.

Sternweis and Smrcka, 1992, "Regulation of phospholipase C by G proteins". Trends in Biochem. Sci. 17(12):502 506.

Uetsuki et al., 1989, "Isolation and characterization the human chromosomal gene for polypeptide chain elongation factor-1 alpha". J. Biol. Chem., 264(10):5791-5798.

Uhlmann et al., 1990, "Antisense Oligonucleotides: A New Therapeutic Principle", Chem. Rev. 90(4):543-584.

Ullrich and Schlessinger, 1990, "Signal transduction by receptors with tyrosine kinase activity". Cell 61(2):203 212.

Vaillancourt et al.,2000, "Safe Production of High-Titer Retrovirus", Strategies Newsletter 13:50-53.

Van Deursen et al., 1995, "Cre-mediated site-specific translocation between nonhomologous mouse chromosomes". Proc. Natl. Acad. Sci. USA 92:7376-7380.

Vincent et al., 1990, "Replication and packaging of HIV envelop0e genes in a novel adeno-associated virus vector system"; Vaccines 90: Mod. Approaches New Vaccines Incl. Prev. AIDS; 7: 353-9.

Von Ruden et al., 1995, "Generation of high-titer retroviral vectors following receptor-mediated, adenovirus-augmented transfection". Bio Techniques 18(3):484-489.

Voss et al., 1986, "The role of enhancers in the regulation of cell-type-specific transcriptional control", Trends Biochem. Sci., 11:287.

Wang et al., 1996, "Development of a VSV-G protein pseudotyped retroviral vector system expressing dominant oncogenes from a lacO-modified inducible LTR promoter". Gene 182(1-2):145-150.

Weidle et al., 1988, "Amplified expression constructs for human tissue-type plasminogen activator in Chinese hamster ovary cells: instability in the absence of selective pressure". Gene 66(2):193-203.

Wilson et al., 1984, "The structure of an antigenic determinant in a protein". Cell, 37(3):767-778.

Yee et al., 1994, "Generation of high-titer pseudotyped retroviral vectors with very broad host range". Meth. Cell Biol. 43 Pt A:99-112.

Zhou et al., 1994, "Adeno-associated virus 2-mediated high efficiency gene transfer into immature and mature subsets of hematopoietic progenitor cells in human umbilical cord blood". J. Exp. Med. 179(6):1867-1875.

Zufferey et al., 1999, "Woodchuck hepatitis virus posttranscriptional regulatory element enhances expression of transgenes delivered by retroviral vectors". J. Virol. 73(4):2886-2892.

Zwizinski et al., 1980, "Purification and characterization of leader (signal) peptidase from *Escherichia coli*". J. Biol. Chem. 255(16): 7973-7977.

Adams et al., 1992, "Transduction of primary human hepatocytes with amphotropic and xenotropic retroviral vectors", Proc. Natl. Acad. Sci. USA 89:8981.

Agarwal et al., 1988, "Oligodeoxynucleoside phosphoramidates and phosphorothioates as inhibitors of human immunodeficiency virus", Proc. Natl. Acad. Sci. USA 85:7079-7083.

Akkina et al, 1996, "High-efficiency gene transfer into CD34+ cells with a human immunodeficiency virus type 1-based retroviral vector pseudotyped with vesicular stomatitis virus envelope glycoprotein G". Journal of Virology 70 (4):2581-2585.

Allen et al., 1993, "Scaffold attachment regions increase reporter gene expression in stably transformed plant cells". Plant Cell 5(6):603-613.

Anderson and Young, 1985, "Quantitative Filter Hybridization", in Nucleic Acid Hybridization—A Practical Approach 73-111.

Animal cell culture. A Practical Approach. Second Edition. 1992, Freshney. The Practical Approach Series. Eds Rickwood D. and Hames B.D. IRL Press, Oxford University Press. New York, Only Table of Contents provided and considered.

Arai et al, 1999, "Dose-dependent transduction of vesicular stomatitis virus G protein-pseudotyped retrovirus vector into human solid tumor cell lines and murine fibroblasts". Virology 260(1):109-115.

Berns, 1991, "Parvoviridae and their Replication" in Fundamental Virology, 2nd Edition, (B.N. Fields and D.M. Knipe, et al.; Raven Press, Ltd., New York).

Binding, 1985, "Regeneration of Plants" in Plant Protoplasts, p. 21 37, CRC Press, Boca Raton.

Boshart et al., 1985, "A very strong enhancer is located upstream of an immediate early gene of human cytomegalovirus". Cell 41(2):521-530.

Brun et al., 1995, "The relationship of Piry virus to other vesiculoviruses: a re-evaluation based on the glycoprotein gene sequence". Intervirol. 38(5):274-282.

Burns et al., 1993, "Vesicular stomatitis virus G glycoprotein pseudotyped retroviral vectors: concentration to very high titer and efficient gene transfer into mammalian and nonmammalian cells". Proc. Natl. Acad. Sci. USA 90 (17):8033-8037.

Carbonneau and Tonks, 1992, "1002 Protein Phosphatases?", Annual Review of Cell Biology, 8:463 93.

Carter, 1992, "Adeno-associated virus vectors". Current Opinion in Biotechnology 3(5):533-539.

Cech et al., 1992, "RNA catalysis by a group I ribozyme. Developing a model for transition state stabilization". J. Biol. Chem. 267(25):17479-17482.

Chen and Okayama, 1987, "High-efficiency transformation of mammalian cells by plasmid DNA". Mol. Cell. Biol., 7 (8):2745-2752.

Cleveland et al., 1983, "Routine large-scale production of monoclonal antibodies in a protein-free culture medium", J. Immunol. Methods 56:221 234.

Cole et al.,1985, "The EBV-Hybridoma Technique and Its Application to Human Lung Cancer", in Monoclonal Antibodies and Cancer Therapy, Alan R. Liss, Inc., pp. 77 96.

Craig, 1996, "Transposon Tn7" Curr. Topics Microbiol. Immunol. 204: 27-48.

De La Cruz et al., 1993, "Characterization of the Tn5 transposase and inhibitor proteins: a model for the inhibition of transposition". J. Bact. 175: 6932-38.

Denyer et al., 1998, "HTS approaches to voltage-gated ion channel drug discovery", Drug Discov. Today 3:323-32.

Dewet et al., 1987, "Firefly Luciferase Gene: Structure and Expression in Mammalian Cells", Mol. Cell. Biol. 7:725.

Dijkema et al., 1985, "Cloning and expression of the chromosomal immune interferon gene of the rat". EMBO J. 4 (3):761-767.

Dorer and Henikoff, 1994, "Expansions of transgene repeats cause heterochromatin formation and gene silencing in Drosophila". Cell 77(7):993-1002.

Evans et al., 1983, Handbook of Plant Cell Culture, 1: 124 176, MacMillan Publishing Co., New York.

Felts et al., 1999,"High-Titer Retroviral Vectors for Gene Delivery", Strategies Newsletter, 12:74-77.

Felts et al., 2000, "Functional Cloning Using ViraPort Retroviral cDNA Expression Libraries" Strategies Newsletter, 13:15-18.

Goff et al., 1981, "Isolation and properties of Moloney murine leukemia virus mutants: use of a rapid assay for release of virion reverse transcriptase". J. Virol. 38(1):239-248.

Gonzales et al., 1999, "Cell-based assays and instrumentation for screening ion-channel targets".Drug. Discov. Today 4(9):431-439.

Gorman et al., 1982, "The Rous sarcoma virus long terminal repeat is a strong promoter when introduced into a variety of eukaryotic cells by DNA-mediated transfection". Proc. Natl. Acad. Sci. USA 79(22):6777-6781.

Graham and Van Der Eb, 1973, "A new technique for the assay of infectivity of human adenovirus 5 DNA". Virol. 52(2):456-467.

Graham et al., 1977, "Characteristics of a human cell line transformed by DNA from human adenovirus type 5". J. Gen Virol., 36:59-74.

Gray et al., 1985, "Periplasmic production of correctly processed human growth hormone in *Escherichia coli*: natural and bacterial signal sequences are interchangeable". Gene 39(2): 247-54.

Haller et al., 1995, "Linker Scanning Mutagenesis of the Internal Ribosome Entry Site of Poliovirus RNA", J. Virol. 66: 5075 5086.

Han et al., 1991, "Inhibition of Moloney murine leukemia virus-induced leukemia in transgenic mice expressing antisense RNA complementary to the retroviral packaging sequences". PNAS 88(10):4313-4317.

Harlow and Lane, 1988, Antibodies: A Laboratory Manual, Cold Spring Harbor Laboratory Press, Cold Spring Harbor, NY, Only Table of Contents provided and considered.

Heikkila et al., 1987, "A c-myc antisense oligodeoxynucleotide inhibits entry into S phase but not progress from G0 to G1". Nature 328(6129):445-449.

Helene et al., 1990, "Specific regulation of gene expression by antisense, sense and antigene nucleic acids". Biochim. Biophys. Acta. 1049(2):99-125.

Hellerman et al., 1984, "Secretion of human parathyroid hormone from rat pituitary cells infected with a recombinant retrovirus encoding preproparathyroid hormone". PNAS 81(17):5340-5344.

Hoess et al., 1986, "The role of the loxP spacer region in P1 site-specific recombination". Nucleic Acids Res. 14 (5):2287-2300.

Huse et al., 1989, Generation of a large combinatorial library of the immunoglobulin repertoire in phage lambda. Science 246(4935):1275 1281.

Jang et al., 1988, "A segment of the 5' nontranslated region of encephalomyocarditis virus RNA directs internal entry of ribosomes during in vitro translation". J. Virol. 62(8): 2636 2643.

Kim et al., 1990, "Use of the human elongation factor 1 alpha promoter as a versatile and efficient expression system". Gene 91(2):217-223.

Köhler and Milstein, 1975, "Continuous cultures of fused cells secreting antibody of predefined specificity". Nature 256(5517):495 497.

Kotin, 1994, "Prospects for the use of adeno-associated virus as a vector for human gene therapy". Human Gene Therapy 5(7):793-801.

Kozbor et al., 1983, "The production of monoclonal antibodies from human lymphocytes", Immunol. Today 4:72.

Kricker et al., 1992, "Dupication-targeted DNA methylation and mutagenesis in the evolution of eukaryotic chromosomes", Proc. Natl. Acad. Sci. 89(3):1075-79.

Krueger et al., 1992, "A human transmembrane protein-tyrosine-phosphatase, PTP zeta, is expressed in brain and has an N-terminal receptor domain homologous to carbonic anhydrases". Proc. Natl. Acad. Sci. USA 89 (16) :7417 7421.

Lebkowski et al., 1988, "Adeno-associated virus: a vector system for efficient introduction and integration of DNA into a variety of mammalian cell types". Molec. Cell. Biol. 8(10):3988-3996.

Maniatis et al., 1987, "Regulation of inducible and tissue-specific gene expression". Science. 236(4806):1237-1245.

* cited by examiner

Wednesday, January 23, 2002 1:31 PM
P-GD1913 pLBC-L2HCF Map.MPD (1 > 7617)  Site and Sequence
Enzymes : 36 of 538 enzymes (Filtered)
Settings :         Circular, Certain Sites Only, Standard Genetic Code FIG. 5 (part 1 of 12)

```
GAATTAATTCATACCAGATCACCGAAAACTGTCCTCCAAATGTGTCCCCCTCACACTCCCAAATTCGCGCGCTTCTGCCT
                                                                                 80
CTTAATTAAGTATGGTCTAGTGGCTTTTGACAGGAGGTTTACACAGGGGGAGTGTGAGGGTTTAAGCGCCCGAAGACGGA
```

SacII
```
CTTAGACCACTCTACCCTATTCCCCACACTCACCGGAGCCAAAGCCGCGGCCCTTCCGTTTCTTTGCTTTTGAAAGACCC
                                                                                 160
GAATCTGGTGAGATGGGATAAGGGGTGTGAGTGGCCTCGGTTTCGGCGCCGGGAAGGCAAAGAAACGAAAACTTCTGGG
```
                                                                    ─── 5' LTR ───

NheI
```
CACCCGTAGGTGGCAAGCTAGCTTAAGTAACGCCACTTTGCAAGGCATGGAAAAATACATAACTGAGAATAGAAAAGTTC
                                                                                 240
GTGGGCATCCACCGTTCGATCGAATTCATTGCGGTGAAACGTTCCGTACCTTTTATGTATTGACTCTTATCTTTTCAAG
```
─────────────────────── 5' LTR ───────────────────────

PvuII           EcoRV
```
AGATCAAGGTCAGGAACAAAGAAACAGCTGAATACCAAACAGGATATCTGTGGTAAGCGGTTCCTGCCCCGGCTCAGGGC
                                                                                 320
TCTAGTTCCAGTCCTTGTTTCTTTGTCGACTTATGGTTTGTCCTATAGACACCATTCGCCAAGGACGGGGCCGAGTCCCG
```
─────────────────────── 5' LTR ───────────────────────

PvuII           EcoRV
```
CAAGAACACATGAGACAGCTGAGTGATGGGCCAAACAGGATATCTGTGGTAAGCAGTTCCTGCCCCGGCTCGGGGCCAAG
                                                                                 400
GTTCTTGTCTACTCTGTCGACTCACTACCCGGTTTGTCCTATAGACACCATTCGTCAAGGACGGGGCCGAGCCCCGGTTC
```
─────────────────────── 5' LTR ───────────────────────

```
AACAGATGGTCCCCAGATGCGGTCCAGCCCTCAGCAGTTTCTAGTGAATCATCAGATGTTTCCAGGGTGCCCCAAGGACC
                                                                                 480
TTGTCTACCAGGGGTCTACGCCAGGTCGGGAGTCGTCAAAGATCACTTAGTAGTCTACAAAGGTCCCACGGGGTTCCTGG
```
─────────────────────── 5' LTR ───────────────────────

```
TGAAAATGACCCTGTACCTTATTTGAACTAACCAATCAGTTCGCTTCTCGCTTCTGTTCGCGCGCTTCCGCTCTCCGAGC
                                                                                 560
ACTTTTACTGGGACATGGAATAAACTTGATTGGTTAGTCAAGCGAAGAGCGAAGACAAGCGCGCGAAGGCGAGAGGCTCG
```
─────────────────────── 5' LTR ───────────────────────

Wednesday, January 23, 2002 1:31 PM
P-GD1913 pLBC-L2HCF Map.MPD (1 > 7617) Site and Sequence FIG. 5 (part 2 of 12)

```
           SacI                    AscI                        SmaI  KpnI
TCAATAAAAGAGCCCACAACCCCTCACTCGGCGCGCCAGTCTTCCGATAGACTGCGTCGCCCGGGTACCCGTATTCCCAA
++++++++++|++++++++|++++++++|++++++++|++++++++|++++++++|++++++++|++++++++|++++ 640
AGTTATTTTCTCGGGTGTTGGGGAGTGAGCCGCGCGGTCAGAAGGCTATCTGACGCAGCGGGCCCATGGGCATAAGGGTT
                                    ─── 5' LTR ───

TAAAGCCTCTTGCTGTTTGCATCCGAATCGTGGTCTCGCTGTTCCTTGGGAGGGTCTCCTCTGAGTGATTGACTACCCAC
++++++++++|++++++++|++++++++|++++++++|++++++++|++++++++|++++++++|++++++++|++++ 720
ATTTCGGAGAACGACAAACGTAGGCTTAGCACCAGAGCGACAAGGAACCCTCCCAGAGGAGACTCACTAACTGATGGGTG
                                    ─── 5' LTR ───

GACGGGGGTCTTTCATTTGGGGGCTCGTCCGGGATTTGGAGACCCCTGCCCAGGGACCACCGACCCACCACCGGGAGGTA
++++++++++|++++++++|++++++++|++++++++|++++++++|++++++++|++++++++|++++++++|++++ 800
CTGCCCCCAGAAAGTAAACCCCCGAGCAGGCCCTAAACCTCTGGGCACGCGTCCCTGGTGGCTGGGTGGTGGCCCTCCAT
═══════════════▶
─── 5' LTR ───┘

SpeI
AGCTGGCCAGCAACTTATCTGTGTCTGTCCGATTGTCTAGTGTCTATGTTTGATGTTATGCGCCTGCGTCTGTACTAGTT
++++++++++|++++++++|++++++++|++++++++|++++++++|++++++++|++++++++|++++++++|++++ 880
TCGACCGGTCGTTGAATAGACACAGACAGGCTAACAGATCACAGATACAAACTACAATACGCGGACGCAGACATGATCAA
         ├──────────────── Extended Packaging Region ────────────────

AGCTAACTAGCTCTGTATCTGGCGGACCCGTGGTGGAACTGACGAGTTCTGAACACCCGGCCGCAACCCTGGGAGACGTC
++++++++++|++++++++|++++++++|++++++++|++++++++|++++++++|++++++++|++++++++|++++ 960
TCGATTGATCGAGACATAGACCGCCTGGGCACCACCTTGACTGCTCAAGACTTGTGGGCCGGCGTTGGGACCCTCTGCAG
───────────────────── Extended Packaging Region ─────────────────────

CCAGGGACTTTGGGGCCCCTTTTTGTGGCCCGACCTGAGGAAGGGAGTCGATGTGGAATCCGACCCCGTCAGGATATGTG
++++++++++|++++++++|++++++++|++++++++|++++++++|++++++++|++++++++|++++++++|++++ 1040
GGTCCCTGAAACCCCCGGCAAAAACACCGGCTGGACTCCTTCCCTCAGCTACACCTTAGGCTGGGGCAGTCCTATACAC
───────────────────── Extended Packaging Region ─────────────────────

GTTCTGGTAGGAGACGAGAACCTAAAACAGTTCCCGCCTCCGTCTGAATTTTTGCTTTCGGTTTGGAACCGAAGCCGCGC
++++++++++|++++++++|++++++++|++++++++|++++++++|++++++++|++++++++|++++++++|++++ 1120
CAAGACCATCCTCTGCTCTTGGATTTTGTCAAGGGCGGAGGCAGACTTAAAAACGAAAGCCAAACCTTGGCTTCGGCGCG
───────────────────── Extended Packaging Region ─────────────────────

PstI   PstI
GTCTTGTCTGCTGCAGCGCTGCAGCATCGTTCTGTGTTGTCTCTGTCTGACTGTGTTTCTGTATTGTCTGAAAATTAGG
++++++++++|++++++++|++++++++|++++++++|++++++++|++++++++|++++++++|++++++++|++++ 1200
CAGAACAGACGACGTCGCGACGTCGTAGCAAGACACAACAGAGACAGACTGACACAAAGACATAAACAGACTTTTAATCC
───────────────────── Extended Packaging Region ─────────────────────
```

FIG. 5 (part 3 of 12)

```
          GCCAGACTGTTACCACTCCCTTAAGTTTGACCTTAGGTCACTGGAAAGATGTCGAGCGGATCGCTCACAACCAGTCGGTA
                                                                                          1280
          CGGTCTGACAATGGTGAGGGAATTCAAACTGGAATCCAGTGACCTTTCTACAGCTCGCCTAGCGAGTGTTGGTCAGCCAT
          ━━━━━━━━━━━━━━━━━━━━━━━━━━━━ Extended Packaging Region ━━━━━━━━━━━━━━━━━━━━━━━━━━

PstI
          GATGTCAAGAAGAGACGTTGGGTTACCTTCTGCTCTGCAGAATGGCCAACCTTTAACGTCGGATGGCCGCGAGACGGCAC
                                                                                          1360
          CTACAGTTCTTCTCTGCAACCCAATGGAAGACGAGACGTCTTACCGGTTGGAAATTGCAGCCTACCGGCGCTCTGCCGTG
          ━━━━━━━━━━━━━━━━━━━━━━━━━━━━ Extended Packaging Region ━━━━━━━━━━━━━━━━━━━━━━━━━━

CTTTAACCGAGACCTCATCACCCAGGTTAAGATCAAGGTCTTTTCACCTGGCCCGCATGGACACCCAGACCAGGTCCCCT
                                                                                          1440
          GAAATTGGCTCTGGAGTAGTGGGTCCAATTCTAGTTCCAGAAAAGTGGACCGGGCGTACCTGTGGGTCTGGTCCAGGGGA
          ━━━━━━━━━━━━━━━━━━━━━━━━━━━━ Extended Packaging Region ━━━━━━━━━━━━━━━━━━━━━━━━━━

ACATCGTGACCTGGGAAGCCTTGGCTTTTGACCCCCTCCCTGGGTCAAGCCCTTTGTACACCCTAAGCCTCCGCCTCCT
                                                                                          1520
          TGTAGCACTGGACCCTTCGGAACCGAAAACTGGGGGAGGGACCCAGTTCGGGAAACATGTGGGATTCGGAGGCGGAGGA
          ━━━━━━━━━━━━━━━━━━━━━━━━━━━━ Extended Packaging Region ━━━━━━━━━━━━━━━━━━━━━━━━━━

CTTCCTCCATCCGCCCCGTCTCTCCCCCTTGAACCTCCTCGTTCGACCCCGCCTCGATCCTCCCTTTATCCAGCCCTCAC
                                                                                          1600
          GAAGGAGGTAGGCGGGGCAGAGAGGGGGAACTTGGAGGAGCAAGCTGGGGCGGAGCTAGGAGGGAAATAGGTCGGGAGTG
          ━━━━━━━━━━━━━━━━━━━━━━━━━━━━ Extended Packaging Region ━━━━━━━━━━━━━━━━━━━━━━━━━━

NarI   EcoRI    BclI                                              BclI
          TCCTTCTCTAGGCGCCGGAATTCCGATCTGATCAAGAGACAGGATGAGGGAGCTTGTATATCCATTTTCGGATCTGATCA
                                                                                          1680
          AGGAAGAGATCCGCGGCCTTAAGGCTAGACTAGTTCTCTGTCCTACTCCCTCGAACATATAGGTAAAAGCCTAGACTAGT
          ━━━━━━━━━━━━━━━━━━
          -Extended Packaging NcoI
          GCACGTGTTGACAATTAATCATCGGCATAGTATATCGGCATAGTATAATACGACAAGGTGAGGAACTAAACCATGGCCAA
                                                                                          1760
          CGTGCACAACTGTTAATTAGTAGCCGTATCATATAGCCGTATCATATTATGCTGTTCCACTCCTTGATTTGGTACCGGTT
                                                                             Met Ala Lys
          ━━━━━━━━━━━━━━━━━━━━ EM7 Promoter ━━━━━━━━━━━━━━━━━━━━━              ━Blast━

GCCTTTGTCTCAAGAAGAATCCACCCTCATTGAAAGAGCAACGGCTACAATCAACAGCATCCCCATCTCTGAAGACTACA
                                                                                          1840
          CGGAAACAGAGTTCTTCTTAGGTGGGAGTAACTTTCTCGTTGCCGATGTTAGTTGTCGTAGGGGTAGACACTTCTGATGT
           Pro Leu Ser Gln Glu Glu Ser Thr Leu Ile Glu Arg Ala Thr Ala Thr Ile Asn Ser Ile Pro Ile Ser Glu Asp Tyr
          ━━━━━━━━━━━━━━━━━━━━━━━━━━━━━━━━━━━━━━ Blast ━━━━━━━━━━━━━━━━━━━━━━━━━━━━━━━━━━
```

Wednesday, January 23, 2002 1:31 PM
P-GD1913 pLBC-L2HCF Map.MPD (1 > 7617)  Site and Sequence FIG. 5 (part 4 of 12)

```
GCGTCGCCAGCGCAGCTCTCTCTAGCGACGGCCGCATCTTCACTGGTGTCAATGTATATCATTTTACTGGGGACCTTGT
CGCAGCGGTCGCGTCGAGAGAGATCGCTGCCGGCGTAGAAGTGACCACAGTTACATATAGTAAAATGACCCCCTGGAACA    1920
Ser Val Ala Ser Ala Ala Leu Ser Ser Asp Gly Arg Ile Phe Thr Gly Val Asn Val Tyr His Phe Thr Gly Gly Pro Cys
                                                    Blast
```

Pvull                              Nrul Pvul
```
GCAGAACTCGTGGTGCTGGGCACTGCTGCTGCTGCGGCAGCTGGCAACCTGACTTGTATCGTCGCGATCGGAAATGAGAA
CGTCTTGAGCACCACGACCCGTGACGACGACGACGCCGTCGACCGTTGGACTGAACATAGCAGCGCTAGCCTTTACTCTT    2000
Ala Glu Leu Val Val Leu Gly Thr Ala Ala Ala Ala Ala Gly Asn Leu Thr Cys Ile Val Ala Ile Gly Asp Glu Asn
                                                    Blast
```

Sall
```
CAGGGGCATCTTGAGCCCCTGCGGACGGTGTCGACAGGTGCTTCTCGATCTGCATCCTGGGATCAAAGCGATACTGAAGG
GTCCCCGTAGAACTCGGGGACGCCTGCCACAGCTGTCCACGAAGAGCTAGACGTAGGACCCTAGTTTCGCTATCACTTCC    2080
Arg Gly Ile Leu Ser Pro Cys Gly Arg Cys Arg Gln Val Leu Leu Asp Leu His Pro Gly Ile Lys Ala Ile Val Lys
                                                    Blast
```

```
ACAGTGATGGACAGCCGACGGCAGTTGGGATTCGTGAATTGCTGCCCTCTGGTTATGTGTGGGAGGGCTAAGCACTTCGT
TGTCACTACCTGTCGGCTGCCGTCAACCCTAAGCACTTAACGACGGGAGACCAATACACACCCTCCCGATTCGTGAAGCA    2160
Asp Ser Asp Gly Gln Pro Thr Ala Val Gly Ile Arg Glu Leu Leu Pro Ser Gly Tyr Val Trp Glu Gly  *
                                                    Blast
```

```
GGCCGAGGAGCAGGACTGACACGTGCTACGAGATTTCGATTCCACCGCCGCCTTCTATGAAAGGTTGGGCTTCGGAATCG
CCGGCTCCTCGTCCTGACTGTGCACGATGCTCTAAAGCTAAGGTGGCGGCGGAAGATACTTTCCAACCCGAAGCCTTAGC    2240
```

```
TTTTCCGGGACGCCGATCCGGCCATTAGCCATATTATTCATTGGTTATATAGCATAAATCAATATTGGCTATTGGCCATT
AAAAGGCCCTGCGGCTAGGCCGGTAATCGGTATAATAAGTAACCAATATATCGTATTTAGTTATAACCGATAACCGGTAA    2320
      └────────────────────── hCMV Promoter ──────────
```

```
GCATACGTTGTATCCATATCATAATATGTACATTTATATTGGCTCATGTCCAACATTACCGCCATGTTGACATTGATTAT
CGTATGCAACATAGGTATAGTATTATACATGTAAATATAACCGAGTACAGGTTGTAATGGCGGTACAACTGTAACTAATA    2400
────────────────────────────── hCMV Promoter ──────────
```

Spel
```
TGACTAGTTATTAATAGTAATCAATTACGGGGTCATTAGTTCATAGCCCATATATGGAGTTCCGCGTTACATAACTTACG
ACTGATCAATAATTATCATTAGTTAATGCCCCAGTAATCAAGTATCGGGTATATACCTCAAGGCGCAATGTATTGAATGC    2480
────────────────────────────── hCMV Promoter ──────────
```

Wednesday, January 23, 2002 1:31 PM
P-GD1913 pLBC-L2HCF Map.MPD (1 > 7617) Site and Sequence FIG. 5 (part 5 of 12)

```
GTAAATGGCCCGCCTGGCTGACCGCCCAACGACCCCCGCCCATTGACGTCAATAATGACGTATGTTCCCATAGTAACGCC
                                                                                  2560
CATTTACCGGGCGGACCGACTGGCGGGTTGCTGGGGGCGGGTAACTGCAGTTATTACTGCATACAAGGGTATCATTGCGG
                                    hCMV Promoter
                                                                    Ndel
AATAGGGACTTTCCATTGACGTCAATGGGTGGAGTATTTACGGTAAACTGCCCACTTGGCAGTACATCAAGTGTATCATA
                                                                                  2640
TTATCCCTGAAAGGTAACTGCAGTTACCCACCTCATAAATGCCATTTGACGGGTGAACCGTCATGTAGTTCACATAGTAT
                                    hCMV Promoter TGCCAAGTACGCCCCCTATTGACGTCAATGACGGTAAATGGCCCGCCTGGCATTATGCCCAGTACATGACCTTATGGGAC
                                                                                  2720
ACGGTTCATGCGGGGGATAACTGCAGTTACTGCCATTTACCGGGCGGACCGTAATACGGGTCATGTACTGGAATACCCTG
                                    hCMV Promoter
                          Ncol
TTTCCTACTTGGCAGTACATCTACGTATTAGTCATCGCTATTACCATGGTGATGCGGTTTTGGCAGTACATCAATGGGCG
                                                                                  2800
AAAGGATGAACCGTCATGTAGATGCATAATCAGTAGCGATAATGGTACCACTACGCCAAAACCGTCATGTAGTTACCCGC
                                    hCMV Promoter TGGATAGCGGTTTGACTCACGGGGATTTCCAAGTCTCCACCCCATTGACGTCAATGGGAGTTTGTTTTGGCACCAAAATC
                                                                                  2880
ACCTATCGCCAAACTGAGTGCCCCTAAAGGTTCAGAGGTGGGGTAACTGCAGTTACCCTCAAACAAAACCGTGGTTTTAG
                                    hCMV Promoter AACGGGACTTTCCAAAATGTCGTAACAACTCCGCCCCATTGACGCAAATGGGCGGTAGGCATGTACGGTGGGAGGTCTAT
                                                                                  2960
TTGCCCTGAAAGGTTTTACAGCATTGTTGAGGCGGGGTAACTGCGTTTACCCGCCATCCGTACATGCCACCCTCCAGATA
                                    hCMV Promoter
      Sacl
ATAAGCAGAGCTCGTTTAGTGAACCGTCAGATCGCCTGGAGACGCCATCCACGCTGTTTTGACCTCCATAGAAGACACCG
                                                                                  3040
TATTCGTCTCGAGCAAATCACTTGGCAGTCTAGCGGACCTCTGCGGTAGGTGCGACAAAACTGGAGGTATCTTCTGTGGC
                                    hCMV Promoter
```

FIG. 5 (part 6 of 12)

```
                SacII    HindIII
GGACCGATCCAGCCTCCGCGGCCCCAAGCTTGTTATCACAACTTTCTACAAAAAAGCAGGCTTCGAAGGAGATAGAACCA
                                                                                  3120
CCTGGCTAGGTCGGAGGCGCCGGGGTTCGAACAATAGTGTTCAAACATGTTTTTTCGTCCGAAGCTTCCTCTATCTTGGT hCMV Promoter              aatB1
```

```
              NcoI
ATTCTCTAAGGAAATACTTAACCATGGGATGGAGCTGTATCATCCTCTTCTTGGTAGCAACAGCTACAGGTGTCCACTCC
                                                                                  3200
TAAGAGATTCCTTTATGAATTGGTACCCTACCTCGACATAGTAGGAGAAGAACCATCGTTGTCGATGTCCACAGGTGAGG
                      Met Gly Trp Ser Cys Ile Ile Leu Phe Leu Val Ala Thr Ala Thr Gly Val His Ser
                                              LL2 HCF
```

```
    PvuII
CAGGTCCAGCTGGTCCAATCAGGGGCTGAAGTCAAGAAACCTGGGTCATCAGTGAAGGTCTCCTGCAAGGCTTCTGGCTA
                                                                                  3280
GTCCAGGTCGACCAGGTTAGTCCCCGACTTCAGTTCTTTGGACCCAGTAGTCACTTCCAGAGGACGTTCCGAAGACCGAT
Gln Val Gln Leu Val Gln Ser Gly Ala Glu Val Lys Lys Pro Gly Ser Ser Val Lys Val Ser Cys Lys Ala Ser Gly Tyr
                                              LL2 HCF
```

```
CACCTTTACTAGCTACTGGCTGCACTGGGTCAGGCAGGCACCTGGACAGGGTCTGGAATGGATTGGATACATTAATCCTA
                                                                                  3360
GTGGAAATGATCGATGACCGACGTGACCCAGTCCGTCCGTGGACCTGTCCCAGACCTTACCTAACCTATGTAATTAGGAT
Thr Phe Thr Ser Tyr Trp Leu His Trp Val Arg Gln Ala Pro Gly Gln Gly Leu Glu Trp Ile Gly Tyr Ile Asn Pro
                                              LL2 HCF
```

```
                                              PstI
GGAATGATTATACTGAGTACAATCAGAACTTCAAGGACAAGGCCACAATAACTGCAGACGAATCCACCAATACAGCCTAC
                                                                                  3440
CCTTACTAATATGACTCATGTTAGTCTTGAAGTTCCTGTTCCGGTGTTATTGACGTCTGCTTAGGTGGTTATGTCGGATG
Arg Asn Asp Tyr Thr Glu Tyr Asn Gln Asn Phe Lys Asp Lys Ala Thr Ile Thr Ala Asp Glu Ser Thr Asn Thr Ala Tyr
                                              LL2 HCF
```

```
ATGGAGCTGAGCAGCCTGAGGTCTGAGGACACGGCATTTTATTTTTGTCCAAGAAGGGATATTACTACGTTCTACTGGGG
                                                                                  3520
TACCTCGACTCGTCGGACTCCAGACTCCTGTGCCGTAAAATAAAAACAGGTTCTTCCCTATAATGATGCAAGATGACCCC
Met Glu Leu Ser Ser Leu Arg Ser Glu Asp Thr Ala Phe Tyr Phe Cys Ala Arg Arg Asp Ile Thr Thr Phe Tyr Trp Gly
                                              LL2 HCF
```

```
                          ApaI
CCAAGGCACCACGGTCACCGTCTCCTCAGCCTCCACCAAGGGCCCATCGGTCTTCCCCCTGGCACCCTCCTCCAAGAGCA
                                                                                  3600
GGTTCCGTGGTGCCAGTGGCAGAGGAGTCGGAGGTGGTTCCCGGGTAGCCAGAAGGGGGACCGTGGGAGGAGGTTCTCGT
Gln Gly Thr Thr Val Thr Val Ser Ser Ala Ser Thr Lys Gly Pro Ser Val Phe Pro Leu Ala Pro Ser Ser Lys Ser
                                              LL2 HCF
```

Wednesday, January 23, 2002 1:31 PM
P-GD1913 pLBC-L2HCF Map.MPD (1 > 7617) Site and Sequence FIG. 5 (part 7 of 12)

```
                                                                                       NarI
CCTCTGGGGGCACAGCGGCCCTGGGCTGCCTGGTCAAGGACTACTTCCCCGAACCGGTGACGGTGTCGTGGAACTCAGGC
++++++++++++++++++++++++++++++++++++++++++++++++++++++++++++++++++++++++++++++++  3680
GGAGACCCCCGTGTCGCCGGGACCCGACGGACCAGTTCCTGATGAAGGGGCTTGGCCACTGCCACAGCACCTTGAGTCCG
 Thr Ser Gly Gly Thr Ala Ala Leu Gly Cys Leu Val Lys Asp Tyr Phe Pro Glu Pro Val Thr Val Ser Trp Asn Ser Gly
                                    ———————————————— LL2 HCF ————————————————

GCCCTGACCAGCGGCGTGCACACCTTCCCGGCTGTCCTACAGTCCTCAGGACTCTACTCCCTCAGCAGCGTGGTGACCGT
++++++++++++++++++++++++++++++++++++++++++++++++++++++++++++++++++++++++++++++++  3760
CGGGACTGGTCGCCGCACGTGTGGAAGGGCCGACAGGATGTCAGGAGTCCTGAGATGAGGGAGTCGTCGCACCACTGGCA
 Ala Leu Thr Ser Gly Val His Thr Phe Pro Ala Val Leu Gln Ser Ser Gly Leu Tyr Ser Leu Ser Ser Val Val Thr Val
                                    ———————————————— LL2 HCF ————————————————

GCCCTCCAGCAGCTTGGGCACCCAGACCTACATCTGCAACGTGAATCACAAGCCCAGCAACACCAAGGTGGACAAGAGAG
++++++++++++++++++++++++++++++++++++++++++++++++++++++++++++++++++++++++++++++++  3840
CGGGAGGTCGTCGAACCCGTGGGTCTGGATGTAGACGTTGCACTTAGTGTTCGGGTCGTTGTGGTTCCACCTGTTCTCTC
 Pro Ser Ser Ser Leu Gly Thr Gln Thr Tyr Ile Cys Asn Val Asn His Lys Pro Ser Asn Thr Lys Val Asp Lys Arg
                                    ———————————————— LL2 HCF ————————————————

TTGAGCCCAAATCTTGTGACAAAACTCACACATGCCCACCGTGCCCAGCACCTGAACTCCTGGGGGGACCGTCAGTCTTC
++++++++++++++++++++++++++++++++++++++++++++++++++++++++++++++++++++++++++++++++  3920
AACTCGGGTTTAGAACACTGTTTTGAGTGTGTACGGGTGGCACGGGTCGTGGACTTGAGGACCCCCCTGGCAGTCAGAAG
 Val Glu Pro Lys Ser Cys Asp Lys Thr His Thr Cys Pro Pro Cys Pro Ala Pro Glu Leu Leu Gly Gly Pro Ser Val Phe
                                    ———————————————— LL2 HCF ————————————————

BspHI
CTCTTCCCCCCAAAACCCAAGGACACCCTCATGATCTCCCGGACCCCTGAGGTCACATGCGTGGTGGTGGACGTGAGCCA
++++++++++++++++++++++++++++++++++++++++++++++++++++++++++++++++++++++++++++++++  4000
GAGAAGGGGGGTTTTGGGTTCCTGTGGGAGTACTAGAGGGCCTGGGGACTCCAGTGTACGCACCACCACCTGCACTCGGT
 Leu Phe Pro Pro Lys Pro Lys Asp Thr Leu Met Ile Ser Arg Thr Pro Glu Val Thr Cys Val Val Val Asp Val Ser His
                                    ———————————————— LL2 HCF ————————————————

SacII
CGAAGACCCTGAGGTCAAGTTCAACTGGTACGTGGACGGCGTGGAGGTGCATAATGCCAAGACAAAGCCGCGGGAGGAGC
++++++++++++++++++++++++++++++++++++++++++++++++++++++++++++++++++++++++++++++++  4080
GCTTCTGGGACTCCAGTTCAAGTTGACCATGCACCTGCCGCACCTCCACGTATTACGGTTCTGTTTCGGCGCCCTCCTCG
 Glu Asp Pro Glu Val Lys Phe Asn Trp Tyr Val Asp Gly Val Glu Val His Asn Ala Lys Thr Lys Pro Arg Glu Glu
                                    ———————————————— LL2 HCF ————————————————

AGTACAACAGCACGTACCGTGTGGTCAGCGTCCTCACCGTCCTGCACCAGGACTGGCTGAATGGCAAGGAGTACAAGTGC
++++++++++++++++++++++++++++++++++++++++++++++++++++++++++++++++++++++++++++++++  4160
TCATGTTGTCGTGCATGGCACACCAGTCGCAGGAGTGGCAGGACGTGGTCCTGACCGACTTACCGTTCCTCATGTTCACG
 Gln Tyr Asn Ser Thr Tyr Arg Val Val Ser Val Leu Thr Val Leu His Gln Asp Trp Leu Asn Gly Lys Glu Tyr Lys Cys
                                    ———————————————— LL2 HCF ————————————————

AAGGTCTCCAACAAAGCCCTCCCAGCCCCCATCGAGAAAACCATCTCCAAAGCCAAAGGGCAGCCCCGAGAACCACAGGT
++++++++++++++++++++++++++++++++++++++++++++++++++++++++++++++++++++++++++++++++  4240
TTCCAGAGGTTGTTTCGGGAGGGTCGGGGGTAGCTCTTTTGGTAGAGGTTTCGGTTTCCCGTCGGGGCTCTTGGTGTCCA
 Lys Val Ser Asn Lys Ala Leu Pro Ala Pro Ile Glu Lys Thr Ile Ser Lys Ala Lys Gly Gln Pro Arg Glu Pro Gln Val
                                    ———————————————— LL2 HCF ————————————————
```

Wednesday, January 23, 2002 1:31 PM
P-GD1913 pLBC-L2HCF Map.MPD (1 > 7617)  Site and Sequence FIG. 5 (part 8 of 12)

```
          SmaI
GTACACCCTGCCCCCATCCCGGGAGGAGATGACCAAGAACCAGGTCAGCCTGACCTGCCTGGTCAAAGGCTTCTATCCCA
++++++++++|++++++++++|++++++++++|++++++++++|++++++++++|++++++++++|++++++++++|++++  4320
CATGTGGGACGGGGGTAGGGCCCTCCTCTACTGGTTCTTGGTCCAGTCGGACTGGACGGACCAGTTTCCGAAGATAGGGT
 Tyr Thr Leu Pro Pro Ser Arg Glu Glu Met Thr Lys Asn Gln Val Ser Leu Thr Cys Leu Val Lys Gly Phe Tyr Pro
                                        LL2 HCF

GCGACATCGCCGTGGAGTGGGAGAGCAATGGGCACCCGCAGAACAACTACAAGACCACGCCTCCCGTGCTGGACTCCGAC
++++++++++|++++++++++|++++++++++|++++++++++|++++++++++|++++++++++|++++++++++|++++  4400
CGCTGTAGCGGCACCTCACCCTCTCGTTACCCGTCGGCCTCTTGTTGATGTTCTGGTGCGGAGGGCACGACCTGAGGCTG
 Ser Asp Ile Ala Val Glu Trp Glu Ser Asn Gly Gln Pro Glu Asn Asn Tyr Lys Thr Thr Pro Pro Val Leu Asp Ser Asp
                                        LL2 HCF

GGCTCCTTCTTCCTCTATAGCAAGCTCACCGTGGACAAGAGCAGGTGGCAGCAGGGGAACGTCTTCTCATGCTCCGTGAT
++++++++++|++++++++++|++++++++++|++++++++++|++++++++++|++++++++++|++++++++++|++++  4480
CCGAGGAAGAAGGAGATATCGTTCGAGTGGCACCTGTTCTCGTCCACCGTCGTCCCCTTGCAGAAGAGTACGAGGCACTA
 Gly Ser Phe Phe Leu Tyr Ser Lys Leu Thr Val Asp Lys Ser Arg Trp Gln Gln Gly Asn Val Phe Ser Cys Ser Val Met
                                        LL2 HCF

SmaI            EcoRI   NotI
GCACGAGGCTCTGCACAACCACTACACGCAGAAGAGCCTCTCCCTGTCTCCCGGGAAATGAAAGCCGAATTCGCGGCCGC
++++++++++|++++++++++|++++++++++|++++++++++|++++++++++|++++++++++|++++++++++|++++  4560
CGTGCTCCGAGACGTGTTGGTGATGTGCGTCTTCTCGGAGAGGGACAGAGGGCCCTTTACTTTCGGCTTAAGCGCCGGCG
 His Glu Ala Leu His Asn His Tyr Thr Gln Lys Ser Leu Ser Leu Ser Pro Gly Lys  •
                                        LL2 HCF

EcoRV
  XhoI  XbaI                                   ClaI
ACTCGAGATATCTAGACCCAGCTTTCTTGTACAAAGTGGTGATAACATCGATAAAATAAAAGATTTTATTTAGTCTCCAG
++++++++++|++++++++++|++++++++++|++++++++++|++++++++++|++++++++++|++++++++++|++++  4640
TGAGCTCTATAGATCTGGGTCGAAAGAACATGTTTCACCACTATTGTAGCTATTTTATTTTCTAAAATAAATCAGAGGTC
               ├──────────── attB2 ────────────┤

NheI
AAAAAGGGGGAATGAAAGACCCCACCTGTAGGTTTGGCAAGCTAGCTTAAGTAACGCCATTTTGCAAGGCATGGAAAAA
++++++++++|++++++++++|++++++++++|++++++++++|++++++++++|++++++++++|++++++++++|++++  4720
TTTTTCCCCCCTTACTTTCTGGGGTGGACATCCAAACCGTTCGATCGAATTCATTGCGGTAAAACGTTCCGTACCTTTTT
                              3' LTR
                              3' LTR

PvuII                            EcoRV
TACATAACTGAGAATAGAGAACTTCAGATCAAGGTCAGGAACAGATGGAACAGCTGAATATGGGCCAAACAGGATATCTG
++++++++++|++++++++++|++++++++++|++++++++++|++++++++++|++++++++++|++++++++++|++++  4800
ATGTATTGACTCTTATCTCTTCAAGTCTAGTTCCAGTCCTTGTCTACCTTGTCGACTTATACCCGGTTTGTCCTATAGAC
                              3' LTR
                              3' LTR
```

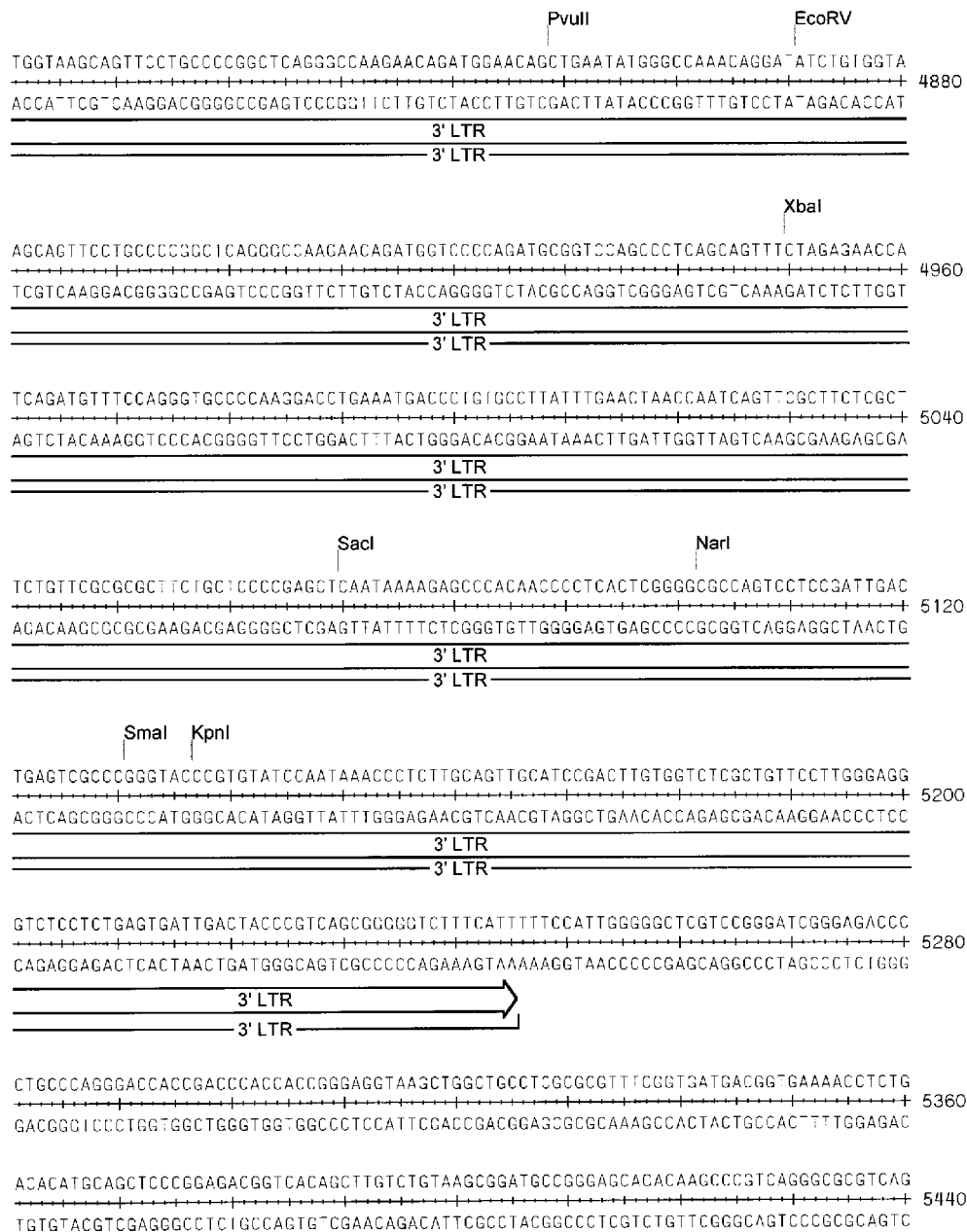
FIG. 5 (part 9 of 12)

Wednesday, January 23, 2002 1:31 PM
P-GD1913 pLBC-L2HCF Map.MPD  (1 > 7617)  Site and Sequence FIG. 5 (part 10 of 12)

```
CGGGTGTTGGCGGGTGTCGGGGCGCAGCCATGACCCAGTCACGTAGCGATAGCGGAGTGTATACTGGCTTAACTATGCGG
                                                                                 5520
GCCCACAACCGCCCACAGCCCCGCGTCGGTACTGGGTCAGTGCATCCCTATCGCCTCACATATGACCGAATTGATACGCC

NdeI
CATCAGAGCAGATTGTACTGAGAGTGCACCATATGCGGTGTCAAATACCCCACAGATGCGTAAGGAGAAAATACCGCATC
                                                                                 5600
GTAGTCTCGTCTAACATGACTCTCACGTGGTATACGCCACACTTTATGGCGTGTCTACGCATTCCTCTTTTATGGCGTAG

AGGCGCTCTTCCGCTTCCTCGCTCACTGACTCGCTGCGCTCGGTCGTTCGGCTGCGGCGAGCGGTATCAGCTCACTCAAA
                                                                                 5680
TCCGCGAGAAGGCGAAGGAGCGAGTGACTGAGCGACGCGAGCCAGCAAGCCGACGCCGCTCGCCATAGTCGAGTGAGTTT

GGCGGTAATACGGTTATCCACAGAATCAGGGGATAACGCAGGAAAGAACATGTGAGCAAAAGGCCAGCAAAAGGCCAGGA
                                                                                 5760
CCGCCATTATGCCAATAGGTGTCTTAGTCCCCTATTGCGTCCTTTCTTGTACACTCGTTTTCCGGTCGTTTTCCGGTCCT

ACCGTAAAAAGGCCGCGTTGCTGGCGTTTTTCCATAGGCTCCGCCCCCTGACGAGCATCACAAAAATCGACGCTCAAGT
                                                                                 5840
TGGCATTTTTCCGGCGCAACGACCGCAAAAAGGTATCCGAGGCGGGGGGACTGCTCGTAGTGTTTTTAGCTGCGAGTTCA

CAGAGGTGGCGAAACCCGACAGGACTATAAAGATACCAGGCGTTTCCCCCTGGAAGCTCCCTCGTGCGCTCTCCTGTTCC
                                                                                 5920
GTCTCCACCGCTTTGGGCTGTCCTGATATTTCTATGGTCCGCAAAGGGGGACCTTCGAGGGAGCACGCGAGAGGACAAGG

GACCCTGCCGCTTACCGGATACCTGTCCGCCTTTCTCCCTTCGGGAAGCGTGGCGCTTTCTCATAGCTCACGCTGTAGGT
                                                                                 6000
CTGGGACGGCGAATGGCCTATGGACAGGCGGAAAGAGGGAAGCCCTTCGCACCGCGAAAGAGTATCGAGTGCGACATCCA

ATCTCAGTTCGGTGTAGGTCGTTCGCTCCAAGCTGGGCTGTGTGCACGAACCCCCCGTTCAGCCCGACCGCTGCGCCTTA
                                                                                 6080
TAGAGTCAAGCCACATCCAGCAAGCGAGGTTCGACCCGACACACGTGCTTGGGGGGCAAGTCGGGCTGGCGACGCGGAAT

TCCGGTAACTATCGTCTTGAGTCCAACCCGGTAAGACACGACTTATCGCCACTGGCAGCAGCCACTGGTAACAGGATTAG
                                                                                 6160
AGGCCATTGATAGCAGAACTCAGGTTGGGCCATTCTGTGCTGAATAGCGGTGACCGTCGTCGGTGACCATTGTCCTAATC

CAGAGCGAGGTATGTAGGCCGTGCTACAGAGTTCTTGAAGTGGTGGCCTAACTACGGCTACACTAGAAGGACAGTATTTG
                                                                                 6240
GTCTCGCTCCATACATCCGCCACGATGTCTCAAGAACTTCACCACCGGATTGATGCCGATGTGATCTTCCTGTCATAAAC

GTATCTGCGCTCTGCTGAAGCCAGTTACCTTCGGAAAAAGAGTTGGTAGCTCTTGATCCGGCAAACAAACCACCGCTGGT
                                                                                 6320
CATAGACGCGAGACGACTTCGGTCAATGGAAGCCTTTTTCTCAACCATCGAGAACTAGGCCGTTTGTTTGGTGGCGACCA

AGCGGTGGTTTTTTTGTTTGCAAGCAGCAGATTACGCGCAGAAAAAAAGGATCTCAAGAAGATCCTTTGATCTTTTCTAC
                                                                                 6400
TCGCCACCAAAAAAACAAACGTTCGTCGTCTAATGCGCGTCTTTTTTTCCTAGAGTTCTTCTAGGAAACTAGAAAAGATG
```

Wednesday, January 23, 2002 1:31 PM
P-GD1913 pLBC-L2HCF Map.MPD (1 > 7617)  Site and Sequence FIG. 5 (part 11 of 12)

```
                                      BspHI
GGGGTCTGACGCTCAGTGGAACGAAAACTCACGTTAAGGGATTTTGGTCATGAGATTATCAAAAAGGATCTTCACCTAGA
++++++++++++++++++++++++++++++++++++++++++++++++++++++++++++++++++++++++++++++  6480
CCCCAGACTGCGAGTCACCTTGCTTTTGAGTGCAATTCCCTAAAACCAGTACTCTAATAGTTTTCCTAGAAGTGGATCT

DraI                    DraI
TCCTTTTAAATTAAAAATGAAGTTTTAAATCAATCTAAAGTATATATGAGTAAACTTGGTCTGACAGTTACCAATGCTTA
++++++++++++++++++++++++++++++++++++++++++++++++++++++++++++++++++++++++++++++  6560
AGGAAAATTTAATTTTTACTTCAAAATTTAGTTAGATTTCATATATACTCATTTGAACCAGACTGTCAATGGTTACGAAT
                                                                    ·  Trp His Lys
                                                                   └ b-Lactamase ─

ATCAGTGAGGCACCTATCTCAGCGATCTGTCTATTTCGTTCATCCATAGTTGCCTGACTCCCCGTCGTGTAGATAACTAC
++++++++++++++++++++++++++++++++++++++++++++++++++++++++++++++++++++++++++++++  6640
TAGTCACTCCGTGGATAGAGTCGCTAGACAGATAAAGCAAGTAGGTATCAACGGACTGAGGGGCAGCACATCTATTGATG
 Ile Leu Ser Ala Gly Ile Glu Ala Ile Gln Arg Asn Arg Glu Asp Met Thr Ala Gln Ser Gly Thr Thr Tyr Ile Val Val
───────────────────────────────────── b-Lactamase ─────────────────────────────────

GATACGGGAGGGCTTACCATCTGGCCCCAGTGCTGCAATGATACCGCGAGACCCACGCTCACCGGCTCCAGATTTATCAG
++++++++++++++++++++++++++++++++++++++++++++++++++++++++++++++++++++++++++++++  6720
CTATGCCCTCCCGAATGGTAGACCGGGGTCACGACGTTACTATGGCGCTCTGGGTGCGAGTGGCCGAGGTCTAAATAGTC
 Ile Arg Ser Pro Lys Gly Asp Pro Gly Leu Ala Ala Ile Ile Gly Arg Ser Gly Arg Glu Gly Ala Gly Ser Lys Asp Ala
───────────────────────────────────── b-Lactamase ─────────────────────────────────

CAATAAACCAGCCAGCCGGAAGGGCCGAGCGCAGAAGTGGTCCTGCAACTTTATCCGCCTCCATCCAGTCTATTAATTGT
++++++++++++++++++++++++++++++++++++++++++++++++++++++++++++++++++++++++++++++  6800
GTTATTTGGTCGGTCGGCCTTCCCGGCTCGCGTCTTCACCAGGACGTTGAAATAGGCGGAGGTAGGTCAGATAATTAACA
 Ile Phe Trp Gly Ala Pro Leu Ala Ser Arg Leu Leu Pro Gly Ala Val Lys Asp Ala Glu Met Trp Asp Ile Leu Gln
───────────────────────────────────── b-Lactamase ─────────────────────────────────

FspI                    PstI
TGCCGGGAAGCTAGAGTAAGTAGTTCGCCAGTTAATAGTTTGCGCAACGTTGTTGCCATTGCTGCAGGCATCGTGGTGTC
++++++++++++++++++++++++++++++++++++++++++++++++++++++++++++++++++++++++++++++  6880
ACGGCCCTTCGATCTCATTCATCAAGCGGTCAATTATCAAACGCGTTGCAACAACGGTAACGACGTCCGTAGCACCACAG
 Gln Arg Ser Ala Leu Thr Leu Leu Glu Gly Thr Leu Leu Lys Arg Leu Thr Thr Ala Met Ala Ala Pro Met Thr Thr Asp
───────────────────────────────────── b-Lactamase ─────────────────────────────────

ACGCTCGTCGTTTGGTATGGCTTCATTCAGCTCCGGTTCCCAACGATCAAGGCGAGTTACATGATCCCCCATGTTGTGCA
++++++++++++++++++++++++++++++++++++++++++++++++++++++++++++++++++++++++++++++  6960
TGCGAGCAGCAAACCATACCGAAGTAAGTCGAGGCCAAGGGTTGCTAGTTCCGCTCAATGTACTAGGGGGTACAACACGT
 Arg Glu Asp Asn Pro Ile Ala Glu Asn Leu Glu Pro Glu Trp Arg Asp Leu Arg Thr Val His Asp Gly Met Asn His Leu
───────────────────────────────────── b-Lactamase ─────────────────────────────────

PvuI
AAAAAGCGGTTAGCTCCTTCGGTCCTCCGATCGTTGTCAGAAGTAAGTTGGCCGCAGTGTTATCACTCATGGTTATGGCA
++++++++++++++++++++++++++++++++++++++++++++++++++++++++++++++++++++++++++++++  7040
TTTTTCGCCAATCGAGGAAGCCAGGAGGCTAGCAACAGTCTTCATTCAACCGGCGTCACAATAGTGAGTACCAATACCGT
 Phe Ala Thr Leu Glu Lys Pro Gly Gly Ile Thr Thr Leu Leu Leu Asn Ala Ala Thr Asn Asp Ser Met Thr Ile Ala
───────────────────────────────────── b-Lactamase ─────────────────────────────────
```

FIG. 5 (part 12 of 12)

```
GCACTGCATAATTCTCTTACTGTCATGCCATCCGTAAGATGCTTTTCTGTGACTGGTGAGTACTCAACCAAGTCATTCTG
++++++++++++++++++++++++++++++++++++++++++++++++++++++++++++++++++++++++++++++++ 7120
CGTGACGTATTAAGAGAATGACAGTACGGTAGGCATTCTACGAAAAGACACTGACCACTCATGAGTTGGTTCAGTAAGAC
 Ala Ser Cys Leu Glu Arg Val Thr Met Gly Asp Thr Leu His Lys Glu Thr Val Pro Ser Tyr Glu Val Leu Asp Asn Gln
                                          b-Lactamase
```

DraI

```
AGAATAGTGTATGCGGCGACCGAGTTGCTCTTGCCCGGCGTCAACACGGGATAATACCGCGCCACATAGCAGAACTTTAA
++++++++++++++++++++++++++++++++++++++++++++++++++++++++++++++++++++++++++++++++ 7200
TCTTATCACATACGCCGCTGGCTCAACGAGAACGGGCCGCAGTTGTGCCCTATTATGGCGCGGTGTATCGTCTTGAAATT
 Ser Tyr His Ile Arg Arg Gly Leu Gln Glu Gln Gly Ala Asp Val Arg Ser Leu Val Ala Gly Cys Leu Leu Val Lys Phe
                                          b-Lactamase
```

```
AAGTGCTCATCATTGGAAAACGTTCTTCGGGGCGAAAACTCTCAAGGATCTTACCGCTGTTGAGATCCAGTTCGATGTAA
++++++++++++++++++++++++++++++++++++++++++++++++++++++++++++++++++++++++++++++++ 7280
TTCACGAGTAGTAACCTTTTGCAAGAAGCCCCGCTTTTGAGAGTTCCTAGAATGGCGACAACTCTAGGTCAAGCTACATT
 Thr Ser Met Met Pro Phe Arg Glu Glu Pro Arg Phe Ser Glu Leu Ile Lys Gly Ser Asn Leu Asp Leu Glu Ile Tyr
                                          b-Lactamase
```

```
CCCACTCGTGCACCCAACTGATCTTCAGCATCTTTTACTTTCACCAGCGTTTCTGGGTGAGCAAAAACAGGAAGGCAAAA
++++++++++++++++++++++++++++++++++++++++++++++++++++++++++++++++++++++++++++++++ 7360
GGGTGAGCACGTGGGTTGACTAGAAGTCGTAGAAAATGAAAGTGGTCGCAAAGACCCACTCGTTTTTGTCCTTCCGTTTT
 Gly Val Arg Ala Gly Leu Gln Asp Glu Ala Asp Lys Val Lys Val Leu Thr Glu Pro His Ala Phe Val Pro Leu Cys Phe
                                          b-Lactamase
```

```
TGCCGCAAAAAAGGGAATAAGGGCGACACGGAAATGTTGAATACTCATACTCTTCCTTTTTCAATATTATTGAAGCATTT
++++++++++++++++++++++++++++++++++++++++++++++++++++++++++++++++++++++++++++++++ 7440
ACGGCGTTTTTTCCCTTATTCCCGCTGTGCCTTTACAACTTATGAGTATGAGAAGGAAAAAGTTATAATAACTTCGTAAA
 Ala Ala Phe Phe Pro Ile Leu Ala Val Arg Phe His Gln Ile Ser Met
                         b-Lactamase
```

BspHI

```
ATCAGGGTTATTGTCTCATGAGCGGATACATATTTGAATGTATTTAGAAAAATAAACAAATAGGGGTTCCGCGCACATTT
++++++++++++++++++++++++++++++++++++++++++++++++++++++++++++++++++++++++++++++++ 7520
TAGTCCCAATAACAGAGTACTCGCCTATGTATAAACTTACATAAATCTTTTTATTTGTTTATCCCCAAGGCGCGTGTAAA
```

BspHI

```
CCCCGAAAAGTGCCACCTGACGTCTAAGAAACCATTATTATCATGACATTAACCTATAAAAATAGGCGTATCACGAGGCC
++++++++++++++++++++++++++++++++++++++++++++++++++++++++++++++++++++++++++++++++ 7600
GGGGCTTTTCACGGTGGACTGCAGATTCTTTGGTAATAATAGTACTGTAATTGGATATTTTTATCCGCATAGTGCTCCGG
```

```
CTTTCGTCTTCAAGAAT
+++++++++++++++++> 7617
GAAAGCAGAAGTTCTTA
```

Wednesday, January 23, 2002 3:33 PM
p-GD1719 pLBC-M4HCF.MPD (1 > 7626)   Site and Sequence
Enzymes : 36 of 538 enzymes (Filtered)
Settings :       Circular, Certain Sites Only, Standard Genetic Code        FIG. 6 (part 1 of 16)

```
GAATTAATTCATACCAGATCACCGAAAACTGTCCTCCAAATGTGTCCCCCTCACACTCCCAAATTCGCGGGCTT
                                                                              74
CTTAATTAAGTATGGTCTAGTGGCTTTTGACAGGAGGTTTACACAGGGGGAGTGTGAGGGTTTAAGCGCCCGAA
```

SacII
```
CTGCCTCTTAGACCACTCTACCCTATTCCCCACACTCACCGGAGCCAAAGCCGCGGCCCTTCCGTTTCTTTGCT
                                                                              148
GACGGAGAATCTGGTGAGATGGGATAAGGGGTGTGAGTGGCCTCGGTTTCGGCGCCGGGAAGGCAAAGAAACGA
```

NheI
```
TTTGAAAGACCCCACCCGTAGGTGGCAAGCTAGCTTAAGTAACGCCACTTTGCAAGGCATGGAAAAATACATAA
                                                                              222
AAACTTTCTGGGGTGGGCATCCACCGTTCGATCGAATTCATTGCGGTGAAACGTTCCGTACCTTTTTATGTATT
```
                                     5' LTR

PvuII              EcoRV
```
CTGAGAATAGAAAAGTTCAGATCAAGGTCAGGAACAAAGAAACAGCTGAATACCAAACAGGATATCTGTGGTAA
                                                                              296
GACTCTTATCTTTTCAAGTCTAGTTCCAGTCCTTGTTTCTTTGTCGACTTATGGTTTGTCCTATAGACACCATT
```
                                     5' LTR

PvuII              EcoRV
```
GCGGTTCCTGCCCCGGCTCAGGGCCAAGAACAGATGAGACAGCTGAGTGATGGGCCAAACAGGATATCTGTGGT
                                                                              370
CGCCAAGGACGGGGCCGAGTCCCGGTTCTTGTCTACTCTGTCGACTCACTACCCGGTTTGTCCTATAGACACCA
```
                                     5' LTR

```
AAGCAGTTCCTGCCCCGGCTCGGGGCCAAGAACAGATGGTCCCCAGATGCGGTCCAGCCCTCAGCAGTTTCTAG
                                                                              444
TTCGTCAAGGACGGGGCCGAGCCCCGGTTCTTGTCTACCAGGGGTCTACGCCAGGTCGGGAGTCGTCAAAGATC
```
                                     5' LTR

Wednesday, January 23, 2002 3:33 PM
p-GD1719 pLBC-M4HCF.MPD (1 > 7626) Site and Sequence     FIG. 6 (part 2 of 16)

```
TGAATCATCAGATGTTTCCAGGGTGCCCCAAGGACCTGAAAATGACCCTGTACCTTATTTGAACTAACCAATCA
ACTTAGTAGTCTACAAAGGTCCCACGGGGTTCCTGGACTTTTACTGGGACATGGAATAAACTTGATTGGTTAGT   518
```
──────── 5' LTR ────────

```
                                    SacI                              AscI
GTTCGCTTCTCGCTTCTGTTCGCGCGCTTCCGCTCTCCGAGCTCAATAAAAGAGCCCACAACCCCTCACTCGGC
CAAGCGAAGAGCGAAGACAAGCGCGCGAAGGCGAGAGGCTCGAGTTATTTTCTCGGGTGTTGGGGAGTGAGCCG   592
```
──────── 5' LTR ────────

```
              SmaI  KpnI
GCGCCAGTCTTCCGATAGACTGCGTCGCCCGGGTACCCGTATTCCCAATAAAGCCTCTTGCTGTTTGCATCCGA
CGCGGTCAGAAGGCTATCTGACGCAGCGGGCCCATGGGCATAAGGGTTATTTCGGAGAACGACAAACGTAGGCT   666
```
──────── 5' LTR ────────

```
ATCGTGGTCTCGCTGTTCCTTGGGAGGGTCTCCTCTGAGTGATTGACTACCCACGACGGGGGTCTTTCATTTGG
TAGCACCAGAGCGACAAGGAACCCTCCCAGAGGAGACTCACTAACTGATGGGTGCTGCCCCCAGAAAGTAAACC   740
```
──────── 5' LTR ────────

```
GGGCTCGTCCGGGATTTGGAGACCCCTGCCCAGGGACCACCGACCCACCACCGGGAGGTAAGCTGGCCAGCAAC
CCCGAGCAGGCCCTAAACCTCTGGGGACGGGTCCCTGGTGGCTGGGTGGTGGCCCTCCATTCGACCGGTCGTTG   814
```
                                                                    └Extende-

```
                                   SpeI
TTATCTGTGTCTGTCCGATTGTCTAGTGTCTATGTTTGATGTTATGCGCCTGCGTCTGTACTAGTTAGCTAACT
AATAGACACAGACAGGCTAACAGATCACAGATACAAACTACAATACGCGGACGCAGACATGATCAATCGATTGA   888
```
──────── Extended Packaging Region ────────

Wednesday, January 23, 2002 3:33 PM
p-GD1719 pLBC-M4HCF.MPD (1 > 7626) Site and Sequence        FIG. 6 (part 3 of 16)

```
AGCTCTGTATCTGGCGGACCCGTGGTGGAACTGACGAGTTCTGAACACCCGGCCGCAACCCTGGGAGACGTCCC
                                                                           962
TCGAGACATAGACCGCCTGGGCACCACCTTGACTGCTCAAGACTTGTGGGCCGGCGTTGGGACCCTCTGCAGGG
```
——————————————— Extended Packaging Region ———————————————

```
AGGGACTTTGGGGGCCGTTTTTGTGGCCCGACCTGACGAAGGGAGTCGATGTGGAATCCGACCCCGTCAGGATA
                                                                           1036
TCCCTGAAACCCCCGGCAAAAACACCGGGCTGGACTCCTTCCCTCAGCTACACCTTAGGCTGGGGCAGTCCTAT
```
——————————————— Extended Packaging Region ———————————————

```
TGTGGTTCTGGTAGGAGACGAGAACCTAAAACAGTTCCCGCCTCCGTCTGAATTTTTGCTTTCGGTTTGGAACC
                                                                           1110
ACACCAAGACCATCCTCTGCTCTTGGATTTTGTCAAGGGCGGAGGCAGACTTAAAAACGAAAGCCAAACCTTGG
```
——————————————— Extended Packaging Region ———————————————

PstI   PstI
```
GAAGCCGCGCGTCTTGTCTGCTGCAGCGCTGCAGCATCGTTCTGTGTTGTCTCTGTCTGACTGTGTTTCTGTAT
                                                                           1184
CTTCGGCGCGCAGAACAGACGACGTCGCGACGTCGTAGCAAGACACAACAGAGACAGACTGACACAAAGACATA
```
——————————————— Extended Packaging Region ———————————————

```
TTGTCTGAAAATTAGGGCCAGACTGTTACCACTCCCTTAAGTTTGACCTTAGGTCACTGGAAAGATGTCGAGCG
                                                                           1258
AACAGACTTTTAATCCCGGTCTGACAATGGTGAGGGAATTCAAACTGGAATCCAGTGACCTTTCTACAGCTCGC
```
——————————————— Extended Packaging Region ———————————————

PstI
```
GATCGCTCACAACCAGTCGGTAGATGTCAAGAAGAGACGTTGGGTTACCTTCTGCTCTGCAGAATGGCCAACCT
                                                                           1332
CTAGCGAGTGTTGGTCAGCCATCTACAGTTCTTCTCTGCAACCCAATGGAAGACGAGACGTCTTACCGGTTGGA
```
——————————————— Extended Packaging Region ———————————————

Wednesday, January 23, 2002 3:33 PM
p-GD1719 pLBC-M4HCF.MPD (1 > 7626) Site and Sequence FIG. 6 (part 4 of 16)

```
TTAACGTCGGATGGCCGCGAGACGGCACCTTTAACCGAGACCTCATCACCCAGGTTAAGATCAAGGTCTTTTCA
AATTGCAGCCTACCGGCGCTCTGCCGTGGAAATTGGCTCTGGAGTAGTGGGTCCAATTCTAGTTCCAGAAAAGT
```
1406

——— Extended Packaging Region ———

```
CCTGGCCCGCATGGACACCCAGACCAGGTCCCCTACATCGTGACCTGGGAAGCCTTGGCTTTTGACCCCCCTCC
GGACCGGGCGTACCTGTGGGTCTGGTCCAGGGGATGTAGCACTGGACCCTTCGGAACCGAAAACTGGGGGGAGG
```
1480

——— Extended Packaging Region ———

```
CTGGGTCAAGCCCTTTGTACACCCTAAGCCTCCGCCTCCTCTTCCTCCATCCGCCCCGTCTCTCCCCCTTGAAC
GACCCAGTTCGGGAAACATGTGGGATTCGGAGGCGGAGGAGAAGGAGGTAGGCGGGGCAGAGAGGGGGAACTTG
```
1554

——— Extended Packaging Region ———

Narl  EcoRI
```
CTCCTCGTTCGACCCCGCCTCGATCCTCCCTTTATCCAGCCCTCACTCCTTCTCTAGGCGCCGGAATTCCGATC
GAGGAGCAAGCTGGGGCGGAGCTAGGAGGGAAATAGGTCGGGAGTGAGGAAGAGATCCGCGGCCTTAAGGCTAG
```
1628

——— Extended Packaging Region ———

Bcll                                        Bcll
```
TGATCAAGAGACAGGATGAGGGAGCTTGTATATCCATTTTCGGATCTGATCAGCACGTGTTGACAATTAATCAT
ACTAGTTCTCTGTCCTACTCCCTCGAACATATAGGTAAAAGCCTAGACTAGTCGTGCACAACTGTTAATTAGTA
```
1702

——— EM7 Promoter ———

Ncol
```
CGGCATAGTATATCGGCATAGTATAATACGACAAGGTGAGGAACTAAACCATGGCCAAGCCTTTGTCTCAAGAA
GCCGTATCATATAGCCGTATCATATTATGCTGTTCCACTCCTTGATTTGGTACCGGTTCGGAAACAGAGTTCTT
```
1776

——— EM7 Promoter ———  Met Ala Lys Pro Leu Ser Gln Glu
——— Blast ———

Wednesday, January 23, 2002 3:33 PM
p-GD1719 pLBC-M4HCF.MPD (1 > 7626)  Site and Sequence FIG. 6 (part 5 of 16)

```
GAATCCACCCTCATTGAAAGAGCAACGGCTACAATCAACAGCATCCCCATCTCTGAAGACTACAGCGTCGCCAG
+--+--+--+--+--+--+--+--+--+--+--+--+--+--+--+--+--+--+--+--+--+--+--+--+  1850
CTTAGGTGGGAGTAACTTTCTCGTTGCCGATGTTAGTTGTCGTAGGGGTAGAGACTTCTGATGTCGCAGCGGTC
 Glu Ser Thr Leu Ile Glu Arg Ala Thr Ala Thr Ile Asn Ser Ile Pro Ile Ser Glu Asp Tyr Ser Val Ala Ser
                                        Blast
```

```
CGCAGCTCTCTCTAGCGACGGCCGCATCTTCACTGGTGTCAATGTATATCATTTTACTGGGGGACCTTGTGCAG
+--+--+--+--+--+--+--+--+--+--+--+--+--+--+--+--+--+--+--+--+--+--+--+--+  1924
GCGTCGAGAGAGATCGCTGCCGGCGTAGAAGTGACCACAGTTACATATAGTAAAATGACCCCCTGGAACACGTC
  Ala Ala Leu Ser Ser Asp Gly Arg Ile Phe Thr Gly Val Asn Val Tyr His Phe Thr Gly Gly Pro Cys Ala
                                        Blast
```

```
                                  PvuII                          NruI PvuI
                                    |                              |   |
AACTCGTGGTGCTGGGCACTGCTGCTGCTGCGGCAGCTGGCAACCTGACTTGTATCGTCGCGATCGGAAATGAG
+--+--+--+--+--+--+--+--+--+--+--+--+--+--+--+--+--+--+--+--+--+--+--+--+  1998
TTGAGCACCACGACCCGTGACGACGACGACGCCGTCGACCGTTGGACTGAACATAGCAGCGCTAGCCTTTACTC
 Glu Leu Val Val Leu Gly Thr Ala Ala Ala Ala Ala Gly Asn Leu Thr Cys Ile Val Ala Ile Gly Asn Glu
                                        Blast
```

```
                      SalI
                        |
AACAGGGGCATCTTGAGCCCCTGCGGACGGTGTCGACAGGTGCTTCTCGATCTGCATCCTGGGATCAAAGCGAT
+--+--+--+--+--+--+--+--+--+--+--+--+--+--+--+--+--+--+--+--+--+--+--+--+  2072
TTGTCCCCGTAGAACTCGGGGACGCCTGCCACAGCTGTCCACGAAGAGCTAGACGTAGGACCCTAGTTTCGCTA
 Asn Arg Gly Ile Leu Ser Pro Cys Gly Arg Cys Arg Gln Val Leu Leu Asp Leu His Pro Gly Ile Lys Ala Ile
                                        Blast
```

```
AGTGAAGGACAGTGATGGACAGCCGACGGCAGTTGGGATTCGTGAATTGCTGCCCTCTGGTTATGTGTGGGAGG
+--+--+--+--+--+--+--+--+--+--+--+--+--+--+--+--+--+--+--+--+--+--+--+--+  2146
TCACTTCCTGTCACTACCTGTCGGCTGCCGTCAACCCTAAGCACTTAACGACGGGAGACCAATACACACCCTCC
  Val Lys Asp Ser Asp Gly Gln Pro Thr Ala Val Gly Ile Arg Glu Leu Leu Pro Ser Gly Tyr Val Trp Glu
                                        Blast
```

```
GCTAAGCACTTCGTGGCCGAGGAGCAGGACTGACACGTGCTACGAGATTTCGATTCCACCGCCGCCTTCTATGA
+--+--+--+--+--+--+--+--+--+--+--+--+--+--+--+--+--+--+--+--+--+--+--+--+  2220
CGATTCGTGAAGCACCGGCTCCTCGTCCTGACTGTGCACGATGCTCTAAAGCTAAGGTGGCGGCGGAAGATACT
 Gly  •
  • Blast
```

```
AAGGTTGGGCTTCGGAATCGTTTTCCGGGACGCCGATCCGGCCATTAGCCATATTATTCATTGGTTATATAGCA
+--+--+--+--+--+--+--+--+--+--+--+--+--+--+--+--+--+--+--+--+--+--+--+--+  2294
TTCCAACCCGAAGCCTTAGCAAAAGGCCCTGCGGCTAGGCCGGTAATCGGTATAATAAGTAACCAATATATCGT
                                                    |―――――――――――――――――――
                                                              hCMV Promoter
```

Wednesday, January 23, 2002 3:33 PM
p-GD1719 pLBC-M4HCF.MPD (1 > 7626)   Site and Sequence          FIG. 6 (part 6 of 16)

```
TAAATCAATATTGGCTATTGGCCATTGCATACGTTGTATCCATATCATAATATGTACATTTATATTGGCTCATG
++++++++++++++++++++++++++++++++++++++++++++++++++++++++++++++++++++++++++  2368
ATTTAGTTATAACCGATAACCGGTAACGTATGCAACATAGGTATAGTATTATACATGTAAATATAACCGAGTAC
```
──────────────── hCMV Promoter ────────────────

SpeI
```
TCCAACATTACCGCCATGTTGACATTGATTATTGACTAGTTATTAATAGTAATCAATTACGGGGTCATTAGTTC
++++++++++++++++++++++++++++++++++++++++++++++++++++++++++++++++++++++++++  2442
AGGTTGTAATGGCGGTACAACTGTAACTAATAACTGATCAATAATTATCATTAGTTAATGCCCCAGTAATCAAG
```
──────────────── hCMV Promoter ────────────────

```
ATAGCCCATATATGGAGTTCCGCGTTACATAACTTACGGTAAATGGCCCGCCTGGCTGACCGCCCAACGACCCC
++++++++++++++++++++++++++++++++++++++++++++++++++++++++++++++++++++++++++  2516
TATCGGGTATATACCTCAAGGCGCAATGTATTGAATGCCATTTACCGGGCGGACCGACTGGCGGGTTGCTGGGG
```
──────────────── hCMV Promoter ────────────────

```
CGCCCATTGACGTCAATAATGACGTATGTTCCCATAGTAACGCCAATAGGGACTTTCCATTGACGTCAATGGGT
++++++++++++++++++++++++++++++++++++++++++++++++++++++++++++++++++++++++++  2590
GCGGGTAACTGCAGTTATTACTGCATACAAGGGTATCATTGCGGTTATCCCTGAAAGGTAACTGCAGTTACCCA
```
──────────────── hCMV Promoter ────────────────

NdeI
```
GGAGTATTTACGGTAAACTGCCCACTTGGCAGTACATCAAGTGTATCATATGCCAAGTACGCCCCCTATTGACG
++++++++++++++++++++++++++++++++++++++++++++++++++++++++++++++++++++++++++  2664
CCTCATAAATGCCATTTGACGGGTGAACCGTCATGTAGTTCACATAGTATACGGTTCATGCGGGGGATAACTGC
```
──────────────── hCMV Promoter ────────────────

```
TCAATGACGGTAAATGGCCCGCCTGGCATTATGCCCAGTACATGACCTTATGGGACTTTCCTACTTGGCAGTAC
++++++++++++++++++++++++++++++++++++++++++++++++++++++++++++++++++++++++++  2738
AGTTACTGCCATTTACCGGGCGGACCGTAATACGGGTCATGTACTGGAATACCCTGAAAGGATGAACCGTCATG
```
──────────────── hCMV Promoter ────────────────

Wednesday, January 23, 2002 3:33 PM
p-GD1719 pLBC-M4HCF.MPD (1 > 7626) Site and Sequence FIG. 6 (part 7 of 16)

```
                              NcoI
                              |
      ATCTACGTATTAGTCATCGCTATTACCATGGTGATGCGGTTTTGGCAGTACATCAATGGGCGTGGATAGCGGTT
                                                                                  2812
      TAGATGCATAATCAGTAGCGATAATGGTACCACTACGCCAAAACCGTCATGTAGTTACCCGCACCTATCGCCAA
      ═══════════════════════════════ hCMV Promoter ═══════════════════════════════

TGACTCACGGGGATTTCCAAGTCTCCACCCCATTGACGTCAATGGGAGTTTGTTTTGGCACCAAAATCAACGGG
                                                                                  2886
      ACTGAGTGCCCCTAAAGGTTCAGAGGTGGGGTAACTGCAGTTACCCTCAAACAAAACCGTGGTTTTAGTTGCCC
      ═══════════════════════════════ hCMV Promoter ═══════════════════════════════

ACTTTCCAAAATGTCGTAACAACTCCGCCCCATTGACGCAAATGGGCGGTAGGCATGTACGGTGGGAGGTCTAT
                                                                                  2960
      TGAAAGGTTTTACAGCATTGTTGAGGCGGGGTAACTGCGTTTACCCGCCATCCGTACATGCCACCCTCCAGATA
      ═══════════════════════════════ hCMV Promoter ═══════════════════════════════

SacI
                |
      ATAAGCAGAGCTCGTTTAGTGAACCGTCAGATCGCCTGGAGACGCCATCCACGCTGTTTTGACCTCCATAGAAG
                                                                                  3034
      TATTCGTCTCGAGCAAATCACTTGGCAGTCTAGCGGACCTCTGCGGTAGGTGCGACAAAACTGGAGGTATCTTC
      ═══════════════════════════════ hCMV Promoter ═══════════════════════════════

SacII    HindIII
                     |        |
      ACACCGGGACCGATCCAGCCTCCGCGGCCCCAAGCTTGTTATCACAAGTTTGTACAAAAAAGCAGGCTTCGAAG
                                                                                  3108
      TGTGGCCCTGGCTAGGTCGGAGGCGCCGGGGTTCGAACAATAGTGTTCAAACATGTTTTTTCGTCCGAAGCTTC
      ─────────── hCMV Promoter ──────────⟩     ┣━━━━━━━━━ attB1 ━━━━━━━━━┫

NcoI
                                        |
      GAGATAGAACCAATTCTCTAAGGAAATACTTAACCATGGGATGGAGCTGTATCATCCTCTTCTTGGTAGCAACA
                                                                                  3182
      CTCTATCTTGGTTAAGAGATTCCTTTATGAATTGGTACCCTACCTCGACATAGTAGGAGAAGAACCATCGTTGT
                                    Met Gly Trp Ser Cys Ile  Ile Leu Phe Leu Val Ala Thr
                                    ┗━━━━━━━━━━━━━━━ MN14 HCF ━━━━━━━━━━━━━━━
```

Wednesday, January 23, 2002 3:33 PM
p-GD1719 pLBC-M4HCF.MPD (1 > 7626)  Site and Sequence FIG. 6 (part 8 of 16)

```
GCTACAGGTGTCCACTCCGAGGTCCAACTGGTGGAGAGCGGTGGAGGTGTTGTGCAACCTGGCCGGTCCCTGCG
                                                                              3256
CGATGTCCACAGGTGAGGCTCCAGGTTGACCACCTCTCGCCACCTCCACAACACGTTGGACCGGCCAGGGACGC
 Ala Thr Gly Val His Ser Glu Val Gln Leu Val Glu Ser Gly Gly Val Val Gln Pro Gly Arg Ser Leu Arg
                                        MN14 HCF
```

```
CCTGTCCTGCTCCGCATCTGGCTTCGATTTCACCACATATTGGATGAGTTGGGTGAGACAGGCACCTGGAAAAG
                                                                              3330
GGACAGGACGAGGCGTAGACCGAAGCTAAAGTGGTGTATAACCTACTCAACCCACTCTGTCCGTGGACCTTTTC
 Leu Ser Cys Ser Ala Ser Gly Phe Asp Phe Thr Thr Tyr Trp Met Ser Trp Val Arg Gln Ala Pro Gly Lys
                                        MN14 HCF
```

```
GTCTTGAGTGGATTGGAGAAATTCATCCAGATAGCAGTACGATTAACTATGCGCCGTCTCTAAAGGATAGATTT
                                                                              3404
CAGAACTCACCTAACCTCTTTAAGTAGGTCTATCGTCATGCTAATTGATACGCGGCAGAGATTTCCTATCTAAA
 Gly Leu Glu Trp Ile Gly Glu Ile His Pro Asp Ser Ser Thr Ile Asn Tyr Ala Pro Ser Leu Lys Asp Arg Phe
                                        MN14 HCF
```

NruI

```
ACAATATCGCGAGACAACGCCAAGAACACATTGTTCCTGCAAATGGACAGCCTGAGACCCGAAGACACCGGGGT
                                                                              3478
TGTTATAGCGCTCTGTTGCGGTTCTTGTGTAACAAGGACGTTTACCTGTCGGACTCTGGGCTTCTGTGGCCCCA
 Thr Ile Ser Arg Asp Asn Ala Lys Asn Thr Leu Phe Leu Gln Met Asp Ser Leu Arg Pro Glu Asp Thr Gly Val
                                        MN14 HCF
```

```
CTATTTTTGTGCAAGCCTTTACTTCGGCTTCCCCTGGTTTGCTTATTGGGGCCAAGGGACCCCGGTCACCGTCT
                                                                              3552
GATAAAAACACGTTCGGAAATGAAGCCGAAGGGGACCAAACGAATAACCCCGGTTCCCTGGGGCCAGTGGCAGA
 Tyr Phe Cys Ala Ser Leu Tyr Phe Gly Phe Pro Trp Phe Ala Tyr Trp Gly Gln Gly Thr Pro Val Thr Val
                                        MN14 HCF
```

ApaI

```
CCTCAGCCTCCACCAAGGGCCCATCGGTCTTCCCCCTGGCACCCTCCTCCAAGAGCACCTCTGGGGGCACAGCG
                                                                              3626
GGAGTCGGAGGTGGTTCCCGGGTAGCCAGAAGGGGGACCGTGGGAGGAGGTTCTCGTGGAGACCCCCGTGTCGC
 Ser Ser Ala Ser Thr Lys Gly Pro Ser Val Phe Pro Leu Ala Pro Ser Ser Lys Ser Thr Ser Gly Gly Thr Ala
                                        MN14 HCF
```

Wednesday, January 23, 2002 3:33 PM
p-GD1719 pLBC-M4HCF.MPD (1 > 7626) Site and Sequence FIG. 6 (part 9 of 16)

```
                                                                NarI
GCCCTGGGCTGCCTGGTCAAGGACTACTTCCCCGAACCGGTGACGGTGTCGTGGAACTCAGGCGCCCTGACCAG
                                                                             3700
CGGGACCCGACGGACCAGTTCCTGATGAAGGGGCTTGGCCACTGCCACAGCACCTTGAGTCCGCGGGACTGGTC
 Ala Leu Gly Cys Leu Val Lys Asp Tyr Phe Pro Glu Pro Val Thr Val Ser Trp Asn Ser Gly Ala Leu Thr Ser
                                        MN14 HCF

CGGCGTGCACACCTTCCCGGCTGTCCTACAGTCCTCAGGACTCTACTCCCTCAGCAGCGTGGTGACCGTGCCCT
                                                                             3774
GCCGCACGTGTGGAAGGGCCGACAGGATGTCAGGAGTCCTGAGATGAGGGAGTCGTCGCACCACTGGCACGGGA
  Gly Val His Thr Phe Pro Ala Val Leu Gln Ser Ser Gly Leu Tyr Ser Leu Ser Ser Val Val Thr Val Pro
                                        MN14 HCF

CCAGCAGCTTGGGCACCCAGACCTACATCTGCAACGTGAATCACAAGCCCAGCAACACCAAGGTGGACAAGAGA
                                                                             3848
GGTCGTCGAACCCGTGGGTCTGGATGTAGACGTTGCACTTAGTGTTCGGGTCGTTGTGGTTCCACCTGTTCTCT
 Ser Ser Ser Leu Gly Thr Gln Thr Tyr Ile Cys Asn Val Asn His Lys Pro Ser Asn Thr Lys Val Asp Lys Arg
                                        MN14 HCF

GTTGAGCCCAAATCTTGTGACAAAACTCACACATGCCCACCGTGCCCAGCACCTGAACTCCTGGGGGGACCGTC
                                                                             3922
CAACTCGGGTTTAGAACACTGTTTTGAGTGTGTACGGGTGGCACGGGTCGTGGACTTGAGGACCCCCCTGGCAG
 Val Glu Pro Lys Ser Cys Asp Lys Thr His Thr Cys Pro Pro Cys Pro Ala Pro Glu Leu Leu Gly Gly Pro Ser
                                        MN14 HCF

BspHI
AGTCTTCCTCTTCCCCCCAAAACCCAAGGACACCCTCATGATCTCCCGGACCCCTGAGGTCACATGCGTGGTGG
                                                                             3996
TCAGAAGGAGAAGGGGGGTTTTGGGTTCCTGTGGGAGTACTAGAGGGCCTGGGGACTCCAGTGTACGCACCACC
  Val Phe Leu Phe Pro Pro Lys Pro Lys Asp Thr Leu Met Ile Ser Arg Thr Pro Glu Val Thr Cys Val Val
                                        MN14 HCF

TGGACGTGAGCCACGAAGACCCTGAGGTCAAGTTCAACTGGTACGTGGACGGCGTGGAGGTGCATAATGCCAAG
                                                                             4070
ACCTGCACTCGGTGCTTCTGGGACTCCAGTTCAAGTTGACCATGCACCTGCCGCACCTCCACGTATTACGGTTC
 Val Asp Val Ser His Glu Asp Pro Glu Val Lys Phe Asn Trp Tyr Val Asp Gly Val Glu Val His Asn Ala Lys
                                        MN14 HCF
```

Wednesday, January 23, 2002 3:33 PM  FIG. 6 (part 10 of 16)
p-GD1719 pLBC-M4HCF.MPD (1 > 7626)  Site and Sequence SacII ACAAAGCCGCGGGAGGAGCAGTACAACAGCACGTACCGTGTGGTCAGCGTCCTCACCGTCCTGCACCAGGACTG
TGTTTCGGCGCCCTCCTCGTCATGTTGTCGTGCATGGCACACCAGTCGCAGGAGTGGCAGGACGTGGTCCTGAC     4144
 Thr Lys Pro Arg Glu Glu Gln Tyr Asn Ser Thr Tyr Arg Val Val Ser Val Leu Thr Val Leu His Gln Asp Trp
———————————————————— MN14 HCF ————————————————————

GCTGAATGGCAAGGAGTACAAGTGCAAGGTCTCCAACAAAGCCCTCCCAGCCCCCATCGAGAAAACCATCTCCA
CGACTTACCGTTCCTCATGTTCACGTTCCAGAGGTTGTTTCGGGAGGGTCGGGGGTAGCTCTTTTGGTAGAGGT     4218
 Leu Asn Gly Lys Glu Tyr Lys Cys Lys Val Ser Asn Lys Ala Leu Pro Ala Pro Ile Glu Lys Thr Ile Ser
———————————————————— MN14 HCF ————————————————————

SmaI

AAGCCAAAGGGCAGCCCCGAGAACCACAGGTGTACACCCTGCCCCCATCCCGGGAGGAGATGACCAAGAACCAG
TTCGGTTTCCCGTCGGGGCTCTTGGTGTCCACATGTGGGACGGGGGTAGGGCCCTCCTCTACTGGTTCTTGGTC     4292
 Lys Ala Lys Gly Gln Pro Arg Glu Pro Gln Val Tyr Thr Leu Pro Pro Ser Arg Glu Glu Met Thr Lys Asn Gln
———————————————————— MN14 HCF ————————————————————

GTCAGCCTGACCTGCCTGGTCAAAGGCTTCTATCCCAGCGACATCGCCGTGGAGTGGGAGAGCAATGGGCAGCC
CAGTCGGACTGGACGGACCAGTTTCCGAAGATAGGGTCGCTGTAGCGGCACCTCACCCTCTCGTTACCCGTCGG     4366
 Val Ser Leu Thr Cys Leu Val Lys Gly Phe Tyr Pro Ser Asp Ile Ala Val Glu Trp Glu Ser Asn Gly Gln Pro
———————————————————— MN14 HCF ————————————————————

GGAGAACAACTACAAGACCACGCCTCCCGTGCTGGACTCCGACGGCTCCTTCTTCCTCTATAGCAAGCTCACCG
CCTCTTGTTGATGTTCTGGTGCGGAGGGCACGACCTGAGGCTGCCGAGGAAGAAGGAGATATCGTTCGAGTGGC     4440
 Glu Asn Asn Tyr Lys Thr Thr Pro Pro Val Leu Asp Ser Asp Gly Ser Phe Phe Leu Tyr Ser Lys Leu Thr
———————————————————— MN14 HCF ————————————————————

TGGACAAGAGCAGGTGGCAGCAGGGGAACGTCTTCTCATGCTCCGTGATGCACGAGGCTCTGCACAACCACTAC
ACCTGTTCTCGTCCACCGTCGTCCCCTTGCAGAAGAGTACGAGGCACTACGTGCTCCGAGACGTGTTGGTGATG     4514
 Val Asp Lys Ser Arg Trp Gln Gln Gly Asn Val Phe Ser Cys Ser Val Met His Glu Ala Leu His Asn His Tyr
———————————————————— MN14 HCF ————————————————————

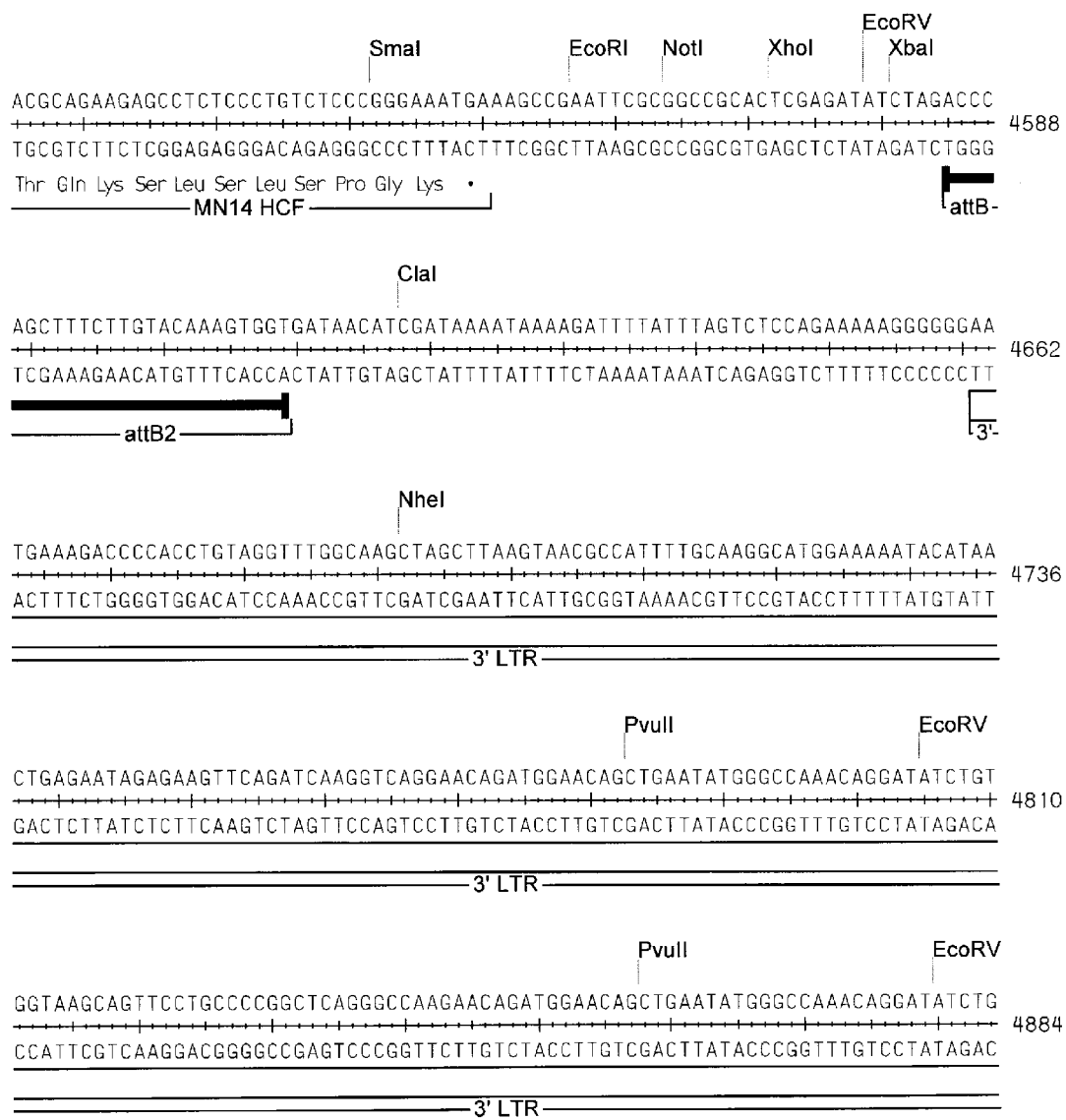
FIG. 6 (part 11 of 16)

Wednesday, January 23, 2002 3:33 PM
p-GD1719 pLBC-M4HCF.MPD (1 > 7626)   Site and Sequence     FIG. 6 (part 12 of 16)

```
                                                                    XbaI
TGGTAAGCAGTTCCTGCCCCGGCTCAGGGCCAAGAACAGATGGTCCCCAGATGCGGTCCAGCCCTCAGCAGTTT
                                                                           4958
ACCATTCGTCAAGGACGGGGCCGAGTCCCGGTTCTTGTCTACCAGGGGTCTACGCCAGGTCGGGAGTCGTCAAA
                                     3' LTR

CTAGAGAACCATCAGATGTTTCCAGGGTGCCCCAAGGACCTGAAATGACCCTGTGCCTTATTTGAACTAACCAA
                                                                           5032
GATCTCTTGGTAGTCTACAAAGGTCCCACGGGGTTCCTGGACTTTACTGGGACACGGAATAAACTTGATTGGTT

3' LTR

SacI
TCAGTTCGCTTCTCGCTTCTGTTCGCGCGCTTCTGCTCCCCGAGCTCAATAAAAGAGCCCACAACCCCTCACTC
                                                                           5106
AGTCAAGCGAAGAGCGAAGACAAGCGCGCGAAGACGAGGGGCTCGAGTTATTTTCTCGGGTGTTGGGGAGTGAG

3' LTR

NarI                               SmaI  KpnI
GGGGCGCCAGTCCTCCGATTGACTGAGTCGCCCGGGTACCCGTGTATCCAATAAACCCTCTTGCAGTTGCATCC
                                                                           5180
CCCCGCGGTCAGGAGGCTAACTGACTCAGCGGGCCCATGGGCACATAGGTTATTTGGGAGAACGTCAACGTAGG

3' LTR

GACTTGTGGTCTCGCTGTTCCTTGGGAGGGTCTCCTCTGAGTGATTGACTACCCGTCAGCGGGGGTCTTTCATT
                                                                           5254
CTGAACACCAGAGCGACAAGGAACCCTCCCAGAGGAGACTCACTAACTGATGGGCAGTCGCCCCCAGAAAGTAA

3' LTR

TTTCCATTGGGGGCTCGTCCGGGATCGGGAGACCCCTGCCCAGGGACCACCGACCCACCACCGGGAGGTAAGCT
                                                                           5328
AAAGGTAACCCCCGAGCAGGCCCTAGCCCTCTGGGGACGGGTCCCTGGTGGCTGGGTGGTGGCCCTCCATTCGA

GGCTGCCTCGCGCGTTTCGGTGATGACGGTGAAAACCTCTGACACATGCAGCTCCCGGAGACGGTCACAGCTTG
                                                                           5402
CCGACGGAGCGCGCAAAGCCACTACTGCCACTTTTGGAGACTGTGTACGTCGAGGGCCTCTGCCAGTGTCGAAC
```

FIG. 6 (part 13 of 16)

```
TCTGTAAGCGGATGCCGGGAGCAGACAAGCCCGTCAGGGCGCGTCAGCGGGTGTTGGCGGGTGTCGGGGCGCAG
AGACATTCGCCTACGGCCCTCGTCTGTTCGGGCAGTCCCGCGCAGTCGCCCACAACCGCCCACAGCCCCGCGTC
```
5476

```
CCATGACCCAGTCACGTAGCGATAGCGGAGTGTATACTGGCTTAACTATGCGGCATCAGAGCAGATTGTACTGA
GGTACTGGGTCAGTGCATCGCTATCGCCTCACATATGACCGAATTGATACGCCGTAGTCTCGTCTAACATGACT
```
5550

Ndel

```
GAGTGCACCATATGCGGTGTGAAATACCGCACAGATGCGTAAGGAGAAAATACCGCATCAGGCGCTCTTCCGCT
CTCACGTGGTATACGCCACACTTTATGGCGTGTCTACGCATTCCTCTTTTATGGCGTAGTCCGCGAGAAGGCGA
```
5624

```
TCCTCGCTCACTGACTCGCTGCGCTCGGTCGTTCGGCTGCGGCGAGCGGTATCAGCTCACTCAAAGGCGGTAAT
AGGAGCGAGTGACTGAGCGACGCGAGCCAGCAAGCCGACGCCGCTCGCCATAGTCGAGTGAGTTTCCGCCATTA
```
5698

```
ACGGTTATCCACAGAATCAGGGGATAACGCAGGAAAGAACATGTGAGCAAAAGGCCAGCAAAAGGCCAGGAACC
TGCCAATAGGTGTCTTAGTCCCCTATTGCGTCCTTTCTTGTACACTCGTTTTCCGGTCGTTTTCCGGTCCTTGG
```
5772

```
GTAAAAAGGCCGCGTTGCTGGCGTTTTTCCATAGGCTCCGCCCCCCTGACGAGCATCACAAAAATCGACGCTCA
CATTTTTCCGGCGCAACGACCGCAAAAAGGTATCCGAGGCGGGGGGACTGCTCGTAGTGTTTTTAGCTGCGAGT
```
5846

```
AGTCAGAGGTGGCGAAACCCGACAGGACTATAAAGATACCAGGCGTTTCCCCCTGGAAGCTCCCTCGTGCGCTC
TCAGTCTCCACCGCTTTGGGCTGTCCTGATATTTCTATGGTCCGCAAAGGGGGACCTTCGAGGGAGCACGCGAG
```
5920

```
TCCTGTTCCGACCCTGCCGCTTACCGGATACCTGTCCGCCTTTCTCCCTTCGGGAAGCGTGGCGCTTTCTCATA
AGGACAAGGCTGGGACGGCGAATGGCCTATGGACAGGCGGAAAGAGGGAAGCCCTTCGCACCGCGAAAGAGTAT
```
5994

```
GCTCACGCTGTAGGTATCTCAGTTCGGTGTAGGTCGTTCGCTCCAAGCTGGGCTGTGTGCACGAACCCCCCGTT
CGAGTGCGACATCCATAGAGTCAAGCCACATCCAGCAAGCGAGGTTCGACCCGACACACGTGCTTGGGGGGCAA
```
6068

```
CAGCCCGACCGCTGCGCCTTATCCGGTAACTATCGTCTTGAGTCCAACCCGGTAAGACACGACTTATCGCCACT
GTCGGGCTGGCGACGCGGAATAGGCCATTGATAGCAGAACTCAGGTTGGGCCATTCTGTGCTGAATAGCGGTGA
```
6142

```
GGCAGCAGCCACTGGTAACAGGATTAGCAGAGCGAGGTATGTAGGCGGTGCTACAGAGTTCTTGAAGTGGTGGC
CCGTCGTCGGTGACCATTGTCCTAATCGTCTCGCTCCATACATCCGCCACGATGTCTCAAGAACTTCACCACCG
```
6216

Wednesday, January 23, 2002 3:33 PM
p-GD1719 pLBC-M4HCF.MPD (1 > 7626)  Site and Sequence         FIG. 6 (part 14 of 16)

```
CTAACTACGGCTACACTAGAAGGACAGTATTTGGTATCTGCGCTCTGCTGAAGCCAGTTACCTTCGGAAAAAGA
                                                                          6290
GATTGATGCCGATGTGATCTTCCTGTCATAAACCATAGACGCGAGACGACTTCGGTCAATGGAAGCCTTTTTCT

GTTGGTAGCTCTTGATCCGGCAAACAAACCACCGCTGGTAGCGGTGGTTTTTTTGTTTGCAAGCAGCAGATTAC
                                                                          6364
CAACCATCGAGAACTAGGCCGTTTGTTTGGTGGCGACCATCGCCACCAAAAAAACAAACGTTCGTCGTCTAATG

GCGCAGAAAAAAAGGATCTCAAGAAGATCCTTTGATCTTTTCTACGGGGTCTGACGCTCAGTGGAACGAAAACT
                                                                          6438
CGCGTCTTTTTTTCCTAGAGTTCTTCTAGGAAACTAGAAAAGATGCCCCAGACTGCGAGTCACCTTGCTTTTGA

BspHI                                          DraI
          |                                              |
CACGTTAAGGGATTTTGGTCATGAGATTATCAAAAAGGATCTTCACCTAGATCCTTTTAAATTAAAAATGAAGT
                                                                          6512
GTGCAATTCCCTAAAACCAGTACTCTAATAGTTTTTCCTAGAAGTGGATCTAGGAAAATTTAATTTTTACTTCA

DraI
   |
TTTAAATCAATCTAAAGTATATATGAGTAAACTTGGTCTGACAGTTACCAATGCTTAATCAGTGAGGCACCTAT
                                                                          6586
AAATTTAGTTAGATTTCATATATACTCATTTGAACCAGACTGTCAATGGTTACGAATTAGTCACTCCGTGGATA
                                              ·  Trp His Lys Ile Leu Ser Ala Gly Ile
                                              └──────── b-Lactamase ───────

CTCAGCGATCTGTCTATTTCGTTCATCCATAGTTGCCTGACTCCCCGTCGTGTAGATAACTACGATACGGGAGG
                                                                          6660
GAGTCGCTAGACAGATAAAGCAAGTAGGTATCAACGGACTGAGGGGCAGCACATCTATTGATGCTATGCCCTCC
Glu Ala Ile Gln Arg Asn Arg Glu Asp Met Thr Ala Gln Ser Gly Thr Thr Tyr Ile Val Val Ile Arg Ser Pro
─────────────────────────────────── b-Lactamase ───────────────────────────────────

GCTTACCATCTGGCCCCAGTGCTGCAATGATACCGCGAGACCCACGCTCACCGGCTCCAGATTTATCAGCAATA
                                                                          6734
CGAATGGTAGACCGGGGTCACGACGTTACTATGGCGCTCTGGGTGCGAGTGGCCGAGGTCTAAATAGTCGTTAT
Lys Gly Asp Pro Gly Leu Ala Ala Ile Ile Gly Arg Ser Arg Glu Gly Ala Gly Ser Lys Asp Ala Ile
──────────────────────────────── b-Lactamase ──────────────────────────

AACCAGCCAGCCGGAAGGGCCGAGCGCAGAAGTGGTCCTGCAACTTTATCCGCCTCCATCCAGTCTATTAATTG
                                                                          6808
TTGGTCGGTCGGCCTTCCCGGCTCGCGTCTTCACCAGGACGTTGAAATAGGCGGAGGTAGGTCAGATAATTAAC
Phe Trp Gly Ala Pro Leu Ala Ser Arg Leu Leu Pro Gly Ala Val Lys Asp Ala Glu Met Trp Asp Ile Leu Gln
─────────────────────────────── b-Lactamase ──────────────────────────────
```

Wednesday, January 23, 2002 3:33 PM
p-GD1719 pLBC-M4HCF.MPD (1 > 7626)   Site and Sequence          FIG. 6 (part 15 of 16)

```
                                                Fspl                           Pstl
                                                 |                              |
       TTGCCGGGAAGCTAGAGTAAGTAGTTCGCCAGTTAATAGTTTGCGCAACGTTGTTGCCATTGCTGCAGGCATCG
                                                                                        6882
       AACGGCCCTTCGATCTCATTCATCAAGCGGTCAATTATCAAACGCGTTGCAACAACGGTAACGACGTCCGTAGC
        Gln Arg Ser Ala Leu Thr Leu Leu Glu Gly Thr Leu Leu Lys Arg Leu Thr Thr Ala Met Ala Ala Pro Met Thr
                                               b-Lactamase TGGTGTCACGCTCGTCGTTTGGTATGGCTTCATTCAGCTCCGGTTCCCAACGATCAAGGCGAGTTACATGATCC
                                                                                        6956
       ACCACAGTGCGAGCAGCAAACCATACCGAAGTAAGTCGAGGCCAAGGGTTGCTAGTTCCGCTCAATGTACTAGG
         Thr Asp Arg Glu Asp Asn Pro Ile Ala Glu Asn Leu Glu Pro Glu Trp Arg Asp Leu Arg Thr Val His Asp
                                                b-Lactamase Pvul
                                                             |
       CCCATGTTGTGCAAAAAAGCGGTTAGCTCCTTCGGTCCTCCGATCGTTGTCAGAAGTAAGTTGGCCGCAGTGTT
                                                                                        7030
       GGGTACAACACGTTTTTTCGCCAATCGAGGAAGCCAGGAGGCTAGCAACAGTCTTCATTCAACCGGCGTCACAA
        Gly Met Asn His Leu Phe Ala Thr Leu Glu Lys Pro Gly Gly Ile Thr Thr Leu Leu Leu Asn Ala Ala Thr Asn
                                                b-Lactamase ATCACTCATGGTTATGGCAGCACTGCATAATTCTCTTACTGTCATGCCATCCGTAAGATGCTTTTCTGTGACTG
                                                                                        7104
       TAGTGAGTACCAATACCGTCGTGACGTATTAAGAGAATGACAGTACGGTAGGCATTCTACGAAAAGACACTGAC
        Asp Ser Met Thr Ile Ala Ala Ser Cys Leu Glu Arg Val Thr Met Gly Asp Thr Leu His Lys Glu Thr Val Pro
                                                b-Lactamase GTGAGTACTCAACCAAGTCATTCTGAGAATAGTGTATGCGGCGACCGAGTTGCTCTTGCCCGGCGTCAACACGG
                                                                                        7178
       CACTCATGAGTTGGTTCAGTAAGACTCTTATCACATACGCCGCTGGCTCAACGAGAACGGGCCGCAGTTGTGCC
          Ser Tyr Glu Val Leu Asp Asn Gln Ser Tyr His Ile Arg Arg Gly Leu Gln Glu Gln Gly Ala Asp Val Arg
                                                b-Lactamase Dral
                                     |
       GATAATACCGCGCCACATAGCAGAACTTTAAAAGTGCTCATCATTGGAAAACGTTCTTCGGGGCGAAAACTCTC
                                                                                        7252
       CTATTATGGCGCGGTGTATCGTCTTGAAATTTTCACGAGTAGTAACCTTTTGCAAGAAGCCCCGCTTTTGAGAG
        Ser Leu Val Ala Gly Cys Leu Leu Val Lys Phe Thr Ser Met Met Pro Phe Arg Glu Glu Pro Arg Phe Ser Glu
                                                b-Lactamase
```

Wednesday, January 23, 2002 3:33 PM
p-GD1719 pLBC-M4HCF.MPD (1 > 7626)   Site and Sequence

```
AAGGATCTTACCGCTGTTGAGATCCAGTTCGATGTAACCCACTCGTGCACCCAACTGATCTTCAGCATCTTTTA
                                                                            7326
TTCCTAGAATGGCGACAACTCTAGGTCAAGCTACATTGGGTGAGCACGTGGGTTGACTAGAAGTCGTAGAAAAT
 Leu Ile Lys Gly Ser Asn Leu Asp Leu Glu Ile Tyr Gly Val Arg Ala Gly Leu Gln Asp Glu Ala Asp Lys Val
                                     ———— b-Lactamase ————

CTTTCACCAGCGTTTCTGGGTGAGCAAAAACAGGAAGGCAAAATGCCGCAAAAAAGGGAATAAGGGCGACACGG
                                                                            7400
GAAAGTGGTCGCAAAGACCCACTCGTTTTTGTCCTTCCGTTTTACGGCGTTTTTTCCCTTATTCCCGCTGTGCC
 Lys Val Leu Thr Glu Pro His Ala Phe Val Pro Leu Cys Phe Ala Ala Phe Phe Pro Ile Leu Ala Val Arg
                                     ———— b-Lactamase ————

BspHI
AAATGTTGAATACTCATACTCTTCCTTTTTCAATATTATTGAAGCATTTATCAGGGTTATTGTCTCATGAGCGG
                                                                            7474
TTTACAACTTATGAGTATGAGAAGGAAAAAGTTATAATAACTTCGTAAATAGTCCCAATAACAGAGTACTCGCC
 Phe His Gln Ile Ser Met
  ——— b-Lactamase ———

ATACATATTTGAATGTATTTAGAAAAATAAACAAATAGGGGTTCCGCGCACATTTCCCCGAAAAGTGCCACCTG
                                                                            7548
TATGTATAAACTTACATAAATCTTTTATTTGTTTATCCCCAAGGCGCGTGTAAAGGGGCTTTTCACGGTGGAC

BspHI
ACGTCTAAGAAACCATTATTATCATGACATTAACCTATAAAAATAGGCGTATCACGAGGCCCTTTCGTCTTCAA
                                                                            7622
TGCAGATTCTTTGGTAATAATAGTACTGTAATTGGATATTTTTATCCGCATAGTGCTCCGGGAAAGCAGAAGTT

GAAT
        7626
CTTA
```

FIG. 6 (part 16 of 16)

Wednesday, January 23, 2002 4:07 PM
P-GD1915 pLNC-LCA Map.MPD (1 > 7490)  Site and Sequence
Enzymes : 35 of 538 enzymes (Filtered)
Settings :         Circular, Certain Sites Only, Standard Genetic Code FIG. 7 (part 1 of 12)

```
GAATTAATTCATACCAGATCACCGAAAACTGTCCTCCAAATGTGTCCCCCTCACACTCCCAAATTCGCGGGCTTCTGCCT
                                                                                  80
CTTAATTAAGTATGGTCTAGTGGCTTTTGACAGGAGGTTTACACAGGGGGAGTGTGAGGGTTTAAGCGCCCGAAGACGGA
```

SacII
```
CTTAGACCACTCTACCCTATTCCCCACACTCACCGGAGCCAAAGCCGCGGCCCTTCCGTTTCTTTGCTTTTGAAAGACCC
                                                                                  160
GAATCTGGTGAGATGGGATAAGGGGTGTGAGTGGCCTCCGTTTCGGCGCCGGGAAGGCAAAGAAACGAAAACTTTCTGGG
                                                              ┌──────────
                                                              │ 5' LTR
                                                              └5' LTR MoMSV─
```

Nhel
```
CACCCGTAGGTGGCAACCTAGCTTAAGTAACGCCACTTTGCAAGGCATGGAAAAATACATAACTGAGAATAGAAAAGTTC
                                                                                  240
GTGGGCATCCACCGTTCGATCGAATTCATTGCGGTGAAACGTTCCGTACCTTTTTATGTATTGACTCTTATCTTTTCAAG
──────────────────────────────────────────────────────────────────────────────
─────────────────────── 5' LTR ──────────────────────────────────────────────
────────────────── 5' LTR MoMSV ─────────────────────────────────────────────
```

EcoRV
```
AGATCAAGGTCAGGAACAAAGAAACAGCTGAATACCAAACAGGATATCTGTGGTAAGCGGTTCCTGCCCCGGCTCAGGGC
                                                                                  320
TCTAGTTCCAGTCCTTGTTTCTTTGTCGACTTATGGTTTGTCCTATAGACACCATTCGCCAAGGACGGGGCCGAGTCCCG
─────────────────────────────── 5' LTR ──────────────────────────────────────
────────────────────────── 5' LTR MoMSV ─────────────────────────────────────
```

EcoRV
```
CAAGAACAGATGAGACAGCTGAGTGATGGGCCAAACAGGATATCTGTGGTAAGCAGTTCCTGCCCCGGCTCGGGGCCAAG
                                                                                  400
GTTCTTGTCTACTCTGTCGACTCACTACCCGGTTTGTCCTATAGACACCATTCGTCAAGGACGGGGCCGAGCCCCGGTTC
─────────────────────────────── 5' LTR ──────────────────────────────────────
────────────────────────── 5' LTR MoMSV ─────────────────────────────────────
```

```
AACAGATGGTCCCCAGATGCGGTCCAGCCCTCAGCAGTTTCTAGTGAATCATCAGATGTTTCCAGGGTGCCCCAAGGACC
                                                                                  480
TTGTCTACCAGGGGTCTACGCCAGGTCGGGAGTCGTCAAAGATCACTTAGTAGTCTACAAAGGTCCCACGGGGTTCCTGG
─────────────────────────────── 5' LTR ──────────────────────────────────────
────────────────────────── 5' LTR MoMSV ─────────────────────────────────────
```

```
TGAAAATGACCCTGTACCTTATTTGAACTAACCAATCAGTTCGCTTCTCCCTTCTGTTCGCGCGCTTCCGCTCTCCGAGC
                                                                                  560
ACTTTTACTGGGACATGGAATAAACTTGATTGGTTAGTCAAGCGAAGAGCGAAGACAAGCGCGCGAAGGCGAGAGGCTCG
─────────────────────────────── 5' LTR ──────────────────────────────────────
────────────────────────── 5' LTR MoMSV ─────────────────────────────────────
```

Wednesday, January 23, 2002 4:07 PM
P-GD1915 pLNC-LCA Map.MPD (1 > 7490)  Site and Sequence FIG. 7 (part 2 of 12)

```
     SacI                            AscI                              SmaI  KpnI
     |                               |                                 |     |
     TCAATAAAAGAGCCCACAACCCCTCACTCGGCGCGCCAGTCTTCCGATAGACTGCGTCGCCCGGGTACCCGTATTCCCAA
     ++++++++++++++++++++++++++++++++++++++++++++++++++++++++++++++++++++++++++++++++ 640
     AGTTATTTTCTCGGGTGTTGGGGAGTGAGCCGCGCGGTCAGAAGGCTATCTGACGCAGCGGGCCCATGGGCATAAGGGTT
                                     5' LTR
     ━━━━━━━━━━━━━━━━━━━━━━━━━━━━━━ 5' LTR MoMSV ━━━━━━━━━━━━━━━━━━━━━━━━━━━━━━━━━━━━

TAAAGCCTCTTGCTGTTTGCATCCGAATCGTGGTCTCGCTGTTCCTTGGGAGGGTCTCCTCTGACTGATTGACTACCCAC
     ++++++++++++++++++++++++++++++++++++++++++++++++++++++++++++++++++++++++++++++++ 720
     ATTTCCGAGAACGACAAACGTAGGCTTAGCACCAGAGCGACAAGGAACCCTCCCAGAGGAGACTCACTAACTGATGGGTG
                                     5' LTR
     ━━━━━━━━━━━━━━━━━━━━━━━━━━━━━━ 5' LTR MoMSV ━━━━━━━━━━━━━━━━━━━━━━━━━━━━━━━━━━━━

GACGGGGGTCTTTCATTTGGGGGCTCGTCCGGGATTTGGAGACCCCTGCCCAGGGACCACCGACCCACCACCGGGACGTA
     ++++++++++++++++++++++++++++++++++++++++++++++++++++++++++++++++++++++++++++++++ 800
     CTGCCCCCAGAAAGTAAACCCCCGAGCAGGCCCTAAACCTCTGGGGACGGGTCCCTGGTGGCTCGGTGGTGGCCCTCCAT
     ━━━━━━ 5' LTR ━━━━━━▶
     ━━ 5' LTR MoMSV ━━┘

SpeI
                                                                        |
     AGCTGGCCAGCAACTTATCTGTGTCTGTCCGATTGTCTAGTGTCTATGTTTGATGTTATGCGCCTGCGTCTGTACTAGTT
     ++++++++++++++++++++++++++++++++++++++++++++++++++++++++++++++++++++++++++++++++ 880
     TCGACCGGTCGTTGAATAGACACAGACAGGCTAACAGATCACAGATACAAACTACAATACGCGGACGCAGACATGATCAA
     ┣━━━━━━━━━━━━━━━━━━━━━━━━━━━━━━━━ Pkg Rgn ━━━━━━━━━━━━━━━━━━━━━━━━━━━━━━━━━━━━
     ┗━━━━━━━━━━━━━━━━━━━━━━━━━━ Extended Packaging Region ━━━━━━━━━━━━━━━━━━━━━━━━━

AGCTAACTAGCTCTGTATCTGGCGGACCCGTGGTGGAACTGACGAGTTCTGAACACCCGGCCGCAACCCTGGGAGACGTC
     ++++++++++++++++++++++++++++++++++++++++++++++++++++++++++++++++++++++++++++++++ 960
     TCGATTGATCGAGACATAGACCGCCTGGGCACCACCTTGACTGCTCAAGACTTGTGGGCCGGCGTTGGGACCCTCTGCAG
     ━━━━━━━━━━━━━━━━━━━━━━━━━━━━━━━━━ Pkg Rgn ━━━━━━━━━━━━━━━━━━━━━━━━━━━━━━━━━━━
     ━━━━━━━━━━━━━━━━━━━━━━━━━━ Extended Packaging Region ━━━━━━━━━━━━━━━━━━━━━━━━━

CCAGGGACTTTGGGGGCCGTTTTTGTGGCCCGACCTGAGGAAGCCACTCGATGTGGAATCCGACCCCGTCAGGATATGTG
     ++++++++++++++++++++++++++++++++++++++++++++++++++++++++++++++++++++++++++++++++ 1040
     GGTCCCTGAAACCCCCGGCAAAAACACCGGGCTGGACTCCTTCCCTCAGCTACACCTTAGGCTGGGGCAGTCCTATACAC
     ━━━━━━━━━━━━━━━━━━━━━━━━━━━━━━━━━ Pkg Rgn ━━━━━━━━━━━━━━━━━━━━━━━━━━━━━━━━━━━
     ━━━━━━━━━━━━━━━━━━━━━━━━━━ Extended Packaging Region ━━━━━━━━━━━━━━━━━━━━━━━━━

GTTCTGGTAGGAGACGAGAACCTAAAACAGTTCCCGCCTCCGTCTGAATTTTTGCTTTCGGTTTGGAACCGAAGCCGCGC
     ++++++++++++++++++++++++++++++++++++++++++++++++++++++++++++++++++++++++++++++++ 1120
     CAAGACCATCCTCTGCTCTTGGATTTTGTCAAGGGCGGAGGCAGACTTAAAAACCAAAGCCAAACCTTGGCTTCGGCGCG
     ━━━━━━━━━━━━━━━━━━━━━━━━━━━━━━━━━ Pkg Rgn ━━━━━━━━━━━━━━━━━━━━━━━━━━━━━━━━━━━
     ━━━━━━━━━━━━━━━━━━━━━━━━━━ Extended Packaging Region ━━━━━━━━━━━━━━━━━━━━━━━━━

PstI    PstI
                    |       |
     GTCTTGTCTGCTGCAGCGCTGCAGCATCGTTCTGTGTTGTCTCTGTCTGACTGTGTTTCTGTATTTGTCTGAAAATTAGG
     ++++++++++++++++++++++++++++++++++++++++++++++++++++++++++++++++++++++++++++++++ 1200
     CAGAACAGACGACGTCGCGACGTCGTAGCAAGACACAACAGAGACAGACTGACACAAAGACATAAACAGACTTTTAATCC
     ━━━━━━━━━━━━━━━━━━━━━━━━━━━━━━━━━ Pkg Rgn ━━━━━━━━━━━━━━━━━━━━━━━━━━━━━━━━━━━
     ━━━━━━━━━━━━━━━━━━━━━━━━━━ Extended Packaging Region ━━━━━━━━━━━━━━━━━━━━━━━━━
```

FIG. 7 (part 3 of 12)

```
GCCAGACTGTTACCACTCCCTTAAGTTTGACCTTAGGTCACTGGAAAGATGTCGAGCGGATCGCTCACAACCAGTCGGTA
                                                                                  1280
CGGTCTGACAATGGTGAGGGAATTCAAACTGGAATCCAGTGACCTTTCTACAGCTCGCCTAGCGAGTGTTGGTCAGCCAT
                            ■ Pkg Rgn ■
                    Extended Packaging Region Pstl
GATGTCAAGAAGAGACGTTGGGTTACCTCTGCTCTGCAGAATGGCCAACCTTTAACGTCGGATGGCCGCGAGACGGCAC
                                                                                  1360
CTACAGTTCTTCTCTGCAACCCAATGGAAGACGAGACGTCTTACCGGTTGGAAATTGCAGCCTACCGGCGCTCTGCCGTG
                            ■ Pkg Rgn ■
                    Extended Packaging Region CTTTAACCGAGACCTCATCACCCAGGTTAAGATCAAGGTCTTTTCACCTGGCCCGCATGGACACCCAGACCAGGTCCCCT
                                                                                  1440
GAAATTGGCTCTGGAGTAGTGGGTCCAATTCTAGTTCCAGAAAAGTGGACCGGGCGTACCTGTGGGTCTGGTCCAGGGGA
                            ■ Pkg Rgn ■
                    Extended Packaging Region ACATCGTGACCTGGGAAGCCTTGGCTTTTGACCCCCCTCCCGGGTCAAGCCCTTTGTACACCCTAAGCCTCCGCCTCCT
                                                                                  1520
TGTAGCACTGGACCCTTCGGAACCGAAAACTGGGGGGAGGGACCCAGTTCGGGAAACATGTGGGATTCGGAGGCGGACGA
                            ■ Pkg Rgn ■
                    Extended Packaging Region CTTCCTCCATCCGCCCGTCTCTCCCCCTTGAACCTCCTCGTTCGACCCCGCCTCGATCCTCCCTTTATCCAGCCCTCAC
                                                                                  1600
GAAGGAGGTAGGCGGGCAGAGAGGGGGAACTTGGAGGAGCAAGCTGGGGCGGACCTACGAGCGAAATAGGTCGGGAGTG
                            ■ Pkg Rgn ■
                    Extended Packaging Region NarI    EcoRI   BclI
TCCTTCTCTAGGCGCCGGAATTCCGATCTGATCAAGAGACAGGATGAGGATCGTTTCGCATGATTGAACAAGATGGATTG
                                                                                  1680
AGGAAGAGATCCGCGGCCTTAAGGCTAGACTAGTTCTCTGTCCTACTCCTAGCAAAGCGTACTAACTTGTTCTACCTAAC
■ Pkg Rgn ■                                              Met Ile Glu Gln Asp Gly Leu
- Extended Packaging                                              Neo CACGCAGGTTCCCGGCCGCTTGGGTGGAGAGGCTATTCGGCTATGACTGGGCACAACAGACAATCGGCTGCTCTGATGC
                                                                                  1760
GTGCGTCCAAGAGGCCGGCGAACCCACCTCTCCGATAAGCCGATACTGACCCGTGTTGTCTGTTAGCCGACGAGACTACG
 His Ala Gly Ser Pro Ala Ala Trp Val Glu Arg Leu Phe Gly Tyr Asp Trp Ala Gln Gln Thr Ile Gly Cys Ser Asp Ala
                                            Neo NarI
CCCCGTCTTCCGGCTGTCAGCGCAGGGGCGCCCGGTTCTTTTTGTCAAGACCGACCTGTCCGGTGCCCTGAATGAACTGC
                                                                                  1840
GCGGCACAAGGCCGACAGTCGCGTCCCCGCGGGCCAAGAAAAACAGTTCTGGCTGGACAGGCCACGGGACTTACTTGACG
 Ala Val Phe Arg Leu Ser Ala Gln Gly Arg Pro Val Leu Phe Val Lys Thr Asp Leu Ser Gly Ala Leu Asn Glu Leu
                                            Neo
```

Wednesday, January 23, 2002 4:07 PM
P-GD1915 pLNC-LCA Map.MPD (1 > 7490) Site and Sequence FIG. 7 (part 4 of 12)

```
                PstI                                                    FspI
         AGGACGAGGCAGCGCGGCTATCGTGGCTGGCCACGACGGGCGTTCCTTGCGCAGCTGTGCTCGACGTTGTCACTGAAGCG
         ++++++++++|++++++++++|++++++++++|++++++++++|++++++++++|++++++++++|++++++++++|++++ 1920
         TCCTGCTCCGTCGCGCCGATAGCACCGACCGGTGCTGCCCGCAAGGAACGCGTCGACACGAGCTGCAACAGTGACTTCGC
          Gln Asp Glu Ala Ala Arg Leu Ser Trp Leu Ala Thr Thr Gly Val Pro Cys Ala Ala Val Leu Asp Val Val Thr Glu Ala
         ─────────────────────────────────────────── Neo ───────────────────────────────

GGAAGGGACTGGCTGCTATTGGGCGAAGTGCCGGGGCAGGATCTCCTGTCATCTCACCTTGCTCCTGCCGAGAAAGTATC
         ++++++++++|++++++++++|++++++++++|++++++++++|++++++++++|++++++++++|++++++++++|++++ 2000
         CCTTCCCTGACCGACGATAACCCGCTTCACGGCCCCGTCCTAGAGGACAGTAGAGTGGAACGAGGACGGCTCTTTCATAG
          Gly Arg Asp Trp Leu Leu Leu Gly Glu Val Pro Gly Gln Asp Leu Leu Ser Ser His Leu Ala Pro Ala Glu Lys Val Ser
         ─────────────────────────────────────────── Neo ───────────────────────────────

CATCATGGCTGATGCAATGCGGCGGCTGCATACGCTTGATCCGGCTACCTGCCCATTCGACCACCAAGCGAAACATCGCA
         ++++++++++|++++++++++|++++++++++|++++++++++|++++++++++|++++++++++|++++++++++|++++ 2080
         GTAGTACCGACTACGTTACGCCGCCGACGTATGCGAACTAGGCCGATGGACGGGTAAGCTGGTGGTTCGCTTTGTAGCGT
          Ile Met Ala Asp Ala Met Arg Arg Leu His Thr Leu Asp Pro Ala Thr Cys Pro Phe Asp His Gln Ala Lys His Arg
         ─────────────────────────────────────────── Neo ───────────────────────────────

TCGAGCGAGCACGTACTCGGATGGAAGCCGGTCTTGTCGATCAGGATGATCTGGACGAAGAGCATCAGGGGCTCGCGCCA
         ++++++++++|++++++++++|++++++++++|++++++++++|++++++++++|++++++++++|++++++++++|++++ 2160
         AGCTCGCTCGTGCATGAGCCTACCTTCGGCCAGAACAGCTAGTCCTACTAGACCTGCTTCTCGTAGTCCCCGAGCGCGGT
          Ile Glu Arg Ala Arg Thr Arg Met Glu Ala Gly Leu Val Asp Gln Asp Asp Leu Asp Glu Glu His Gln Gly Leu Ala Pro
         ─────────────────────────────────────────── Neo ───────────────────────────────

SphI                          NcoI
         GCCGAACTGTTCGCCAGGCTCAAGGCGCGCATGCCCGACGGCGAGGATCTCGTCGTGACCCATGGCGATGCCTGCTTGCC
         ++++++++++|++++++++++|++++++++++|++++++++++|++++++++++|++++++++++|++++++++++|++++ 2240
         CGGCTTGACAAGCGGTCCGAGTTCCGCGCGTACGGGCTGCCGCTCCTAGAGCAGCACTGGGTACCGCTACGGACGAACGG
          Ala Glu Leu Phe Ala Arg Leu Lys Ala Arg Met Pro Asp Gly Glu Asp Leu Val Val Thr His Gly Asp Ala Cys Leu Pro
         ─────────────────────────────────────────── Neo ───────────────────────────────

NaeI
         GAATATCATGGTGGAAAATGGCCGCTTTTCTGGATTCATCGACTGTGGCCGGCTGGGTGTGGCGGACCGCTATCAGGACA
         ++++++++++|++++++++++|++++++++++|++++++++++|++++++++++|++++++++++|++++++++++|++++ 2320
         CTTATAGTACCACCTTTTACCGGCGAAAAGACCTAAGTAGCTGACACCGGCCGACCCACACCGCCTGGCGATAGTCCTGT
          Asn Ile Met Val Glu Asn Gly Arg Phe Ser Gly Phe Ile Asp Cys Gly Arg Leu Gly Val Ala Asp Arg Tyr Gln Asp
         ─────────────────────────────────────────── Neo ───────────────────────────────

TAGCGTTGGCTACCCGTGATATTGCTGAAGAGCTTGGCGGCGAATGGGCTGACCGCTTCCTCGTGCTTTACGGTATCGCC
         ++++++++++|++++++++++|++++++++++|++++++++++|++++++++++|++++++++++|++++++++++|++++ 2400
         ATCGCAACCGATGGGCACTATAACGACTTCTCGAACCGCCGCTTACCCGACTGGCGAAGGAGCACGAAATGCCATAGCGG
          Ile Ala Leu Ala Thr Arg Asp Ile Ala Glu Glu Leu Gly Gly Glu Trp Ala Asp Arg Phe Leu Val Leu Tyr Gly Ile Ala
         ─────────────────────────────────────────── Neo ───────────────────────────────

GCTCCCGATTCGCAGCGCATCGCCTTCTATCGCCTTCTTGACGAGTTCTTCTGAGCGGGACTCTGGGGTTCGAAATGACC
         ++++++++++|++++++++++|++++++++++|++++++++++|++++++++++|++++++++++|++++++++++|++++ 2480
         CGAGGGCTAAGCGTCGCGTAGCGGAAGATAGCGGAAGAACTGCTCAAGAAGACTCGCCCTGAGACCCCAAGCTTTACTGG
          Ala Pro Asp Ser Gln Arg Ile Ala Phe Tyr Arg Leu Leu Asp Glu Phe Phe *
         ─────────────────────────────────── Neo ───────────────────────────
```

Wednesday, January 23, 2002 4:07 PM
P-GD1915 pLNC-LCA Map.MPD (1 > 7490) Site and Sequence FIG. 7 (part 5 of 12)

```
     GACCAAGCGACGCCCAACCTGCCATCACGAGATTTCGATTCCACCGCCGCCTTCTATGAAAGGTTGGGCTTCGGAATCGT
                                                                                      2560
     CTGGTTCGCTGCGGGTTGGACGGTAGTGCTCTAAAGCTAAGGTGGCGGCGGAAGATACTTTCCAACCCGAAGCCTTAGCA

Nael                                                  Smal
     TTTCCGGGACGCCGGCTGGATGATCCTCCAGCGCGGGGATCTCATGCTGGAGTTCTTCGCCCACCCCGGGCTCGATCCCC
                                                                                      2640
     AAAGGCCCTGCGGCCGACCTACTAGGAGGTCGCGCCCCTAGAGTACGACCTCAAGAAGCGGGTGGGGCCCGAGCTAGGGG Nrul
     TCGCGAGTTGGTTCAGCTGCTGCCTGAGGCTGGACGACCTCGCGGAGTTCTACCGGCAGTGCAAATCCGTCGGCATCCAG
                                                                                      2720
     AGCGCTCAACCAAGTCGACGACGGACTCCGACCTGCTGGAGCGCCTCAAGATGGCCGTCACGTTTAGGCAGCCGTAGGTC Pstl
     GAAACCAGCAGCGGCTATCCCCGCATCCATGCCCCCGAACTGCAGGAGTGGGGAGGCACGATGGCCGCTTTGGTCGACGC
                                                                                      2800
     CTTTGGTCGTCGCCGATAGGGCGTAGGTACGGGGGCTTGACGTCCTCACCCCTCCGTGCTACCGGCGAAACCAGCTGCG BamHI
     GGATCCGGCCATTAGCCATATTATTCATTGGTTATATAGCATAAATCAATATTGGCTATTGGCCATTGCATACGTTGTAT
                                                                                      2880
     CCTAGGCCGGTAATCGGTATAATAAGTAACCAATATATCGTATTTAGTTATAACCGATAACCGGTAACGTATGCAACATA
     ───────────────────────────────CMV Pro─────────────────────────────────
     ─────────────────────────────hCMV Promoter───────────────────────────────

Spel
     CCATATCATAATATGTACATTTATATTGGCTCATGTCCAACATTACCGCCATGTTGACATTCATTATTCACTAGTTATTA
                                                                                      2960
     GGTATAGTATTATACATGTAAATATAACCGAGTACAGGTTGTAATGGCGGTACAACTGTAACTAATAACTGATCAATAAT
     ───────────────────────────────CMV Pro─────────────────────────────────
     ─────────────────────────────hCMV Promoter───────────────────────────────

ATAGTAATCAATTACGGGGTCATTAGTTCATAGCCCATATATGGAGTTCCGCGTTACATAACTTACGGTAAATGGCCCGC
                                                                                      3040
     TATCATTAGTTAATGCCCCAGTAATCAAGTATCGGGTATATACCTCAAGGCGCAATGTATTGAATGCCATTTACCGGGCG
     ───────────────────────────────CMV Pro─────────────────────────────────
     ─────────────────────────────hCMV Promoter───────────────────────────────

CTGGCTGACCGCCCAACGACCCCCGCCCATTGACGTCAATAATGACGTATGTTCCCATAGTAACGCCAATAGGGACTTTC
                                                                                      3120
     GACCGACTGGCGGGTTGCTGGGGGCGGGTAACTGCAGTTATTACTGCATACAAGGGTATCATTGCGGTTATCCCTGAAAG
     ───────────────────────────────CMV Pro─────────────────────────────────
     ─────────────────────────────hCMV Promoter───────────────────────────────
```

Wednesday, January 23, 2002 4:07 PM
P-GD1915 pLNC-LCA Map.MPD (1 > 7490)  Site and Sequence FIG. 7 (part 6 of 12)

```
                                                              NdeI
CATTGACGTCAATGGGTGGAGTATTTACGGTAAACTGCCCACTTGGCAGTACATCAAGTGTATCATATGCCAAGTACGCC
                                                                                  3200
GTAACTGCAGTTACCCACCTCATAAATGCCATTTGACGGGTGAATCCGTCATGTAGTTCACATAGTATACGGTTCATGCGG
                               CMV Pro
                             hCMV Promoter CCCTATTGACGTCAATGACGGTAAATGGCCCGCCTGGCATTATGCCCACTACATGACCTTATGGGACTTTCCTACTTGGC
                                                                                  3280
GGGATAACTGCAGTTACTGCCATTTACCGGGCGGACCGTAATACGGGTGATGTACTGGAATACCCTGAAAGGATGAACCG
                               CMV Pro
                             hCMV Promoter NcoI
AGTACATCTACCTATTAGTCATCGCTATTACCATGGTCATGCCCTTTTCGCAGTACATCAATGGGCGTGGATAGCGGTTT
                                                                                  3360
TCATGTAGATGGATAATCAGTAGCGATAATGGTACCACTACGCCAAAACCGTCATGTAGTTACCCGCACCTATCGCCAAA
                               CMV Pro
                             hCMV Promoter GACTCACGGGGATTTCCAAGTCTCCACCCCATTGACGTCAATGGGAGTTTGTTTTGGCACCAAAATCAACGGGACTTTCC
                                                                                  3440
CTGAGTGCCCCTAAAGGTTCAGAGGTGGGGTAACTGCAGTTACCCTCAAACAAAACCGTGGTTTTAGTTGCCCTGAAAGG
                               CMV Pro
                             hCMV Promoter SacI
AAAATGTCGTAACAACTCCGCCCCATTGACGCAAATGGGCGGTAGGCATGTACGGTGGGAGGTCTATATAAGCAGAGCTC
                                                                                  3520
TTTTACAGCATTGTTGAGGCGGGGTAACTGCGTTTACCCGCCATCCGTACATGCCACCCTCCAGATATATTCGTCTCGAG
                               CMV Pro
                             hCMV Promoter GTTTAGTGAACCGTCAGATCGCCTGGAGACGCCATCCACGCTGTTTTGACCTCCATAGAAGACACCGGGACCGATCCAGC
                                                                                  3600
CAAATCACTTGGCAGTCTAGCGGACCTCTGCGGTAGGTGCGACAAAACTGGAGGTATCTTCTGTGGCCCTGGCTAGGTCG
                               CMV Pro
                             hCMV Promoter SacII    HindIII
CTCCGCGGCCCCAAGCTTGTTATCACAAGTTTGTACAAAAAAGCAGGCTTCGAAGGAGATAGAACCAATTCTCTAAGGAA
                                                                                  3680
GAGGCGCCGGGGTTCGAACAATAGTGTTCAAACATGTTTTTTCGTCCGAAGCTTCCTCTATCTTGGTTAAGAGATTCCTT
        CMV Pro                        att B1
      hCMV Promoter                    att B1
```

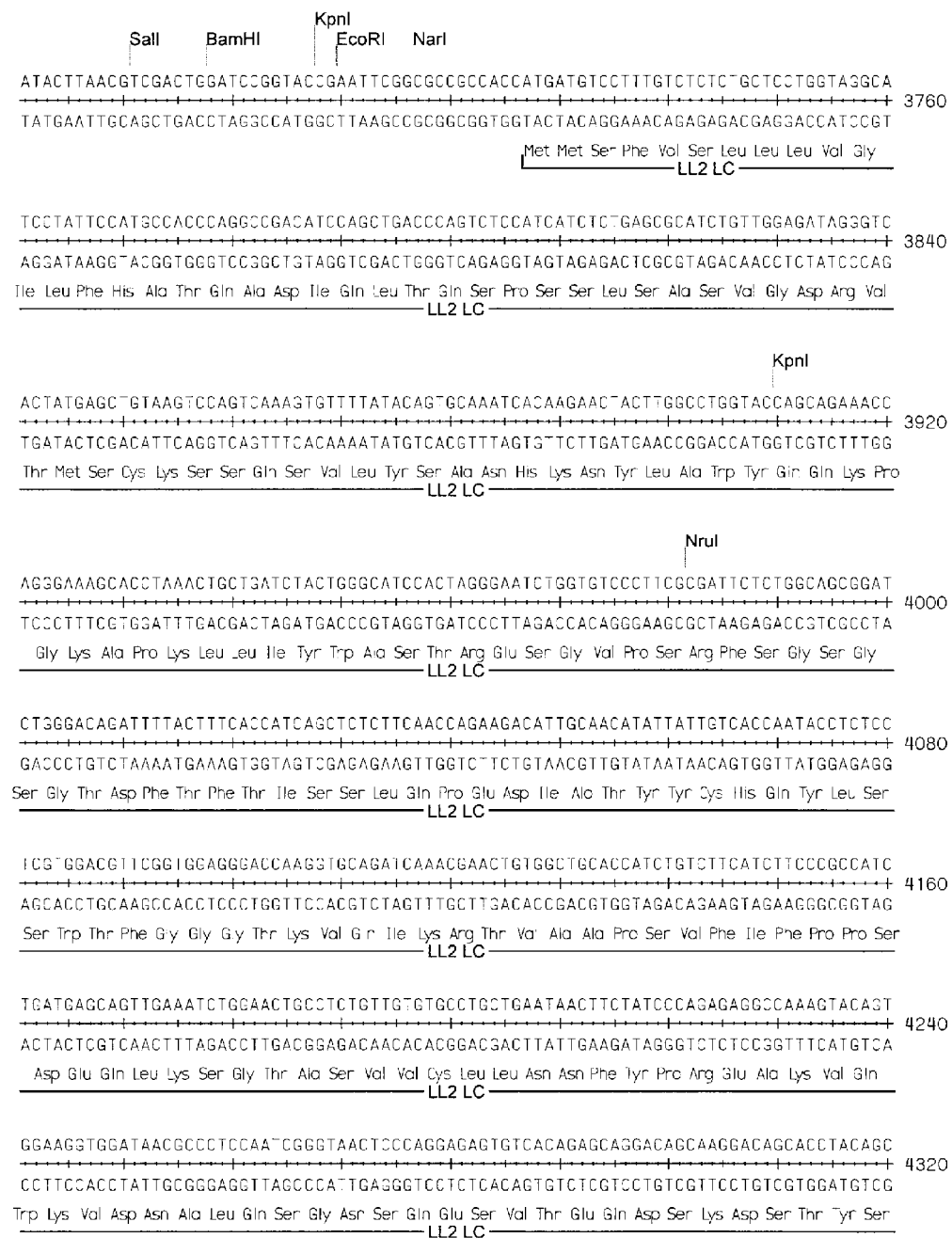
FIG. 7 (part 7 of 12)

Wednesday, January 23, 2002 4:07 PM
P-GD1915 pLNC-LCA Map.MPD (1 > 7490) Site and Sequence     FIG. 7 (part 8 of 12)

```
CTCAGCAGCACCCTGACGCTGAGCAAAGCAGACTACGAGAAACACAAAGTCTACGCCTGCGAAGTCACCCATCAGGGCCT
++++++++++++++++++++++++++++++++++++++++++++++++++++++++++++++++++++++++++++++++ 4400
GAGTCGTCGTGGGACTGCGACTCGTTTCGTCTGATGCTCTTTGTGTTTCAGATGCGGACGCTTCAGTGGGTAGTCCCGGA
 Leu Ser Ser Thr Leu Thr Leu Ser Lys Ala Asp Tyr Glu Lys His Lys Val Tyr Ala Cys Glu Val Thr His Gln Gly Leu
                                        LL2 LC
```

```
     Sacl                               BglII XhoI    EcoRV
                                              |      XbaI
GAGCTCGCCCGTCACAAAGAGCTTCAACAGGGGAGAGTGTTAGATCTCGAGATATCTAGACCCAGCTTTCTTGTACAAAG
++++++++++++++++++++++++++++++++++++++++++++++++++++++++++++++++++++++++++++++++ 4480
CTCGAGCGGGCAGTGTTTCTCGAAGTTGTCCCCTCTCACAATCTAGAGCTCTATAGATCTGGGTCGAAAGAACATGTTTC
 Ser Ser Pro Val Thr Lys Ser Phe Asn Arg Gly Glu Cys  *              att B2
                   LL2 LC                                            att B2
```

```
         ClaI
TGGTGATAACATCGATAAAATAAAAGATTTTATTTAGTCTCCAGAAAAAGGGGGGAATGAAAGACCCCACCTGTAGGTTT
++++++++++++++++++++++++++++++++++++++++++++++++++++++++++++++++++++++++++++++++ 4560
ACCACTATTGTAGCTATTTTATTTTCTAAAATAAATCAGAGGTCTTTTTCCCCCCTTACTTTCTGGGGTGGACATCCAAA
 att                                                    3' LTR
 att                                                    3' LTR MoMLV
```

```
    NheI
GGCAAGCTAGCTTAAGTAACGCCATTTTGCAAGGCATGGAAAAATACATAACTGAGAATAGAGAAGTTCAGATCAAGGTC
++++++++++++++++++++++++++++++++++++++++++++++++++++++++++++++++++++++++++++++++ 4640
CCGTTCGATCGAATTCATTGCGGTAAAACGTTCCGTACCTTTTTATGTATTGACTCTTATCTCTTCAAGTCTAGTTCCAG
                               3' LTR
                               3' LTR MoMLV
```

```
                    EcoRV
AGGAACAGATGGAACAGCTGAATATGGGCCAAACAGGATATCTGTGGTAAGCAGTTCCTGCCCCGGCTCAGGGCCAAGAA
++++++++++++++++++++++++++++++++++++++++++++++++++++++++++++++++++++++++++++++++ 4720
TCCTTGTCTACCTTGTCGACTTATACCCGGTTTGTCCTATAGACACCATTCGTCAAGGACGGGGCCGAGTCCCGGTTCTT
                               3' LTR
                               3' LTR MoMLV
```

```
              EcoRV
CAGATGGAACAGCTGAATATGGGCCAAACAGGATATCTGTGGTAAGCAGTTCCTGCCCCGGCTCAGGGCCAAGAACAGAT
++++++++++++++++++++++++++++++++++++++++++++++++++++++++++++++++++++++++++++++++ 4800
GTCTACCTTGTCGACTTATACCCGGTTTGTCCTATAGACACCATTCGTCAAGGACGGGGCCGAGTCCCGGTTCTTGTCTA
                               3' LTR
                               3' LTR MoMLV
```

```
                             XbaI
GGTCCCCAGATGCGGTCCAGCCCTCAGCAGTTTCTAGAGAACCATCAGATGTTTCCAGGGTGCCCCAAGGACCTGAAATG
++++++++++++++++++++++++++++++++++++++++++++++++++++++++++++++++++++++++++++++++ 4880
CCAGGGGTCTACGCCAGGTCGGGAGTCGTCAAAGATCTCTTGGTAGTCTACAAAGGTCCCACGGGGTTCCTGGACTTTAC
                               3' LTR
                               3' LTR MoMLV
```

Wednesday, January 23, 2002 4:07 PM  FIG. 7 (part 9 of 12)
P-GD1915 pLNC-LCA Map.MPD (1 > 7490)  Site and Sequence

```
                                                                    SacI
ACCCTGTGCCTTATTTGAACTAACCAATCAGTTCGCTTCTCGCTTCTGTTCGCGCGCTTCTGCTCCCCGAGCTCAATAAA
                                                                                    4960
TGGGACACGGAATAAACTTGATTGGTTAGTCAAGCGAAGAGCGAAGACAAGCGCGCGAAGACGAGGGGCTCGAGTTATTT
                                    3' LTR
                                 3' LTR MoMLV

NarI                              SmaI   KpnI
AGAGCCCACAACCCCTCACTCGGGGCGCCAGTCCTCCGATTGACTGAGTCGCCCGGGTACCCGTGTATCCAATAAACCCT
                                                                                    5040
TCTCGGGTGTTGGGGAGTGAGCCCCGCGGTCAGGAGGCTAACTGACTCAGCGGGCCCATGGGCACATAGGTTATTTGGGA
                                    3' LTR
                                 3' LTR MoMLV

CTTGCAGTTGCATCCGACTTGTGGTCTCGCTGTTCCTTGGAGGGTCTCCTCTGAGTGATTGACTACCCGTCAGCGGGGG
                                                                                    5120
GAACGTCAACGTAGGCTGAACACCAGAGCGACAAGGAACCCTCCCAGAGGAGACTCACTAACTGATGGGCAGTCGCCCCC
                                    3' LTR
                                 3' LTR MoMLV

TCTTTCATTTGGGGGCTCGTCCGGGATCGGGAGACCCCTGCCCAGGGACCACCGACCCACCACCGGGAGGTAAGCTGGCT
                                                                                    5200
AGAAAGTAAACCCCCGAGCAGGCCCTAGCCCTCTGGGGACGGGTCCCTGGTCGCTGCGTGGTGGCCCTCCATTCGACCGA
  3' LTR
 -3' LTR Mo

GCCTCGCGCGTTTCGGTGATGACGGTGAAAACCTCTGACACATGCAGCTCCCGGAGACGGTCACAGCTTGTCTGTAAGCG
                                                                                    5280
CGGAGCGCGCAAAGCCACTACTGCCACTTTTGGAGACTGTGTACGTCGAGGGCCTCTGCCAGTGTCGAACAGACATTCGC

GATGCCGGGAGCAGACAAGCCCGTCAGGGCGCGTCAGCGGGTGTTGGCGGGTGTCGGGGCGCAGCCATGACCCAGTCACG
                                                                                    5360
CTACGGCCCTCGTCTGTTCGGGCAGTCCCGCGCAGTCGCCCACAACCGCCCACAGCCCCGCGTCGGTACTGGGTCAGTGC

NdeI
TAGCGATAGCGGAGTGTATACTGGCTTAACTATGCGGCATCAGAGCAGATTGTACTGAGAGTGCACCATATGCGGTGTGA
                                                                                    5440
ATCGCTATCGCCTCACATATGACCGAATTGATACGCCGTAGTCTCGTCTAACATGACTCTCACGTGGTATACGCCACACT

AATACCGCACAGATGCGTAAGGAGAAAATACCGCATCAGGCGCTCTTCCGCTTCCTCGCTCACTGACTCGCTGCGCTCGG
                                                                                    5520
TTATGGCGTGTCTACGCATTCCTCTTTTATGGCGTAGTCCGCGAGAAGGCGAAGGAGCGAGTGACTGAGCGACGCGAGCC

TCGTTCGGCTGCGGCGAGCGGTATCAGCTCACTCAAAGGCGGTAATACGGTTATCCACAGAATCAGGGCATAACGCAGGA
                                                                                    5600
AGCAAGCCGACGCCGCTCGCCATAGTCGAGTGAGTTTCCGCCATTATGCCAATAGGTGTCTTAGTCCCCTATTGCGTCCT

AAGAACATGTGAGCAAAAGGCCAGCAAAAGGCCAGGAACCGTAAAAAGGCCGCGTTGCTGGCGTTTTTCCATAGGCTCCG
                                                                                    5680
TTCTTGTACACTCGTTTTCCGGTCGTTTTCCGGTCCTTGGCATTTTTCCGGCGCAACGACCGCAAAAAGGTATCCGAGGC
```

Wednesday, January 23, 2002 4:07 PM
P-GD1915 pLNC-LCA Map.MPD (1 > 7490)  Site and Sequence FIG. 7 (part 10 of 12)

```
CCCCCCTGACGAGCATCACAAAAATCGACGCTCAAGTCAGAGGTGGCGAAACCCGACAGGACTATAAAGATACCAGGCGT
+---+---+---+---+---+---+---+---+---+---+---+---+---+---+---+---+  5760
GGGGGGACTGCTCGTAGTGTTTTAGCTGCGAGTTCAGTCTCCACCGCTTTGGGCTGTCCTGATATTTCTATGGTCCGCA

TTCCCCCTGGAAGCTCCCTCGTGCGCTCTCCTGTTCCGACCCTGCCGCTTACCGGATACCTGTCCGCCTTTCTCCCTTCG
+---+---+---+---+---+---+---+---+---+---+---+---+---+---+---+---+  5840
AAGGGGGACCTTCGAGGGAGCACGCGAGAGGACAAGGCTGGGACGGCGAATGGCCTATGGACAGGCGGAAAGAGGGAAGC

GGAAGCGTGGCGCTTTCTCATAGCTCACGCTGTAGGTATCTCAGTTCGGTGTAGGTCGTTCGCTCCAAGCTGGGCTGTGT
+---+---+---+---+---+---+---+---+---+---+---+---+---+---+---+---+  5920
CCTTCGCACCGCGAAAGAGTATCGAGTGCGACATCCATAGAGTCAAGCCACATCCAGCAAGCGAGGTTCGACCCGACACA

GCACGAACCCCCCGTTCAGCCCGACCGCTGCGCCTTATCCGGTAACTATCGTCTTGAGTCCAACCCGGTAAGACACGACT
+---+---+---+---+---+---+---+---+---+---+---+---+---+---+---+---+  6000
CGTGCTTGGGGGGCAAGTCGGGCTGGCGACGCGGAATAGGCCATTGATAGCAGAACTCAGGTTGGGCCATTCTGTGCTGA

TATCGCCACTGGCAGCAGCCACTGGTAACAGGATTAGCAGAGCGAGGTATGTAGGCGGTGCTACAGAGTTCTTGAAGTGG
+---+---+---+---+---+---+---+---+---+---+---+---+---+---+---+---+  6080
ATAGCGGTGACCGTCGTCGGTGACCATTGTCCTAATCGTCTCGCTCCATACATCCGCCACGATGTCTCAAGAACTTCACC

TGGCCTAACTACGGCTACACTAGAAGGACAGTATTTGGTATCTGCGCTCTGCTGAAGCCAGTTACCTTCGGAAAAAGAGT
+---+---+---+---+---+---+---+---+---+---+---+---+---+---+---+---+  6160
ACCGGATTGATGCCGATGTGATCTTCCTGTCATAAACCATAGACGCGAGACGACTTCGGTCAATGGAAGCCTTTTTCTCA

TGGTAGCTCTTGATCCGGCAAACAAACCACCGCTGGTAGCGGTGGTTTTTTTGTTTGCAAGCAGCAGATTACGCGCAGAA
+---+---+---+---+---+---+---+---+---+---+---+---+---+---+---+---+  6240
ACCATCGAGAACTAGGCCGTTTGTTTGGTGGCGACCATCGCCACCAAAAAAACAAACGTTCGTCGTCTAATGCGCGTCTT

AAAAAGGATCTCAAGAAGATCCTTTGATCTTTTCTACGGGGTCTGACGCTCAGTGCAACGAAAACTCACGTTAAGGGATT
+---+---+---+---+---+---+---+---+---+---+---+---+---+---+---+---+  6320
TTTTTCCTAGAGTTCTTCTAGGAAACTAGAAAAGATGCCCCAGACTGCGAGTCACCTTGCTTTTGAGTGCAATTCCCTAA

BspHI                                  DraI            DraI
TTGGTCATGAGATTATCAAAAAGGATCTTCACCTAGATCCTTTTAAATTAAAAATGAAGTTTTAAATCAATCTAAAGTAT
+---+---+---+---+---+---+---+---+---+---+---+---+---+---+---+---+  6400
AACCAGTACTCTAATAGTTTTTCCTAGAAGTGGATCTAGGAAAATTTAATTTTTACTTCAAAATTTAGTTAGATTTCATA

ATATGAGTAAACTTGGTCTGACAGTTACCAATGCTTAATCAGTGAGGCACCTATCTCAGCGATCTGTCTATTTCGTTCAT
+---+---+---+---+---+---+---+---+---+---+---+---+---+---+---+---+  6480
TATACTCATTTGAACCAGACTGTCAATGGTTACGAATTAGTCACTCCGTGGATAGAGTCGCTAGACAGATAAAGCAAGTA
                                                      ◄━━━━━━━━ AMP ━━━━━
                                                      ━━━━━━━━ AMP ━━━━━━━

CCATAGTTGCCTGACTCCCCGTCGTGTAGATAACTACGATACGGGAGGGCTTACCATCTGGCCCCAGTGCTGCAATGATA
+---+---+---+---+---+---+---+---+---+---+---+---+---+---+---+---+  6560
GGTATCAACGGACTGAGGGGCAGCACATCTATTGATGCTATGCCCTCCCGAATGGTAGACCGGGGTCACGACGTTACTAT
━━━━━━━━━━━━━━━━━━━━━━━━━━━━━━━━━━━━━━━━━━━━━━━━━━ AMP ━━━━━━━━━━
━━━━━━━━━━━━━━━━━━━━━━━━━━━━━━━━━━━━━━━━━━━━━━━━━ AMP ━━━━━━━━━━━━━
```

FIG. 7 (part 11 of 12)

```
CCGCGAGACCCACGCTCACCGGCTCCAGATTTATCAGCAATAAACCAGCCAGCCGGAAGGGCCGAGCGCAGAAGTGGTCC
++++++++++++++++++++++++++++++++++++++++++++++++++++++++++++++++++++++++++++++++ 6640
GGCGCTCTGGGTGCGAGTGGCCGAGGTCTAAATAGTCGTTATTTGGTCGGTCGGCCTTCCCGGCTCGCGTCTTCACCAGG
                              AMP
                              AMP
                                                                            FspI
TGCAACTTTATCCGCCTCCATCCAGTCTATTAATTGTTGCCGGGAAGCTAGAGTAAGTAGTTCGCCAGTTAATAGTTTGC
++++++++++++++++++++++++++++++++++++++++++++++++++++++++++++++++++++++++++++++++ 6720
ACGTTGAAATAGGCGGAGGTAGGTCAGATAATTAACAACGGCCCTTCGATCTCATTCATCAAGCGGTCAATTATCAAACG
                              AMP
                              AMP

PstI
GCAACGTTGTTGCCATTGCTGCAGGCATCGTGGTGTCACGCTCGTCGTTGGTATGGCTTCATTCAGCTCCGGTTCCCAA
++++++++++++++++++++++++++++++++++++++++++++++++++++++++++++++++++++++++++++++++ 6800
CGTTGCAACAACGGTAACGACGTCCGTAGCACCACAGTGCGAGCAGCAAACCATACCGAAGTAAGTCGAGGCCAAGGGTT
                              AMP
                              AMP

PvuI
CGATCAAGGCGAGTTACATGATCCCCCATGTTGTGCAAAAAAGCGGTTAGCTCCTTCGGTCCTCCGATCGTTGTCAGAAG
++++++++++++++++++++++++++++++++++++++++++++++++++++++++++++++++++++++++++++++++ 6880
GCTAGTTCCGCTCAATGTACTAGGGGGTACAACACGTTTTTTCGCCAATCGAGGAAGCCAGGAGGCTAGCAACAGTCTTC
                              AMP
                              AMP

TAAGTTGGCCGCAGTGTTATCACTCATGGTTATGGCAGCACTGCATAATTCTCTTACTGTCATGCCATCCGTAAGATGCT
++++++++++++++++++++++++++++++++++++++++++++++++++++++++++++++++++++++++++++++++ 6960
ATTCAACCGGCGTCACAATAGTGAGTACCAATACCGTCGTGACGTATTAAGAGAATGACAGTACGGTAGGCATTCTACGA
                              AMP
                              AMP

TTTCTGTGACTGGTGAGTACTCAACCAAGTCATTCTGAGAATAGTGTATGCGGCGACCGAGTTGCTCTTGCCCGGCGTCA
++++++++++++++++++++++++++++++++++++++++++++++++++++++++++++++++++++++++++++++++ 7040
AAAGACACTGACCACTCATGAGTTGGTTCAGTAAGACTCTTATCACATACGCCGCTGGCTCAACGAGAACGGGCCGCAGT
                              AMP
                              AMP

DraI
ACACGGGATAATACCGCGCCACATAGCAGAACTTTAAAAGTGCTCATCATTGGAAAACGTTCTTCGGGGCGAAAACTCTC
++++++++++++++++++++++++++++++++++++++++++++++++++++++++++++++++++++++++++++++++ 7120
TGTGCCCTATTATGGCGCGGTGTATCGTCTTGAAATTTTCACGAGTAGTAACCTTTTGCAAGAAGCCCCGCTTTTGAGAG
                              AMP
                              AMP
```

Wednesday, January 23, 2002 4:07 PM
P-GD1915 pLNC-LCA Map.MPD (1 > 7490)  Site and Sequence FIG. 7 (part 12 of 12)

```
AAGGATCTTACCGCTGTTGAGATCCAGTTCGATGTAACCCACTCGTGCACCCAACTGATCTTCAGCATCTTTTACTTTCA
++++++++|++++++++|++++++++|++++++++|++++++++|++++++++|++++++++|++++++++|++++++++|++++  7200
TTCCTAGAATGGCGACAACTCTAGGTCAAGCTACATTGGGTGAGCACGTGGGTTGACTAGAAGTCGTAGAAAATGAAAGT
                                        ━━━━━ AMP ━━━━━━━━━━━━━━━━━━━━━━━━━━━━━━━━━
                                        ━━━━━ AMP ━━━━━━━━━━━━━━━━━━━━━━━━━━━━━━━━━━

CCAGCGTTTCTGGGTGAGCAAAAACAGGAAGGCAAAATGCCGCAAAAAAGGGAATAAGGGCGACACGGAAATGTTGAATA
++++++++|++++++++|++++++++|++++++++|++++++++|++++++++|++++++++|++++++++|++++++++|++++  7280
GGTCGCAAAGACCCACTCGTTTTTGTCCTTCCGTTTTACGGCGTTTTTTCCCTTATTCCCGCTGTGCCTTTACAACTTAT
━━━━━━━━━━━━━━━━━━━━━━━━━━━━━━━━━━━━━━━━ AMP ━━━━━━━━━━━━━━━━━━━━━━━━━━━━━━━━━━━━━
━━━━━━━━━━━━━━━━━━━━━━━━━━━━━━━━━━━━━━━━ AMP ━━━━━━━━━━━━━━━━━━━━━━━━━━━━━━━━━━━━━━

BspHI
CTCATACTCTTCCTTTTTCAATATTATTGAAGCATTTATCAGGGTTATTGTCTCATGAGCGGATACATATTTGAATGTAT
++++++++|++++++++|++++++++|++++++++|++++++++|++++++++|++++++++|++++++++|++++++++|++++  7360
GAGTATGAGAAGGAAAAAGTTATAATAACTTCGTAAATAGTCCCAATAACAGAGTACTCGCCTATGTATAAACTTACATA
'AMP'
-AMP⌐

BspHI
TTAGAAAAATAAACAAATAGGGGTTCCGCGCACATTTCCCCGAAAAGTGCCACCTGACGTCTAAGAAACCATTATTATCA
++++++++|++++++++|++++++++|++++++++|++++++++|++++++++|++++++++|++++++++|++++++++|++++  7440
AATCTTTTATTTGTTTATCCCCAAGGCGCGTGTAAAGGGGCTTTTCACGGTGGACTGCAGATTCTTTGGTAATAATAGT

TGACATTAACCTATAAAAATAGGCGTATCACGAGGCCCTTTCGTCTTCAA
++++++++|++++++++|++++++++|++++++++|+++++++⇒   7490
ACTGTAATTGGATATTTTTATCCGCATAGTGCTCCGGGAAAGCAGAAGTT
```

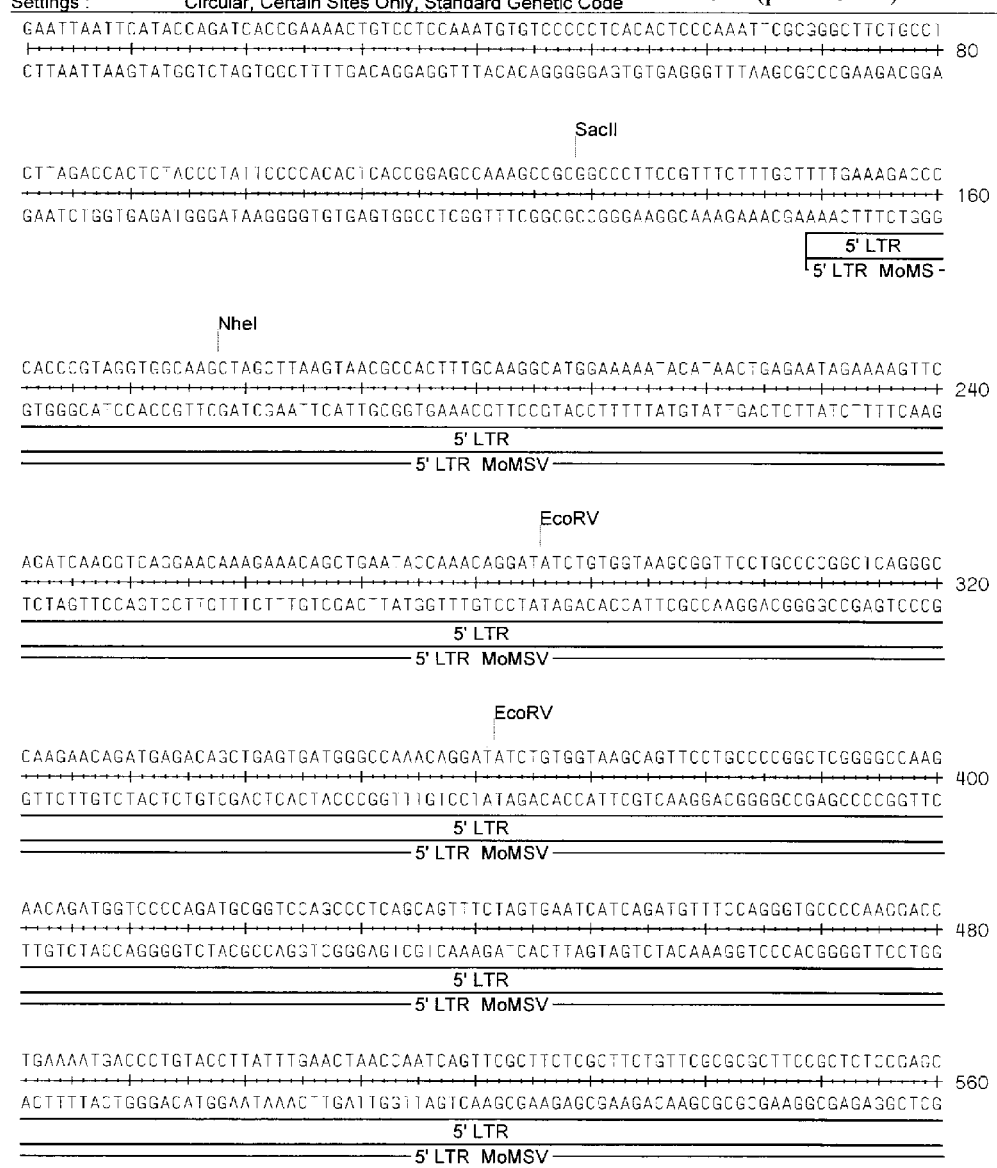

Wednesday, January 23, 2002 4:08 PM
P-GD1721 pLNC-LCB.MPD (1 > 7472) Site and Sequence FIG. 8 (part 2 of 12)

```
         SacI                         AscI                              SmaI  KpnI
TCAATAAAAGAGCCCACAACCCCTCACTCGCCGCGCCAGTCTTCCGATAGACTGCGTCGCCCGGGTACCCGTATTCCCAA
                                                                                 640
AGTTATTTTCTCGGGTGTTGGGGAGTGAGCCGCGCGGTCAGAAGGCTATCTGACGCAGCGGGCCCATGGGCATAAGGGTT
                              5' LTR
                              5' LTR  MoMSV

TAAAGCCTCTTGCTGTTTGCATCCGAATCGTGGTCTCGCTGTTCCTTGGGAGGGTCTCCTCTGAGTGATTGACTACCCAC
                                                                                 720
ATTTCGGAGAACGACAAACGTAGGCTTAGCACCAGAGCGACAAGGAACCCTCCCAGAGGAGACTCACTAACTGATGGGTG
                              5' LTR
                              5' LTR  MoMSV

GACGGGGGTCTTTCATTTGGGGGCTCGTCCGGGATTTGGAGACCCCTGCCCAGGCACCACCGACCCACCACCGGGAGGTA
                                                                                 800
CTGCCCCCAGAAAGTAAACCCCGAGCAGGCCCTAAACCTCTGGGGACGGGTCCCTGGTGGCTGGGTGGTGGCCCTCCAT
    5' LTR           >
   5' LTR MoMSV

SpeI
AGCTGGCCAGCAACTTATCTGTGTCTGTCCGATTGTCTAGTGTCTATGTTTGATGTTATGCGCCTGCGTCTGTACTAGTT
                                                                                 880
TCGACCGGTCGTTGAATAGACACAGACAGGCTAACAGATCACAGATACAAACTACAATACGCGGACGCAGACATGATCAA
                                        Pkg Rgn
                                  Extended Packaging Region AGCTAACTAGCTCTGTATCTGGCGGACCCGTGGTGGAACTGACGAGTTCTGAACACCCGGCCGCAACCCTGGGAGACGTC
                                                                                 960
TCGATTGATCGAGACATAGACCGCCTGGGCACCACCTTGACTGCTCAAGACTTGTGGGCCGGCGTTGGGACCCTCTGCAG
                                        Pkg Rgn
                                  Extended Packaging Region CCAGGGACTTTGGGGGCCGTTTTTGTGGCCCGACCTGAGGAAGGGAGTCGATGTGGAATCCGACCCCGTCAGGATATGTG
                                                                                 1040
GGTCCCTGAAACCCCCGGCAAAAACACCGGGCTGGACTCCTTCCCTCAGCTACACCTTAGGCTGGGGCAGTCCTATACAC
                                        Pkg Rgn
                                  Extended Packaging Region GTTCTGGTAGGAGACGAGAACCTAAAACAGTTCCCGCCTCCGTCTGAATTTTTGCTTTCGGTTTGGAACCGAAGCCGCGC
                                                                                 1120
CAAGACCATCCTCTGCTCTTGGATTTTGTCAAGGGCGGAGGCAGACTTAAAAACGAAAGCCAAACCTTGGCTTCGGCGCG
                                        Pkg Rgn
                                  Extended Packaging Region PstI      PstI
GTCTTGTCTGCTGCAGCGCTGCAGCATCGTTCTGTGTTGTCTCTGTCTGACTGTGTTTCTGTATTTGTCTGAAAATTAGG
                                                                                 1200
CAGAACAGACGACGTCGCGACGTCGTAGCAAGACACAACAGAGACAGACTGACACAAAGACATAAACAGACTTTTAATCC
                                        Pkg Rgn
                                  Extended Packaging Region
```

Wednesday, January 23, 2002 4:08 PM
P-GD1721 pLNC-LCB.MPD (1 > 7472) Site and Sequence  FIG. 8 (part 3 of 12)

```
GCCAGACTGTTACCACTCCCTTAAGTTTGACCTTAGGTCACTGGAAAGATGTCGAGCGGATCGCTCACAACCAGTCGGTA
                                                                                 1280
CGGTCTGACAATGGTGAGGGAATTCAAACTGGAATCCAGTGACCTTTCTACAGCTCGCCTAGCGAGTGTTGGTCAGCCAT
                            ━━━━━━━━━━━━━━ Pkg Rgn ━━━━━━━━━━━━━━
                   ━━━━━━━━━━━━━━━━━━━━━━━━ Extended Packaging Region ━━━━━━━━━━━━━━━━━━━━━━━━

PstI
GATGTCAAGAAGAGACGTTGGGTTACCTTCTGCTCTGCAGAATGGCCAACCTTTAACGTCGGATGGCCGCGAGACGGCAC
                                                                                 1360
CTACAGTTCTTCTCTGCAACCCAATGGAAGACGAGACGTCTTACCGGTTGGAAATTGCAGCCTACCGGCGCTCTGCCGTG
                            ━━━━━━━━━━━━━━ Pkg Rgn ━━━━━━━━━━━━━━
                   ━━━━━━━━━━━━━━━━━━━━━━━━ Extended Packaging Region ━━━━━━━━━━━━━━━━━━━━━━━━

CTTTAACCGAGACCTCATCACCCAGGTTAAGATCAAGGTCTTTTCACCTGGCCCGCATGGACACCCAGACCAGGTCCCCT
                                                                                 1440
GAAATTGGCTCTGGAGTAGTGGGTCCAATTCTAGTTCCAGAAAAGTGGACCGGGCGTACCTGTGGGTCTGGTCCAGGGGA
                            ━━━━━━━━━━━━━━ Pkg Rgn ━━━━━━━━━━━━━━
                   ━━━━━━━━━━━━━━━━━━━━━━━━ Extended Packaging Region ━━━━━━━━━━━━━━━━━━━━━━━━

ACATCGTGACCTGGGAAGCCTTGGCTTTTGACCCCCTCCCTGGGTCAAGCCCTTTGTACACCCTAAGCCTCCGCCTCCT
                                                                                 1520
TGTAGCACTGGACCCTTCGGAACCGAAAACTGGGGGGAGGGACCCAGTTCGGGAAACATGTGGGATTCGGAGGCGGAGGA
                            ━━━━━━━━━━━━━━ Pkg Rgn ━━━━━━━━━━━━━━
                   ━━━━━━━━━━━━━━━━━━━━━━━━ Extended Packaging Region ━━━━━━━━━━━━━━━━━━━━━━━━

CTTCCTCCATCCGCCCCGTCTCTCCCCCTTGAACCTCCTCGTTCGACCCCGCCTCGATCCTCCCTTTATCCAGCCCTCAC
                                                                                 1600
GAAGGAGGTAGGCGGGGCAGAGAGGGGGAACTTGGAGGAGCAAGCTGGGGCGGAGCTAGGAGGGAAATAGGTCGCGAGTG
                            ━━━━━━━━━━━━━━ Pkg Rgn ━━━━━━━━━━━━━━
                   ━━━━━━━━━━━━━━━━━━━━━━━━ Extended Packaging Region ━━━━━━━━━━━━━━━━━━━━━━━━

NarI    EcoRI      BclI
TCCTTCTCTAGGCGCCGGAATTCCGATCTGATCAAGAGACAGGATGAGCATCCTTTCGCATGATTGAACAAGATGGATTG
                                                                                 1680
AGGAAGAGATCCGCGGCCTTAAGGCTAGACTAGTTCTCTGTCCTACTCGTAGCAAAGCGTACTAACTTGTTCTACCTAAC
━━━ Pkg Rgn ━━━                                        Met Ile Glu Gln Asp Gly Leu
- Extended Packaging━┛                                  ┗Neomycin phosphotransfer- CACCCAGCTTCTCCGCCCCCTTGCGTGCACACGGCTATTCGGCTATGACTGGGCACAACAGACAATCGGCTGCTCTGATGC
                                                                                  1760
GTGCGTCCAAGAGGCCGGCGAACCCACCTCTCCGATAAGCCGATACTGACCCGTGTTGTCTGTTAGCCGACGAGACTACG
 His Ala Gly Ser Pro Ala Ala Trp Val Glu Arg Leu Phe Gly Tyr Asp Trp Ala Gln Gln Thr Ile Gly Cys Ser Asp Ala
                        ━━━━━━━━━━━━━━━━ Neomycin phosphotransferase ━━━━━━━━━━━━━━━━

NarI
CGCCGTGTTCCGGCTGTCAGCGCAGGGGCGCCCGGTTCTTTTTGTCAAGACCGACCTGTCCGGTGCCCTGAATGAACTGC
                                                                                 1840
GCGGCACAAGGCCGACAGTCGCGTCCCCGCGGGCCAAGAAAAACAGTTCTGGCTGGACAGGCCACGGGACTTACTTGACG
 Ala Val Phe Arg Leu Ser Ala Gln Gly Arg Pro Val Leu Phe Val Lys Thr Asp Leu Ser Gly Ala Leu Asn Glu Leu
                        ━━━━━━━━━━━━━━━━ Neomycin phosphotransferase ━━━━━━━━━━━━━━━━
```

Wednesday, January 23, 2002 4:08 PM  FIG. 8 (part 4 of 12)
P-GD1721 pLNC-LCB.MPD (1 > 7472)  Site and Sequence

```
                  PstI                                              FspI
                  |                                                 |
     AGGACGAGGCAGCGCGGCTATCGTGGCTGGCCACGACGGGCGTTCCTTGCGCAGCTGTGCTCGACGTTGTCACTGAAGCG
     --------+---------+---------+---------+---------+---------+---------+---------+ 1920
     TCCTGCTCCGTCGCGCCGATAGCACCGACCGGTGCTGCCCGCAAGGAACGCGTCGACACGAGCTGCAACAGTGACTTCGC
     Gln Asp Glu Ala Ala Arg Leu Ser Trp Leu Ala Thr Thr Gly Val Pro Cys Ala Ala Val Leu Asp Val Val Thr Glu Ala
     ─────────────────────────────────── Neomycin phosphotransferase ───────────────────────

GGAAGGGACTGGCTGCTATTGGGCGAAGTGCCGGGGCAGGATCTCCTGTCATCTCACCTTGCTCCTGCCGAGAAAGTATC
     --------+---------+---------+---------+---------+---------+---------+---------+ 2000
     CCTTCCCTGACCGACGATAACCCGCTTCACGGCCCCGTCCTAGAGGACAGTAGAGTGGAACGAGGACGGCTCTTTCATAG
     Gly Arg Asp Trp Leu Leu Leu Gly Glu Val Pro Gly Gln Asp Leu Leu Ser Ser His Leu Ala Pro Ala Glu Lys Val Ser
     ─────────────────────────────────── Neomycin phosphotransferase ───────────────────────

CATCATCGCTGATGCAATGCGGCGGCTCCATACGCTTGATCCGGCTACCTGCCCATTCGACCACCAAGCGAAACATCGCA
     --------+---------+---------+---------+---------+---------+---------+---------+ 2080
     GTAGTAGCGACTACGTTACGCCGCCGACGTATGCGAACTAGGCCGATGGACGGGTAAGCTGGTGGTTCGCTTTGTAGCGT
     Ile Met Ala Asp Ala Met Arg Arg Leu His Thr Leu Asp Pro Ala Thr Cys Pro Phe Asp His Gln Ala Lys His Arg
     ─────────────────────────────────── Neomycin phosphotransferase ───────────────────────

TCGAGCGAGCACGTACTCGGATGGAAGCCGGTCTTGTCGATCAGGATGATCTGGACGAAGAGCATCAGGGGCTCGCGCCA
     --------+---------+---------+---------+---------+---------+---------+---------+ 2160
     AGCTCGCTCGTGCATGAGCCTACCTTCGGCCAGAACAGCTAGTCCTACTAGACCTGCTTCTCGTAGTCCCCGAGCGCGGT
     Ile Glu Arg Ala Arg Thr Arg Met Glu Ala Gly Leu Val Asp Gln Asp Asp Leu Asp Glu Glu His Gln Gly Leu Ala Pro
     ─────────────────────────────────── Neomycin phosphotransferase ───────────────────────

SphI                                NcoI
                           |                                   |
     GCCGAACTGTTCGCCAGGCTCAAGGCGCGCATGCCCGACGGCGAGGATCTCGTCGTGACCCATGGCGATGCCTGCTTGCC
     --------+---------+---------+---------+---------+---------+---------+---------+ 2240
     CGGCTTGACAAGCGGTCCGAGTTCCGCGCGTACGGGCTGCCGCTCCTAGAGCAGCACTGGGTACCGCTACGGACGAACGG
     Ala Glu Leu Phe Ala Arg Leu Lys Ala Arg Met Pro Asp Gly Glu Asp Leu Val Val Thr His Gly Asp Ala Cys Leu Pro
     ─────────────────────────────────── Neomycin phosphotransferase ───────────────────────

NaeI
                                          |
     GAATATCATGGTGGAAAATGGCCGCTTTTCTGGATTCATCGACTGTGGCCGGCTGGGTGTGGCGGACCGCTATCAGGACA
     --------+---------+---------+---------+---------+---------+---------+---------+ 2320
     CTTATAGTACCACCTTTTACCGGCGAAAAGACCTAAGTAGCTGACACCGGCCGACCCACACCGCCTGGCGATAGTCCTGT
     Asn Ile Met Val Glu Asn Gly Arg Phe Ser Gly Phe Ile Asp Cys Gly Arg Leu Gly Val Ala Asp Arg Tyr Gln Asp
     ─────────────────────────────────── Neomycin phosphotransferase ───────────────────────

TAGCGTTGGCTACCCGTGATATTGCTGAAGAGCTTGGCGGCGAATGGGCTGACCGCTTCCTCGTGCTTTACGGTATCGCC
     --------+---------+---------+---------+---------+---------+---------+---------+ 2400
     ATCGCAACCGATGGGCACTATAACGACTTCTCGAACCGCCGCTTACCCGACTGGCGAAGGAGCACGAAATGCCATAGCGG
     Ile Ala Leu Ala Thr Arg Asp Ile Ala Glu Glu Leu Gly Gly Glu Trp Ala Asp Arg Phe Leu Val Leu Tyr Gly Ile Ala
     ─────────────────────────────────── Neomycin phosphotransferase ───────────────────────

GCTCCCGATTCGCAGCGCATCGCCTTCTATCGCCTTCTTGACGAGTTCTTCTGAGCGGGACTCTGGGGTTCGAAATGACC
     --------+---------+---------+---------+---------+---------+---------+---------+ 2480
     CGAGGGCTAAGCGTCGCGTAGCGGAAGATAGCGGAAGAACTGCTCAAGAAGACTCGCCCTGAGACCCCAAGCTTTACTGG
     Ala Pro Asp Ser Gln Arg Ile Ala Phe Tyr Arg Leu Leu Asp Glu Phe Phe  *
     ─────────────── Neomycin phosphotransferase ────────────────┘
```

Wednesday, January 23, 2002 4:08 PM
P-GD1721 pLNC-LCB.MPD (1 > 7472)  Site and Sequence FIG. 8 (part 5 of 12)

```
     GACCAAGCGACGCCCAACCTGCCATCACGAGATTTCGATTCCACCGCCGCCTTCTATGAAAGGTTGGGCTTCGGAATCGT
     ++++++++++++++++++++++++++++++++++++++++++++++++++++++++++++++++++++++++++++++++ 2560
     CTGGTTCGCTGCGGGTTGGACGGTAGTGCTCTAAAGCTAAGGTGGCGGCGGAAGATACTTTCCAACCCGAAGCCTTAGCA

Nael                                                    Smal
              |                                                       |
     TTTCCGGGACGCCGCCTGCATGATCCTCCAGCCCGGGGATCTCATGCTGCAGTTCTTCGCCCACCCCGGGCTCGATCCCC
     ++++++++++++++++++++++++++++++++++++++++++++++++++++++++++++++++++++++++++++++++ 2640
     AAAGGCCCTGCGGCCGACCTACTAGGAGGTCGCGCCCCTAGAGTACGACCTCAAGAAGCGGGTGGGGCCCGAGCTAGGGG Nrul
         |
     TCGCGAGTTGGTTCAGCTGCTGCCTGAGGCTGGACGACCTCGCGGAGTTCTACCGGCAGTGCAAATCCGTCGGCATCCAG
     ++++++++++++++++++++++++++++++++++++++++++++++++++++++++++++++++++++++++++++++++ 2720
     AGCGCTCAACCAAGTCGACGACGGACTCCGACCTGCTGGAGCGCCTCAAGATGGCCGTCACGTTTAGGCAGCCGTAGGTC Pstl
                                              |
     GAAACCAGCAGCGGCTATCCGCGCATCCATGCCCCCGAACTGCAGGAGTGGCGAGGCACCATGGCCGCTTTGGTCGAGGC
     ++++++++++++++++++++++++++++++++++++++++++++++++++++++++++++++++++++++++++++++++ 2800
     CTTTGGTCGTCGCCGATAGGCGCGTAGGTACGGGGGCTTGACGTCCTCACCCCTCCGTGCTACCGGCGAAACCAGCTCCG BamHI
     |
     GGATCCGGCCATTAGCCATATTATTCATTGGTTATATAGCATAAATCAATATTGGCTATTGGCCATTGCATACGTTGTAT
     ++++++++++++++++++++++++++++++++++++++++++++++++++++++++++++++++++++++++++++++++ 2880
     CCTAGGCCGGTAATCGGTATAATAAGTAACCAATATATCGTATTTAGTTATAACCGATAACCGGTAACGTATGCAACATA
     ═══════════════════════════════════════════════════════════════════════════════════
                                              CMV
     ═══════════════════════════════════════════════════════════════════════════════════
                                         hCMV Promoter Spel
                                                                           |
     CCATATCATAATATGTACATTTATATTGGCTCATGTCCAACATTACCGCCATGTTGACATTGATTATTGACTAGTTATTA
     ++++++++++++++++++++++++++++++++++++++++++++++++++++++++++++++++++++++++++++++++ 2960
     GGTATAGTATTATACATGTAAATATAACCGAGTACAGGTTGTAATGGCGGTACAACTGTAACTAATAACTGATCAATAAT
     ═══════════════════════════════════════════════════════════════════════════════════
                                              CMV
     ═══════════════════════════════════════════════════════════════════════════════════
                                         hCMV Promoter ATAGTAATCAATTACGGGGTCATTAGTTCATAGCCCATATATGGAGTTCCGCGTTACATAACTTACGGTAAATGGCCCGC
     ++++++++++++++++++++++++++++++++++++++++++++++++++++++++++++++++++++++++++++++++ 3040
     TATCATTAGTTAATGCCCCAGTAATCAAGTATCGGGTATATACCTCAAGGCGCAATGTATTGAATGCCATTTACCGGGCG
     ═══════════════════════════════════════════════════════════════════════════════════
                                              CMV
     ═══════════════════════════════════════════════════════════════════════════════════
                                         hCMV Promoter CTGGCTGACCGCCCAACGACCCCCGCCCATTGACGTCAATAATGACGTATGTTCCCATAGTAACGCCAATAGGGACTTTC
     ++++++++++++++++++++++++++++++++++++++++++++++++++++++++++++++++++++++++++++++++ 3120
     GACCGACTGGCGGGTTGCTGGGGGCGGGTAACTGCAGTTATTACTGCATACAAGGGTATCATTGCGGTTATCCCTGAAAG
     ═══════════════════════════════════════════════════════════════════════════════════
                                              CMV
     ═══════════════════════════════════════════════════════════════════════════════════
                                         hCMV Promoter
```

FIG. 8 (part 6 of 12)

Wednesday, January 23, 2002 4:08 PM  
P-GD1721 pLNC-LCB.MPD (1 > 7472) Site and Sequence FIG. 8 (part 7 of 12)

```
       Sall    BamHI      KpnI
                          | EcoRI   NarI
                          |  |       |
ATACTTAACGTCGACTGGATCCGGTACCGAATTCGGCGCCGCCACCATGATGTCCTTTGTCTCTCTGCTCCTGGTAGGCA
++++++++++|++++++++++|++++++++++|++++++++++|++++++++++|++++++++++|++++++++++|++  3760
TATGAATTGCAGCTGACCTAGGCCATGGCTTAAGCCGCGGCGGTGGTACTACAGGAAACAGAGAGACGAGGACCATCCGT
                                          Met Met Ser Phe Val Ser Leu Leu Val Gly
                                          |————————— MN14 LC —————————
```

```
TCCTATTCCATGCCACCCAGGCCGACATCCAGCTGACCCAGAGCCCAAGCAGCCTGAGCGCCAGCGTCGGTGACAGAGTG
++++++++++|++++++++++|++++++++++|++++++++++|++++++++++|++++++++++|++++++++++|++  3840
AGGATAAGGTACGGTGGGTCCGGCTGTAGGTCGACTGGGTCTCGGGTTCGTCGGACTCGCGGTCGCACCCACTGTCTCAC
Ile Leu Phe His Ala Thr Gln Ala Asp Ile Gln Leu Thr Gln Ser Pro Ser Ser Leu Ser Ala Ser Val Gly Asp Arg Val
————————————————————————— MN14 LC —————————————————————————
```

```
                                       KpnI
                                       |
ACCATCACCTGTAAGGCCAGTCAGGATGTGGGTACTTCTGTAGCCTGGTACCAGCAGAAGCCAGGTAAGGCTCCAAAGCT
++++++++++|++++++++++|++++++++++|++++++++++|++++++++++|++++++++++|++++++++++|++  3920
TGGTAGTGGACATTCCGGTCAGTCCTACACCCATGAAGACATCGGACCATGGTCGTCTTCGGTCCATTCCGAGGTTTCGA
Thr Ile Thr Cys Lys Ala Ser Gln Asp Val Gly Thr Ser Val Ala Trp Tyr Gln Gln Lys Pro Gly Lys Ala Pro Lys Leu
————————————————————————— MN14 LC —————————————————————————
```

```
                                                    KpnI
                                                    |
GCTGATCTACTGGACATCCACCCGGCACACTGGTGTGCCAAGCAGATTCAGCGGTAGCGGTAGCGGTACCGACTTCACCT
++++++++++|++++++++++|++++++++++|++++++++++|++++++++++|++++++++++|++++++++++|++  4000
CGACTAGATGACCTGTAGGTGGGCCGTGTGACCACACGGTTCGTCTAAGTCGCCATCGCCATCGCCATGGCTGAAGTGGA
Leu Ile Tyr Trp Thr Ser Thr Arg His Thr Gly Val Pro Ser Arg Phe Ser Gly Ser Gly Ser Gly Thr Asp Phe Thr
————————————————————————— MN14 LC —————————————————————————
```

```
TCACCATCAGCAGCCTCCAGCCAGAGGACATCGCCACCTACTACTGCCAGCAATATAGCCTCTATCGGTCGTTCGGCCAA
++++++++++|++++++++++|++++++++++|++++++++++|++++++++++|++++++++++|++++++++++|++  4080
AGTGGTAGTCGTCGGAGGTCGGTCTCCTGTAGCGGTGGATGATGACGGTCGTTATATCGGAGATAGCCAGCAAGCCGGTT
Phe Thr Ile Ser Ser Leu Gln Pro Glu Asp Ile Ala Thr Tyr Tyr Cys Gln Gln Tyr Ser Leu Tyr Arg Ser Phe Gly Gln
————————————————————————— MN14 LC —————————————————————————
```

```
GGGACCAAGGTGGAAATCAAACGAACTGTGGCTGCACCATCTGTCTTCATCTTCCCGCCATCTGATGAGCAGTTGAAATC
++++++++++|++++++++++|++++++++++|++++++++++|++++++++++|++++++++++|++++++++++|++  4160
CCCTGGTTCCACCTTTAGTTTGCTTGACACCGACGTGGTAGACAGAAGTAGAAGGGCGGTAGACTACTCGTCAACTTTAG
Gly Thr Lys Val Glu Ile Lys Arg Thr Val Ala Ala Pro Ser Val Phe Ile Phe Pro Pro Ser Asp Glu Gln Leu Lys Ser
————————————————————————— MN14 LC —————————————————————————
```

```
TGGAACTGCCTCTGTTGTGTGCCTGCTGAATAACTTCTATCCCAGAGAGGCCAAAGTACAGTGGAAGGTGGATAACGCCC
++++++++++|++++++++++|++++++++++|++++++++++|++++++++++|++++++++++|++++++++++|++  4240
ACCTTGACGGAGACAACACACGGACGACTTATTGAAGATAGGGTCTCTCCGGTTTCATGTCACCTTCCACCTATTGCGGG
Gly Thr Ala Ser Val Val Cys Leu Leu Asn Asn Phe Tyr Pro Arg Glu Ala Lys Val Gln Trp Lys Val Asp Asn Ala
————————————————————————— MN14 LC —————————————————————————
```

```
TCCAATCGGGTAACTCCCAGGAGAGTGTCACAGAGCAGGACAGCAAGGACAGCACCTACAGCCTCAGCAGCACCCTGACG
++++++++++|++++++++++|++++++++++|++++++++++|++++++++++|++++++++++|++++++++++|++  4320
AGGTTAGCCCATTGAGGGTCCTCTCACAGTGTCTCGTCCTGTCGTTCCTGTCGTGGATGTCGGAGTCGTCGTGGGACTGC
Leu Gln Ser Gly Asn Ser Gln Glu Ser Val Thr Glu Gln Asp Ser Lys Asp Ser Thr Tyr Ser Leu Ser Ser Thr Leu Thr
————————————————————————— MN14 LC —————————————————————————
```

FIG. 8 (part 8 of 12)
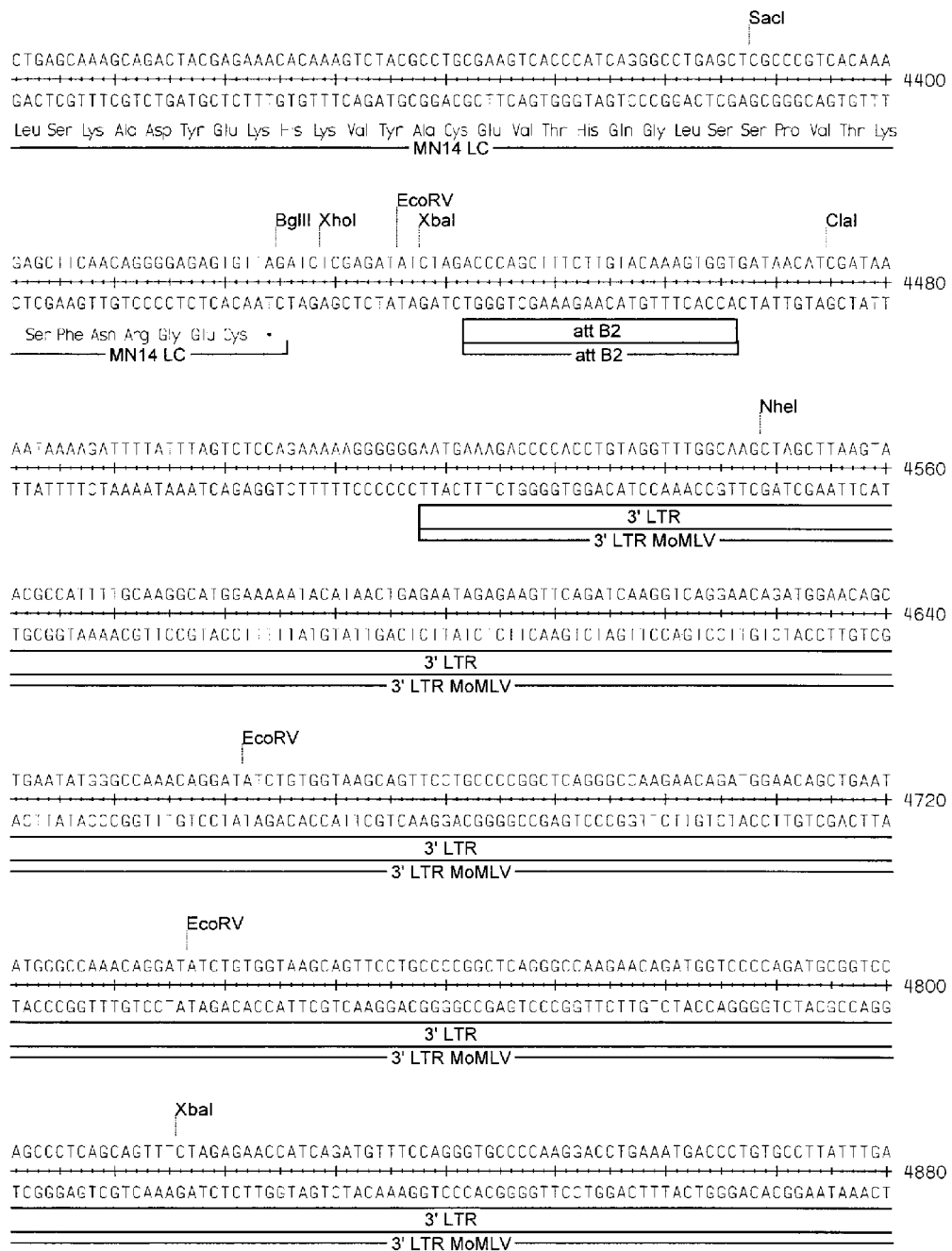

FIG. 8 (part 9 of 12)

```
                                                        SacI
ACTAACCAATCAGTTCGCTTCTCGCTTCTGTTCGCGCGCTTCTGCTCCCCGAGCTCAATAAAAGAGCCCACAACCCCTCA
++++++++++|++++++++++|++++++++++|++++++++++|++++++++++|++++++++++|++++++++++|++++ 4960
TGATTGGTTAGTCAAGCGAAGAGCGAAGACAAGCGCGCGAAGACCAGGGGCTCGAGTTATTTTCTCGGGTGTTGGGGAGT
                                    3' LTR
                        ─── 3' LTR MoMLV ───

NarI                         SmaI    KpnI
CTCGGGGCGCCAGTCCTCCGATTGACTGAGTCGCCCGGGTACCCGTGTATCCAATAAACCCTCTTGCAGTTGCATCCGAC
++++++++++|++++++++++|++++++++++|++++++++++|++++++++++|++++++++++|++++++++++|++++ 5040
GAGCCCCGCGGTCAGGAGGCTAACTGACTCAGCGGGCCCATGGGCACATAGGTTATTTGGGAGAACGTCAACGTAGGCTG
                                    3' LTR
                        ─── 3' LTR MoMLV ───

TTGTGGTCTCGCTGTTCCTTGGGAGGGTCTCCTCTGAGTGATTGACTACCCGTCAGCGGGGTCTTTCATTTGGGGGCTC
++++++++++|++++++++++|++++++++++|++++++++++|++++++++++|++++++++++|++++++++++|++++ 5120
AACACCAGAGCGACAAGGAACCCTCCCAGAGGAGACTCACTAACTGATGGGCAGTCGCCCCCAGAAAGTAAACCCCCGAG
═══════════════════════════════════ 3' LTR ═══════════════════════════════════>
                        ─── 3' LTR MoMLV ───

GTCCGGGATCGGGAGACCCCTGCCCAGGGACCACCGACCCACCACCGGGAGGTAAGCTGGCTGCCTCGCGCGTTTCGGTG
++++++++++|++++++++++|++++++++++|++++++++++|++++++++++|++++++++++|++++++++++|++++ 5200
CAGGCCCTAGCCCTCTGGGGACGGGTCCCTGGTGGCTGGGTGGTGGCCCTCCATTCGACCGACGGAGCGCGCAAAGCCAC

ATGACGGTGAAAACCTCTGACACATGCAGCTCCCGGAGACGGTCACAGCTTGTCTGTAAGCGGATGCCGGGAGCAGACAA
++++++++++|++++++++++|++++++++++|++++++++++|++++++++++|++++++++++|++++++++++|++++ 5280
TACTGCCACTTTTGGAGACTGTGTACGTCGAGGGCCTCTGCCAGTGTCGAACAGACATTCGCCTACGGCCCTCGTCTGTT

GCCCGTCAGGGCGCGTCAGCGGGTGTTGGCGGGTGTCGGGGCGCAGCCATGACCCAGTCACGTAGCGATAGCGGAGTGTA
++++++++++|++++++++++|++++++++++|++++++++++|++++++++++|++++++++++|++++++++++|++++ 5360
CGGGCAGTCCCGCGCAGTCGCCCACAACCGCCCACAGCCCCGCGTCGGTACTGGGTCAGTGCATCGCTATCGCCTCACAT

NdeI
TACTGGCTTAACTATGCGGCATCAGAGCAGATTGTACTGAGAGTGCACCATATGCGGTGTGAAATACCGCACAGATGCGT
++++++++++|++++++++++|++++++++++|++++++++++|++++++++++|++++++++++|++++++++++|++++ 5440
ATGACCGAATTGATACGCCGTAGTCTCGTCTAACATGACTCTCACGTGGTATACGCCACACTTTATGGCGTGTCTACGCA

AAGGAGAAAATACCGCATCAGGCGCTCTTCCGCTTCCTCGCTCACTGACTCGCTGCGCTCGGTCGTTCGGCTGCGGCGAG
++++++++++|++++++++++|++++++++++|++++++++++|++++++++++|++++++++++|++++++++++|++++ 5520
TTCCTCTTTTATGGCGTAGTCCGCGAGAAGGCGAAGGAGCGAGTGACTGAGCGACGCGAGCCAGCAAGCCGACGCCGCTC

CGGTATCAGCTCACTCAAAGGCGGTAATACGGTTATCCACAGAATCAGGGGATAACGCAGGAAAGAACATGTGAGCAAAA
++++++++++|++++++++++|++++++++++|++++++++++|++++++++++|++++++++++|++++++++++|++++ 5600
GCCATAGTCGAGTGAGTTTCCGCCATTATGCCAATAGGTGTCTTAGTCCCCTATTGCGTCCTTTCTTGTACACTCGTTTT

GGCCAGCAAAAGGCCAGGAACCGTAAAAAGGCCGCGTTGCTGGCGTTTTTCCATAGGCTCCGCCCCCTGACGAGCATCA
++++++++++|++++++++++|++++++++++|++++++++++|++++++++++|++++++++++|++++++++++|++++ 5680
CCGGTCGTTTTCCGGTCCTTGGCATTTTTCCGGCGCAACGACCGCAAAAAGGTATCCGAGGCGGGGGGACTGCTCGTAGT
```

Wednesday, January 23, 2002 4:08 PM
P-GD1721 pLNC-LCB.MPD (1 > 7472) Site and Sequence FIG. 8 (part 10 of 12)

```
CAAAAATCGACGCTCAAGTCAGAGGTGGCGAAACCCGACAGGACTATAAAGATACCAGGCGTTTCCCCCTGGAAGCTCCC
----+----+----+----+----+----+----+----+----+----+----+----+----+----+----+----+ 5760
GTTTTTAGCTGCGAGTTCAGTCTCCACCGCTTTGGGCTGTCCTGATATTTCTATGGTCCGCAAAGGGGGACCTTCGAGGG

TCGTGCGCTCTCCTGTTCCGACCCTGCCGCTTACCGGATACCTGTCCGCCTTTCTCCCTTCGGGAAGCGTGGCGCTTTCT
----+----+----+----+----+----+----+----+----+----+----+----+----+----+----+----+ 5840
AGCACGCGAGAGGACAAGGCTGGGACGGCGAATGGCCTATGGACAGGCGGAAAGAGGGAAGCCCTTCGCACCGCGAAAGA

CATAGCTCACGCTGTAGGTATCTCAGTTCGGTGTAGGTCGTTCGCTCCAAGCTGGGCTGTGTGCACGAACCCCCCGTTCA
----+----+----+----+----+----+----+----+----+----+----+----+----+----+----+----+ 5920
GTATCGAGTGCGACATCCATAGAGTCAAGCCACATCCAGCAAGCGAGGTTCGACCCGACACACGTGCTTGGGGGGCAAGT

GCCCGACCGCTGCGCCTTATCCGGTAACTATCGTCTTGAGTCCAACCCGGTAAGACACGACTTATCGCCACTGGCAGCAG
----+----+----+----+----+----+----+----+----+----+----+----+----+----+----+----+ 6000
CGGGCTGGCGACGCGGAATAGGCCATTGATAGCAGAACTCAGGTTGGGCCATTCTGTGCTGAATAGCGGTGACCGTCGTC

CCACTGGTAACAGGATTACCAGAGCCAGGTATGTAGGCGGTGCTACAGAGTTCTTGAAGTGGTGGCCTAACTACGGCTAC
----+----+----+----+----+----+----+----+----+----+----+----+----+----+----+----+ 6080
GGTGACCATTGTCCTAATCGTCTCGCTCCATACATCCGCCACGATGTCTCAAGAACTTCACCACCGGATTGATGCCGATG

ACTAGAAGGACAGTATTTGGTATCTGCGCTCTGCTGAAGCCAGTTACCTTCGGAAAAAGAGTTGGTAGCTCTTGATCCGG
----+----+----+----+----+----+----+----+----+----+----+----+----+----+----+----+ 6160
TGATCTTCCTGTCATAAACCATAGACGCGAGACGACTTCGGTCAATGGAAGCCTTTTTCTCAACCATCGAGAACTAGGCC

CAAACAAACCACCGCTGGTAGCGGTGGTTTTTTTGTTTGCAAGCAGCAGATTACGCGCAGAAAAAAAGGATCTCAAGAAG
----+----+----+----+----+----+----+----+----+----+----+----+----+----+----+----+ 6240
GTTTGTTTGGTGGCGACCATCGCCACCAAAAAAACAAACGTTCGTCGTCTAATGCGCGTCTTTTTTTCCTAGAGTTCTTC

BspHI
ATCCTTTGATCTTTTCTACGGGGTCTGACGCTCAGTGGAACGAAAACTCACGTTAAGGGATTTTGGTCATGAGATTATCA
----+----+----+----+----+----+----+----+----+----+----+----+----+----+----+----+ 6320
TAGGAAACTAGAAAAGATGCCCCAGACTGCGAGTCACCTTGCTTTTGAGTGCAATTCCCTAAAACCAGTACTCTAATAGT

DraI                    DraI
AAAAGGATCTTCACCTAGATCCTTTTAAATTAAAAATGAAGTTTTAAATCAATCTAAAGTATATATGAGTAAACTTGGTC
----+----+----+----+----+----+----+----+----+----+----+----+----+----+----+----+ 6400
TTTTCCTAGAAGTGGATCTAGGAAAATTTAATTTTTACTTCAAAATTTAGTTAGATTTCATATATACTCATTTGAACCAG

TGACAGTTACCAATGCTTAATCAGTGAGGCACCTATCTCAGCGATCTGTCTATTTCGTTCATCCATAGTTGCCTGACTCC
----+----+----+----+----+----+----+----+----+----+----+----+----+----+----+----+ 6480
ACTGTCAATGGTTACGAATTAGTCACTCCGTGGATAGAGTCGCTAGACAGATAAAGCAAGTAGGTATCAACGGACTGAGG
   • Trp His Lys Ile Leu Ser Ala Gly Ile Glu Ala Ile Gln Arg Asn Arg Glu Asp Met Thr Ala Gln Ser Gly
   └─────────────────────────── b-Lactamase ────────────────

CCGTCGTGTAGATAACTACGATACGGGAGGGCTTACCATCTGGCCCCAGTGCTGCAATGATACCGCGAGACCCACGCTCA
----+----+----+----+----+----+----+----+----+----+----+----+----+----+----+----+ 6560
GGCAGCACATCTATTGATGCTATGCCCTCCCGAATGGTAGACCGGGGTCACGACGTTACTATGGCGCTCTGGGTGCGAGT
  Thr Thr Tyr Ile Val Val Ile Arg Ser Pro Lys Gly Asp Pro Gly Leu Ala Ala Ile Ile Gly Arg Ser Gly Arg Glu
  ──────────────────────────────── b-Lactamase ────────────────
```

Wednesday, January 23, 2002 4:08 PM
P-GD1721 pLNC-LCB.MPD (1 > 7472) Site and Sequence FIG. 8 (part 11 of 12)

```
CCGGCTCCAGATTTATCAGCAATAAACCAGCCACCCGGAAGGGCCGAGCGCAGAAGTGGTCCTGCAACTTTATCCGCCTC
++++++++++++++++++++++++++++++++++++++++++++++++++++++++++++++++++++++++++++++++ 6640
GGCCGAGGTCTAAATAGTCGTTATTTGGTCGGTCGGCCTTCCCGGCTCGCGTCTTCACCAGGACGTTGAAATAGGCGGAG
 Gly Ala Gly Ser Lys Asp Ala Ile Phe Trp Gly Ala Pro Leu Ala Ser Arg Leu Leu Pro Gly Ala Val Lys Asp Ala Glu
                                        b-Lactamase
```

```
                                                            FspI
CATCCAGTCTATTAATTGTTGCCGGGAAGCTAGAGTAAGTAGTTCGCCAGTTAATAGTTTGCGCAACGTTGTTGCCATTG
++++++++++++++++++++++++++++++++++++++++++++++++++++++++++++++++++++++++++++++++ 6720
GTAGGTCAGATAATTAACAACGGCCCTTCGATCTCATTCATCAAGCGGTCAATTATCAAACGCGTTGCAACAACGGTAAC
 Met Trp Asp Ile Leu Gln Gln Arg Ser Ala Leu Thr Leu Leu Gly Thr Leu Leu Lys Arg Leu Thr Thr Ala Met Ala
                                        b-Lactamase
```

```
        PstI
CTGCAGGCATCGTGGTGTCACGCTCGTCGTTTGGTATGGCTTCATTCAGCTCCGGTTCCCAACCATCAAGGCGAGTTACA
++++++++++++++++++++++++++++++++++++++++++++++++++++++++++++++++++++++++++++++++ 6800
GACGTCCGTAGCACCACAGTGCGAGCAGCAAACCATACCGAAGTAAGTCGAGGCCAAGGGTTGGTACTTCCGCTCAATGT
  Ala Pro Met Thr Thr Asp Arg Glu Asp Asn Pro Ile Ala Glu Asn Leu Glu Pro Glu Trp Arg Asp Leu Arg Thr Val
                                        b-Lactamase
```

```
                                        PvuI
TGATCCCCCATGTTGTGCAAAAAAGCGGTTAGCTCCTTCGGTCCTCCGATCGTTGTCAGAAGTAAGTTGGCCGCAGTGTT
++++++++++++++++++++++++++++++++++++++++++++++++++++++++++++++++++++++++++++++++ 6880
ACTAGGGGGTACAACACGTTTTTTCGCCAATCGAGGAAGCCAGGAGGCTAGCAACAGTCTTCATTCAACCGGCGTCACAA
 His Asp Gly Met Asn His Leu Phe Ala Thr Leu Glu Lys Pro Gly Gly Ile Thr Thr Leu Leu Leu Asn Ala Ala Thr Asn
                                        b-Lactamase
```

```
ATCACTCATGGTTATGGCAGCACTGCATAATTCTCTTACTGTCATGCCATCCGTAAGATGCTTTTCTGTGACTGGTGAGT
++++++++++++++++++++++++++++++++++++++++++++++++++++++++++++++++++++++++++++++++ 6960
TAGTGAGTACCAATACCGTCGTGACGTATTAAGAGAATGACAGTACGGTAGGCATTCTACGAAAAGACACTGACCACTCA
 Asp Ser Met Thr Ile Ala Ala Ser Cys Leu Glu Arg Val Thr Met Gly Asp Thr Leu His Lys Glu Thr Val Pro Ser Tyr
                                        b-Lactamase
```

```
ACTCAACCAAGTCATTCTGAGAATAGTGTATGCGGCGACCGAGTTGCTCTTGCCCGGCGTCAACACGGGATAATACCGCG
++++++++++++++++++++++++++++++++++++++++++++++++++++++++++++++++++++++++++++++++ 7040
TGAGTTGGTTCAGTAAGACTCTTATCACATACGCCGCTGGCTCAACGAGAACGGGCCGCAGTTGTGCCCTATTATGGCGC
 Glu Val Leu Asp Asn Gln Ser Tyr His Ile Arg Arg Gly Leu Gln Glu Gln Gly Ala Asp Val Arg Ser Leu Val Ala
                                        b-Lactamase
```

```
        DraI
CCACATAGCAGAACTTTAAAAGTGCTCATCATTGGAAAACGTTCTTCGGGGCGAAAACTCTCAAGGATCTTACCGCTGTT
++++++++++++++++++++++++++++++++++++++++++++++++++++++++++++++++++++++++++++++++ 7120
GGTGTATCGTCTTGAAATTTTCACGAGTAGTAACCTTTTGCAAGAAGCCCCGCTTTTGAGAGTTCCTAGAATGGCGACAA
 Gly Cys Leu Leu Val Lys Phe Thr Ser Met Met Pro Phe Arg Glu Glu Pro Arg Phe Ser Glu Leu Ile Lys Gly Ser Asn
                                        b-Lactamase
```

```
GAGATCCAGTTCGATGTAACCCACTCGTGCACCCAACTGATCTTCAGCATCTTTTACTTTCACCAGCGTTTCTGGGTGAG
++++++++++++++++++++++++++++++++++++++++++++++++++++++++++++++++++++++++++++++++ 7200
CTCTAGGTCAAGCTACATTGGGTGAGCACGTGGGTTGACTAGAAGTCGTAGAAAATGAAAGTGGTCGCAAAGACCCACTC
 Leu Asp Leu Glu Ile Tyr Gly Val Arg Ala Gly Leu Gln Asp Glu Ala Asp Lys Val Lys Val Leu Thr Glu Pro His Ala
                                        b-Lactamase
```

Wednesday, January 23, 2002 4:08 PM
P-GD1721 pLNC-LCB.MPD (1 > 7472) Site and Sequence FIG. 8 (part 12 of 12)

```
      CAAAAACAGGAAGGCAAAATGCCGCAAAAAGGGAATAAGGGCGACACGGAAATGTTGAATACTCATACTCTTCCTTTTT
      ──────┼─────┼─────┼─────┼─────┼─────┼─────┼─────┼─────┼─────┼─────┼─────┼─────┼──── 7280
      GTTTTTGTCCTTCCGTTTTACGGCGTTTTTCCCTTATTCCCGCTGTGCCTTTACAACTTATGAGTATGAGAAGGAAAAA
         Phe Val Pro Leu Cys Phe Ala Ala Phe Phe Pro Ile Leu Ala Val Arg Phe His Gln Ile Ser Met
         ─────────────────────────────────── b-Lactamase ──────────────────────────────────

BspHI
      CAATATTATTGAAGCATTTATCAGGGTTATTGTCTCATGAGCGGATACATATTTGAATGTATTTAGAAAAATAAACAAAT
      ──────┼─────┼─────┼─────┼─────┼─────┼─────┼─────┼─────┼─────┼─────┼─────┼─────┼──── 7360
      GTTATAATAACTTCGTAAATAGTCCCAATAACAGAGTACTCGCCTATGTATAAACTTACATAAATCTTTTTATTTGTTTA

BspHI
      AGGGGTTCCGCGCACATTTCCCCGAAAAGTGCCACCTGACGTCTAAGAAACCATTATTATCATGACATTAACCTATAAAA
      ──────┼─────┼─────┼─────┼─────┼─────┼─────┼─────┼─────┼─────┼─────┼─────┼─────┼──── 7440
      TCCCCAAGGCGCGTGTAAAGGGGCTTTTCACGGTGGACTGCAGATTCTTTGGTAATAATAGTACTGTAATTGGATATTTT

ATAGGCGTATCACGAGGCCCTTTCGTCTTCAA
      ──────┼─────┼─────┼─────┼──────▶ 7472
      TATCCGCATAGTGCTCCGGGAAAGCAGAAGTT
```

ANTIBODY LIBRARIES

This application is a continuation of U.S. patent application Ser. No. 10/401,000 filed Mar. 27, 2003, which claims the benefit of provisional patent applications 60/368,808, filed Mar. 28, 2002 and 60/371,299, filed Apr. 10, 2002; each of which is herein incorporated by reference in its entirety.

FIELD OF THE INVENTION

The present invention relates to the production of antibody libraries. In particular, the present invention relates to the use of integrating retroviral vectors to generate libraries comprising a plurality of combinations of antibody light chains and heavy chains

BACKGROUND OF THE INVENTION

The pharmaceutical biotechnology industry is based on the production of recombinant proteins in mammalian cells. These proteins are essential to the therapeutic treatment of many diseases and conditions. In particular, antibodies are of increasing importance in human therapy, assay procedures and diagnostic methods. However, methods of identifying antibodies and production of antibodies is often expensive, particularly where monoclonal antibodies are required. Hybridoma technology has traditionally been employed to produce monoclonal antibodies, but these methods are time-consuming and result in isolation and production of limited numbers of specific antibodies. Additionally, relatively small amounts of antibody are produced; consequently, hybridoma methods have not been developed for a large number of antibodies. This is unfortunate as the potential repertoire of immunoglobulins produced in an immunized animal is quite high, on the order of >$10^{10}$, yet hybridoma technology is too complicated and time consuming to adequately screen and develop large number of useful antibodies.

One approach to this problem has been the development of library screening methods for the isolation of antibodies (Huse et al., Science 246:1275 [1989]; McCafferty et al., Nature 348:552 [1990]). Functional antibody fragments have been produced in *E. coli* cells (Better et al., Science 240:1041 [1988]; Sastry et al., PNAS 86:5728 [1989]) as "libraries" of recombinant immunoglobulins containing both heavy and light variable domains (Huse et al., supra). The expressed proteins have antigen-binding affinity comparable to the corresponding natural antibodies. However, it is difficult to isolate high binding populations of antibodies from such libraries and where bacterial cells are used to express specific antibodies, isolation and purification procedures are usually complex and time-consuming.

Combinatorial antibody libraries generated from phage lambda (Huse et al., supra) typically include millions of genes of different antibodies but require complex procedures to screen the library for a selected clone. Methods have been reported for the production of human antibodies using the combinatorial library approach in filamentous bacteriophage. A major disadvantage of such methods is the need to rely on initial isolation of the antibody DNA from peripheral human blood to prepare the library. Moreover, the generation of human antibodies to toxic compounds is not feasible owing to risks involved in immunizing a human with these compounds.

Currently the most widely used approach for screening polypeptide libraries is to display polypeptides on the surface of filamentous bacteriophage. The polypeptides are expressed as fusions to the N-terminus of a coat protein. As the phage assembles, the fusion proteins are incorporated in the viral coat so that the polypeptides become displayed on the bacteriophage surface. Each polypeptide produced is displayed on the surface of one or more of the bacteriophage particles and subsequently tested for specific ligand interactions. While this approach appears attractive, there are numerous problems, including difficulties of enriching positive clones from phage libraries. Enrichment procedures are based on selective binding and elution onto a solid surface such as an immobilized receptor. Unfortunately, avidity effects arise due to multivalent binding of the phage and the general tendency of phage to contain two or more copies of the displayed polypeptide. The binding to the receptor surface therefore does not depend solely on the strength of interaction between the receptor and the displayed polypeptide. This causes difficulties in the identification of clones with high affinity for the receptor.

Thus, the art is in need of efficient methods of generating and screening antibody libraries containing large numbers of antibodies.

SUMMARY OF THE INVENTION

The present invention relates to the production of antibody libraries. In particular, the present invention relates to the use of integrating retroviral vectors to generate libraries comprising a plurality of combinations of antibody light chains and heavy chains.

For example, in some embodiments, the present invention provides an antibody library comprising at least $10^2$ cells, wherein each cell comprises at least one integrated retroviral vector expressing an antibody light chain. In some embodiments, the antibody library expresses at least $10^2$, preferably at least $10^3$, even more preferably at least $10^4$, and still more preferably at least $10^5$ unique antibody light chains. In some preferred embodiments, each of the cells comprises exactly one of the integrated retroviral vectors.

The present invention also provides an antibody library comprising at least $10^2$ cells, wherein each cell comprises at least one integrated retroviral vector expressing an antibody heavy chain. In some embodiments, the antibody library expresses at least $10^2$, preferably at least $10^3$, even more preferably at least $10^4$, and still more preferably at least $10^5$ unique antibody heavy chains. In some preferred embodiments, each of the cells comprises exactly one of the integrated retroviral vectors.

The present invention further provides an antibody library comprising at least $10^2$ cells, wherein each cell comprises at least one of a first integrated retroviral vector and at least one of a second integrated retroviral vector, wherein the first retroviral vector expresses an antibody light chain and the second retroviral vector expresses an antibody heavy chain, and wherein the antibody light chain and the antibody heavy chain associate to form an antibody. In some embodiments, the first and second integrated vectors are separately integrated. In some embodiments, the antibody library expresses at least $10^2$, preferably at least $10^3$, even more preferably at least $10^4$, and still more preferably at least $10^5$ unique antibodies. In some preferred embodiments, the cell comprises exactly one of the first integrated retroviral and exactly one of the second integrated retroviral vector.

The present invention additionally provides a retroviral particle library comprising at least $10^2$ retroviral particles, wherein each retroviral particle comprises one antibody light chain gene. In some embodiments, the retroviral particle library expresses at least $10^2$, preferably at least $10^3$, even more preferably at least $10^4$, and still more preferably at least $10^5$ unique antibody light chain genes.

In other embodiments, the present invention provides a retroviral particle library comprising at least $10^2$ retroviral particles, wherein each retroviral particle comprises one antibody heavy chain gene. In some embodiments, the retroviral particle library expresses at least $10^2$, preferably at least $10^3$, even more preferably at least $10^4$, and still more preferably at least $10^5$ unique antibody heavy chain genes.

In still further embodiments, the present invention provides a retroviral particle library comprising at least $10^2$ retroviral particles, wherein each retroviral particle comprises at least one antibody gene selected from the group consisting of antibody heavy chain genes and antibody light chain genes. In some embodiments, the retroviral particle library expresses at least $10^2$, preferably at least $10^3$, even more preferably at least $10^4$, and still more preferably at least $10^5$ unique antibody genes. In some preferred embodiments, each retroviral particle comprises one antibody heavy chain gene and one antibody light chain gene.

In yet other embodiments, the present invention provides a plasmid library comprising at least $10^2$ plasmids, wherein each plasmid comprises one antibody heavy chain gene inserted into a retroviral vector backbone. In some embodiments, the plasmid library expresses at least $10^2$, preferably at least $10^3$, even more preferably at least $10^4$, and still more preferably at least $10^5$ unique antibody heavy chain genes.

In still additional embodiments, the present invention provides a plasmid library comprising at least $10^2$ plasmids, wherein each plasmid comprises one antibody light chain gene inserted into a retroviral vector backbone. In some embodiments, the plasmid library expresses at least $10^2$, preferably at least $10^3$, even more preferably at least $10^4$, and still more preferably at least $10^5$ unique antibody light chain genes.

In certain embodiments, the present invention provides a plasmid library comprising at least $10^2$ plasmids, wherein each plasmid comprises at least one antibody gene selected from the group consisting of antibody heavy chain gene and antibody light chain gene. In some embodiments, the plasmid library expresses at least $10^2$, preferably at least $10^3$, even more preferably at least $10^4$, and still more preferably at least $10^5$ unique antibody genes. In some preferred embodiments, each plasmid comprises one antibody heavy chain gene and one antibody light chain gene.

The present invention also provides a method of generating antibody libraries, comprising: providing a plurality of first integratable retroviral particles, wherein each of the plurality of retroviral particles comprises one antibody light chain gene; a plurality of second integratable retroviral particles, wherein each of the plurality of retroviral particles comprises one antibody heavy chain gene; and a host cell comprising a genome; and contacting the plurality of host cell with the plurality of first and second integratable retroviral particles under conditions such that at least one of the plurality of first integratable retroviral particles and at least one of the plurality of second integratable retroviral particles integrate into the genome of the host cell to generate an antibody library. In some embodiments, the plurality of first integratable retroviral particles further comprises a first selectable marker, and the plurality of second integratable retroviral particles further comprises a second selectable marker. In some embodiments, the contacting further comprises selecting for the presence of the first and second selectable markers. In some embodiments, the antibody library comprises at least $10^2$, preferably at least $10^3$, even more preferably at least $10^4$, and still more preferably at least $10^5$ unique antibodies. In some preferred embodiments, exactly one of the plurality of first integratable retroviral particles and exactly one of the plurality of second integratable retroviral particles integrate into the genome of the host cell. In some embodiments, the method further comprises the step of screening the antibody library. In some embodiments, the screening comprises detecting the ability of antibodies in the antibody library to bind to a pre-selected antigen. In some embodiments, the antibodies are bound to the membrane of the host cell and the detecting comprises fluorescence activated cell sorting. In certain embodiments, the antibodies are secreted and the detecting comprises a solution-based detection assay. In some embodiments, the antibodies are diluted into individual containers prior to said detecting. In some embodiments, the solution based assay is selected from the group consisting of radioimmunoassay, ELISA (enzyme-linked immunosorbant assay), "sandwich" immunoassays, immunoradiometric assays, immunoprecipitation reactions, agglutination assays (e.g., hemagglutination assays, etc.), complement fixation assays, immunofluorescence assays, and protein A assays.

The present invention further provides a method of screening antibody libraries, comprising: providing an antibody library comprising at least $10^2$ unique antibodies; and a pre-selected antigen; and screening the antibody library, wherein the screening comprises detecting the ability of the at least $10^2$ unique antibodies to bind to the pre-selected antigen. In some embodiments, the antibody library comprises at least $10^2$, preferably at least $10^3$, even more preferably at least $10^4$, and still more preferably at least $10^5$ unique antibodies. In some embodiments, the antibodies are bound to the membrane of a host cell and the detecting comprises fluorescence activated cell sorting. In certain embodiments, the antibodies are secreted and the detecting comprises a solution-based detection assay. In some embodiments, the antibodies are diluted into individual containers prior to said detecting. In some embodiments, the solution based assay is selected from the group consisting of radioimmunoassay, ELISA (enzyme-linked immunosorbant assay), "sandwich" immunoassays, immunoradiometric assays, immunoprecipitation reactions, agglutination assays (e.g., hemagglutination assays, etc.), complement fixation assays, immunofluorescence assays, and protein A assays.

The present invention additionally provides a method, comprising providing a plurality of first integratable retroviral particles, wherein each of the plurality of retroviral particles comprises one antibody light chain gene; a plurality of second integratable retroviral particles, wherein each of the plurality of retroviral particles comprises one antibody heavy chain gene; and a host cell comprising a genome; and a pre-selected antigen; and contacting the plurality of host cell with the plurality of first and second integratable retroviral particles under conditions such that at least one of the plurality of first integratable retroviral particles and at least one of the plurality of second integratable retroviral particles integrate into the genome of the host cell to generate an antibody library comprising a plurality of antibodies; and screening the antibody library, wherein the screening comprises detecting the ability of the antibodies to bind to the pre-selected antigen. In some embodiments, the antibody library comprises at least $10^2$, preferably at least $10^3$, even more preferably at least $10^4$, and still more preferably at least $10^5$ unique antibodies. In some embodiments, the plurality of first integratable retroviral particles further comprises a first selectable marker, and the plurality of second integratable retroviral particles further comprises a second selectable marker. In some embodiments, the contacting further comprises selecting for the presence of the first and second selectable markers. In some embodiments, the antibodies are bound to the membrane of the host cell and the detecting comprises fluorescence activated cell sorting. In some embodiments, the antibodies are secreted and the detecting comprises a solution-based detection assay. In some embodiments, the antibodies are diluted into individual containers prior to said detecting. In some embodiments, the solution based assay is selected from the group consisting of radioimmunoassay, ELISA (enzyme-linked immunosorbant assay), "sandwich" immunoassays, immunoradiometric assays, immunoprecipitation reactions, agglutination assays (e.g., hemagglutination assays, etc.), complement fixation assays, immunofluorescence assays, and protein A assays.

DESCRIPTION OF THE FIGURES

FIG. 5 shows the nucleic acid sequence of pLBC-L2HCF (SEQ ID NO:1).

FIG. 6 shows the nucleic acid sequence of pLBC-M4HCF (SEQ ID NO:2).

FIG. 7 shows the nucleic acid sequence of pLNC-L2LC (SEQ ID NO:3).

FIG. 8 shows the nucleic acid sequence of pLNC-M4LC (SEQ ID NO:4).

DEFINITIONS

Figure 1:
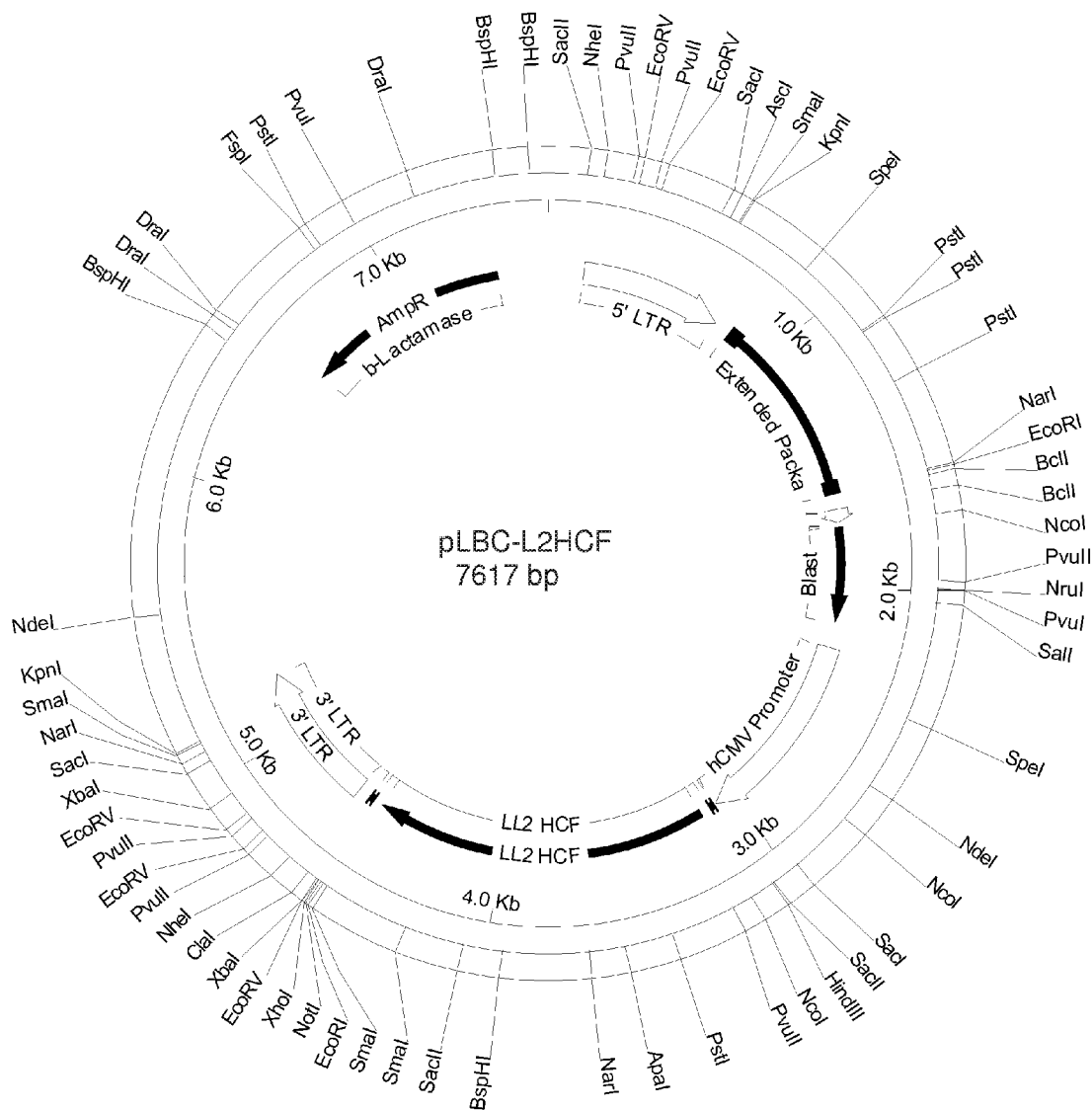
FIG. 1 shows a plasmid map of pLBC-L2HCF.

To facilitate understanding of the invention, a number of terms are defined below.

As used herein, the term "host cell" refers to any eukaryotic cell (e.g., mammalian cells, avian cells, amphibian cells, plant cells, fish cells, and insect cells), whether located in vitro or in vivo.

As used herein, the term "cell culture" refers to any in vitro culture of cells. Included within this term are continuous cell lines (e.g., with an immortal phenotype), primary cell cultures, finite cell lines (e.g., non-transformed cells), and any other cell population maintained in vitro, including oocytes and embryos.

As used herein, the term "vector" refers to any genetic element, such as a plasmid, phage, transposon, cosmid, chromosome, virus, virion, etc., which is capable of replication when associated with the proper control elements and which can transfer gene sequences between cells. Thus, the term includes cloning and expression vehicles, as well as viral vectors.

As used herein, the term "integrating vector" refers to a vector whose integration or insertion into a nucleic acid (e.g., a chromosome) is accomplished via an integrase. Examples of "integrating vectors" include, but are not limited to, retroviral vectors, transposons, and adeno associated virus vectors.

As used herein, the term "integrated" refers to a vector that is stably inserted into the genome (i.e., into a chromosome) of a host cell.

As used herein, the term "multiplicity of infection" or "MOI" refers to the ratio of integrating vectors:host cells used during transfection or transduction of host cells. For example, if 1,000,000 vectors are used to transduce 100,000 host cells, the multiplicity of infection is 10. The use of this term is not limited to events involving transduction, but instead encompasses introduction of a vector into a host by methods such as lipofection, microinjection, calcium phosphate precipitation, and electroporation.

As used herein, the term "genome" refers to the genetic material (e.g., chomosomes) of an organism.

The term "nucleotide sequence of interest" refers to any nucleotide sequence (e.g., RNA or DNA), the manipulation of which may be deemed desirable for any reason (e.g., treat disease, confer improved qualities, expression of a protein of interest in a host cell, expression of a ribozyme, etc.), by one of ordinary skill in the art. Such nucleotide sequences include, but are not limited to, coding sequences of structural genes (e.g., reporter genes, selection marker genes, oncogenes, drug resistance genes, growth factors, etc.), and non-coding regulatory sequences which do not encode an mRNA or protein product (e.g., promoter sequence, polyadenylation sequence, termination sequence, enhancer sequence, etc.).

As used herein, the term "protein of interest" refers to a protein encoded by a nucleic acid of interest.

As used herein, the term "signal protein" refers to a protein that is co-expressed with a protein of interest and which, when detected by a suitable assay, provides indirect evidence of expression of the protein of interest. Examples of signal proteins useful in the present invention include, but are not limited to, beta-galactosidase, beta-lactamase, green fluorescent protein, and luciferase.

As used herein, the term "exogenous gene" refers to a gene that is not naturally present in a host organism or cell, or is artificially introduced into a host organism or cell.

The term "gene" refers to a nucleic acid (e.g., DNA or RNA) sequence that comprises coding sequences necessary for the production of a polypeptide or precursor (e.g., proinsulin). The polypeptide can be encoded by a full length coding sequence or by any portion of the coding sequence so long as the desired activity or functional properties (e.g., enzymatic activity, ligand binding, signal transduction, etc.) of the full-length or fragment are retained. The term also encompasses the coding region of a structural gene and includes sequences located adjacent to the coding region on both the 5' and 3' ends for a distance of about 1 kb or more on either end such that the gene corresponds to the length of the full-length mRNA. The sequences that are located 5' of the coding region and which are present on the mRNA are referred to as 5' untranslated sequences. The sequences that are located 3' or downstream of the coding region and which are present on the mRNA are referred to as 3' untranslated sequences. The term "gene" encompasses both cDNA and genomic forms of a gene. A genomic form or clone of a gene contains the coding region interrupted with non-coding sequences termed "introns" or "intervening regions" or "intervening sequences." Introns are segments of a gene that are transcribed into nuclear RNA (hnRNA); introns may contain regulatory elements such as enhancers. Introns are removed or "spliced out" from the nuclear or primary transcript; introns therefore are absent in the messenger RNA (mRNA) transcript. The mRNA functions during translation to specify the sequence or order of amino acids in a nascent polypeptide.

As used herein, the term "gene expression" refers to the process of converting genetic information encoded in a gene into RNA (e.g., mRNA, rRNA, tRNA, or snRNA) through "transcription" of the gene (i.e., via the enzymatic action of an RNA polymerase), and for protein encoding genes, into protein through "translation" of mRNA. Gene expression can be regulated at many stages in the process. "Up-regulation" or "activation" refers to regulation that increases the production of gene expression products (i.e., RNA or protein), while "down-regulation" or "repression" refers to regulation that decrease production. Molecules (e.g., transcription factors) that are involved in up-regulation or down-regulation are often called "activators" and "repressors," respectively.

Where "amino acid sequence" is recited herein to refer to an amino acid sequence of a naturally occurring protein molecule, "amino acid sequence" and like terms, such as "polypeptide" or "protein" are not meant to limit the amino acid sequence to the complete, native amino acid sequence associated with the recited protein molecule.

As used herein, the terms "nucleic acid molecule encoding," "DNA sequence encoding," "DNA encoding," "RNA sequence encoding," and "RNA encoding" refer to the order or sequence of deoxyribonucleotides or ribonucleotides along a strand of deoxyribonucleic acid or ribonucleic acid. The order of these deoxyribonucleotides or ribonucleotides determines the order of amino acids along the polypeptide (protein) chain. The DNA or RNA sequence thus codes for the amino acid sequence.

As used herein, the term "variant," when used in reference to a protein, refers to proteins encoded by partially homologous nucleic acids so that the amino acid sequence of the proteins varies. As used herein, the term "variant" encompasses proteins encoded by homologous genes having both conservative and nonconservative amino acid substitutions that do not result in a change in protein function, as well as proteins encoded by homologous genes having amino acid substitutions that cause decreased (e.g., null mutations) protein function or increased protein function.

A gene may produce multiple RNA species that are generated by differential splicing of the primary RNA transcript. cDNAs that are splice variants of the same gene will contain regions of sequence identity or complete homology (representing the presence of the same exon or portion of the same exon on both cDNAs) and regions of complete non-identity (for example, representing the presence of exon "A" on cDNA 1 wherein cDNA 2 contains exon "B" instead). Because the two cDNAs contain regions of sequence identity they will both hybridize to a probe derived from the entire gene or portions of the gene containing sequences found on both cDNAs; the two splice variants are therefore substantially homologous to such a probe and to each other.

The terms "in operable combination," "in operable order," and "operably linked" as used herein refer to the linkage of nucleic acid sequences in such a manner that a nucleic acid molecule capable of directing the transcription of a given gene and/or the synthesis of a desired protein molecule is produced. The term also refers to the linkage of amino acid sequences in such a manner so that a functional protein is produced.

As used herein, the term "selectable marker" refers to a gene that encodes an enzymatic activity that confers the ability to grow in medium lacking what would otherwise be an essential nutrient (e.g. the HIS3 gene in yeast cells); in addition, a selectable marker may confer resistance to an antibiotic or drug upon the cell in which the selectable marker is expressed. Selectable markers may be "dominant"; a dominant selectable marker encodes an enzymatic activity that can be detected in any eukaryotic cell line. Examples of dominant selectable markers include the bacterial aminoglycoside 3' phosphotransferase gene (also referred to as the neo gene) that confers resistance to the drug G418 in mammalian cells, the bacterial hygromycin G phosphotransferase (hyg) gene that confers resistance to the antibiotic hygromycin and the bacterial xanthine-guanine phosphoribosyl transferase gene (also referred to as the gpt gene) that confers the ability to grow in the presence of mycophenolic acid. Other selectable markers are not dominant in that their use must be in conjunction with a cell line that lacks the relevant enzyme activity. Examples of non-dominant selectable markers include the thymidine kinase (tk) gene that is used in conjunction with tk$^-$ cell lines, the CAD gene which is used in conjunction with CAD-deficient cells and the mammalian hypoxanthine-guanine phosphoribosyl transferase (hprt) gene which is used in conjunction with hprt$^-$ cell lines. A review of the use of selectable markers in mammalian cell lines is provided in Sambrook, J. et al., *Molecular Cloning: A Laboratory Manual,* 2nd ed., Cold Spring Harbor Laboratory Press, New York (1989) pp. 16.9-16.15.

As used herein, the term "selecting for the presence of said first and second selectable markers" refers to culturing cells transducted with a retrovirus comprising a selectable marker under conditions that require the presence of the selectable marker in order for growth (e.g., culturing cells in the presence of a particular nutrient, antibiotic or drug).

As used herein, the term "regulatory element" refers to a genetic element that controls some aspect of the expression of nucleic acid sequences. For example, a promoter is a regulatory element that facilitates the initiation of transcription of an operably linked coding region. Other regulatory elements are splicing signals, polyadenylation signals, termination signals, RNA export elements, internal ribosome entry sites, etc. (defined infra).

Transcriptional control signals in eukaryotes comprise "promoter" and "enhancer" elements. Promoters and enhancers consist of short arrays of DNA sequences that interact specifically with cellular proteins involved in transcription (Maniatis et al., Science 236:1237 [1987]). Promoter and enhancer elements have been isolated from a variety of eukaryotic sources including genes in yeast, insect and mammalian cells, and viruses (analogous control elements, i.e., promoters, are also found in prokaryotes). The selection of a particular promoter and enhancer depends on what cell type is to be used to express the protein of interest. Some eukaryotic promoters and enhancers have a broad host range while others are functional in a limited subset of cell types (for review see, Voss et al., Trends Biochem. Sci., 11:287 [1986]; and Maniatis et al., supra). For example, the SV40 early gene enhancer is very active in a wide variety of cell types from many mammalian species and has been widely used for the expression of proteins in mammalian cells (Dijkema et al., EMBO J. 4:761 [1985]). Two other examples of promoter/enhancer elements active in a broad range of mammalian cell types are those from the human elongation factor 1α gene (Uetsuki et al., J. Biol. Chem., 264:5791; Kim et al., Gene 91:217 [1990]; and Mizushima and Nagata, Nuc. Acids. Res., 18:5322 [1990]) and the long terminal repeats of the Rous sarcoma virus (Gorman et al., Proc. Natl. Acad. Sci. USA 79:6777 [1982]) and the human cytomegalovirus (Boshart et al., Cell 41:521 [1985]).

As used herein, the term "promoter/enhancer" denotes a segment of DNA which contains sequences capable of providing both promoter and enhancer functions (i.e., the functions provided by a promoter element and an enhancer element, see above for a discussion of these functions). For example, the long terminal repeats of retroviruses contain both promoter and enhancer functions. The enhancer/promoter may be "endogenous" or "exogenous" or "heterologous." An "endogenous" enhancer/promoter is one that is naturally linked with a given gene in the genome. An "exogenous" or "heterologous" enhancer/promoter is one that is placed in juxtaposition to a gene by means of genetic manipulation (i.e., molecular biological techniques such as cloning and recombination) such that transcription of that gene is directed by the linked enhancer/promoter.

Regulatory elements may be tissue specific or cell specific. The term "tissue specific" as it applies to a regulatory element refers to a regulatory element that is capable of directing selective expression of a nucleotide sequence of interest to a specific type of tissue (e.g., liver) in the relative absence of expression of the same nucleotide sequence of interest in a different type of tissue (e.g., lung).

Tissue specificity of a regulatory element may be evaluated by, for example, operably linking a reporter gene to a promoter sequence (which is not tissue-specific) and to the regulatory element to generate a reporter construct, introducing the reporter construct into the genome of an animal such that the reporter construct is integrated into every tissue of the resulting transgenic animal, and detecting the expression of the reporter gene (e.g., detecting mRNA, protein, or the activity of a protein encoded by the reporter gene) in different tissues of the transgenic animal. The detection of a greater level of expression of the reporter gene in one or more tissues relative to the level of expression of the reporter gene in other tissues shows that the regulatory element is "specific" for the tissues in which greater levels of expression are detected. Thus, the term "tissue-specific" (e.g., liver-specific) as used herein is a relative term that does not require absolute specificity of expression. In other words, the term "tissue-specific" does not require that one tissue have extremely high levels of expression and another tissue have no expression. It is sufficient that expression is greater in one tissue than another. By contrast, "strict" or "absolute" tissue-specific expression is meant to indicate expression in a single tissue type (e.g., liver) with no detectable expression in other tissues.

The term "cell type specific" as applied to a regulatory element refers to a regulatory element that is capable of directing selective expression of a nucleotide sequence of interest in a specific type of cell in the relative absence of expression of the same nucleotide sequence of interest in a different type of cell within the same tissue. The term "cell type specific" when applied to a regulatory element also means a regulatory element capable of promoting selective expression of a nucleotide sequence of interest in a region within a single tissue.

Cell type specificity of a regulatory element may be assessed using methods well known in the art (e.g., immunohistochemical staining and/or Northern blot analysis). Briefly, for immunohistochemical staining, tissue sections are embedded in paraffin, and paraffin sections are reacted with a primary antibody specific for the polypeptide product encoded by the nucleotide sequence of interest whose expression is regulated by the regulatory element. A labeled (e.g., peroxidase conjugated) secondary antibody specific for the primary antibody is allowed to bind to the sectioned tissue and specific binding detected (e.g., with avidin/biotin) by microscopy. Briefly, for Northern blot analysis, RNA is isolated from cells and electrophoresed on agarose gels to fractionate the RNA according to size followed by transfer of the RNA from the gel to a solid support (e.g., nitrocellulose or a nylon membrane). The immobilized RNA is then probed with a labeled oligo-deoxyribonucleotide probe or DNA probe to detect RNA species complementary to the probe used. Northern blots are a standard tool of molecular biologists.

The term "promoter," "promoter element," or "promoter sequence" as used herein, refers to a DNA sequence which when ligated to a nucleotide sequence of interest is capable of controlling the transcription of the nucleotide sequence of interest into mRNA. A promoter is typically, though not necessarily, located 5' (i.e., upstream) of a nucleotide sequence of interest whose transcription into mRNA it controls, and provides a site for specific binding by RNA polymerase and other transcription factors for initiation of transcription.

Promoters may be constitutive or regulatable. The term "constitutive" when made in reference to a promoter means that the promoter is capable of directing transcription of an operably linked nucleic acid sequence in the absence of a stimulus (e.g., heat shock, chemicals, etc.). In contrast, a "regulatable" promoter is one that is capable of directing a level of transcription of an operably linked nucleic acid sequence in the presence of a stimulus (e.g., heat shock, chemicals, etc.) that is different from the level of transcription of the operably linked nucleic acid sequence in the absence of the stimulus.

The presence of "splicing signals" on an expression vector often results in higher levels of expression of the recombinant transcript. Splicing signals mediate the removal of introns from the primary RNA transcript and consist of a splice donor and acceptor site (Sambrook et al., *Molecular Cloning: A Laboratory Manual*, 2nd ed., Cold Spring Harbor Laboratory Press, New York [1989], pp. 16.7-16.8). A commonly used splice donor and acceptor site is the splice junction from the 16S RNA of SV40.

Efficient expression of recombinant DNA sequences in eukaryotic cells requires expression of signals directing the efficient termination and polyadenylation of the resulting transcript. Transcription termination signals are generally found downstream of the polyadenylation signal and are a few hundred nucleotides in length. The term "poly A site" or "poly A sequence" as used herein denotes a DNA sequence that directs both the termination and polyadenylation of the nascent RNA transcript. Efficient polyadenylation of the recombinant transcript is desirable as transcripts lacking a poly A tail are unstable and are rapidly degraded. The poly A signal utilized in an expression vector may be "heterologous" or "endogenous." An endogenous poly A signal is one that is found naturally at the 3' end of the coding region of a given gene in the genome. A heterologous poly A signal is one that is isolated from one gene and placed 3' of another gene. A commonly used heterologous poly A signal is the SV40 poly A signal. The SV40 poly A signal is contained on a 237 bp BamHI/BclI restriction fragment and directs both termination and polyadenylation (Sambrook, supra, at 16.6-16.7).

Eukaryotic expression vectors may also contain "viral replicons" or "viral origins of replication." Viral replicons are viral DNA sequences that allow for the extrachromosomal replication of a vector in a host cell expressing the appropriate replication factors. Vectors that contain either the SV40 or polyoma virus origin of replication replicate to high "copy number" (up to $10^4$ copies/cell) in cells that express the appropriate viral T antigen. Vectors that contain the replicons from bovine papillomavirus or Epstein-Barr virus replicate extrachromosomally at "low copy number" (~100 copies/cell). However, it is not intended that expression vectors be limited to any particular viral origin of replication.

As used herein, the term "long terminal repeat" of "LTR" refers to transcriptional control elements located in or isolated from the U3 region 5' and 3' of a retroviral genome. As is known in the art, long terminal repeats may be used as control elements in retroviral vectors, or isolated from the retroviral genome and used to control expression from other types of vectors.

As used herein, the terms "RNA export element" or "Pre-mRNA Processing Enhancer (PPE)" refer to 3' and 5' cis-acting post-transcriptional regulatory elements that enhance export of RNA from the nucleus. "PPE" elements include, but are not limited to Mertz sequences (described in U.S. Pat. Nos. 5,914,267 and 5,686,120, all of which are incorporated herein by reference) and woodchuck mRNA processing enhancer (WPRE; WO99/14310 and U.S. Pat. No. 6,136,597, each of which is incorporated herein by reference).

As used herein, the term "polycistronic" refers to an mRNA encoding more than polypeptide chain (See, e.g., WO 93/03143, WO 88/05486, and European Pat. No. 117058, all of which are incorporated herein by reference). Likewise, the term "arranged in polycistronic sequence" refers to the arrangement of genes encoding two different polypeptide chains in a single mRNA.

As used herein, the term "internal ribosome entry site" or "IRES" refers to a sequence located between polycistronic genes that permits the production of the expression product originating from the second gene by internal initiation of the translation of the dicistronic mRNA. Examples of internal ribosome entry sites include, but are not limited to, those derived from foot and mouth disease virus (FDV), encephalomyocarditis virus, poliovirus and RDV (Scheper et al., Biochem. 76: 801-809 [1994]; Meyer et al., J. Virol. 69: 2819-2824 [1995]; Jang et al., 1988, J. Virol. 62: 2636-2643 [1998]; Haller et al., J. Virol. 66: 5075-5086 [1995]). Vectors incorporating IRES's may be assembled as is known in the art. For example, a retroviral vector containing a polycistronic sequence may contain the following elements in operable association: nucleotide polylinker, gene of interest, an internal ribosome entry site and a mammalian selectable marker or another gene of interest. The polycistronic cassette is situated within the retroviral vector between the 5' LTR and the 3' LTR at a position such that transcription from the 5' LTR promoter transcribes the polycistronic message cassette. The transcription of the polycistronic message cassette may also be driven by an internal promoter (e.g., cytomegalovirus promoter) or an inducible promoter, which may be preferable depending on the use. The polycistronic message cassette can further comprise a cDNA or genomic DNA (gDNA) sequence operatively associated within the polylinker. Any mammalian selectable marker can be utilized as the polycistronic message cassette mammalian selectable marker. Such mammalian selectable markers are well known to those of skill in the art and can include, but are not limited to, kanamycin/G418, hygromycin B or mycophenolic acid resistance markers.

As used herein, the term "retrovirus" refers to a retroviral particle which is capable of entering a cell (i.e., the particle contains a membrane-associated protein such as an envelope protein or a viral G glycoprotein which can bind to the host cell surface and facilitate entry of the viral particle into the cytoplasm of the host cell) and integrating the retroviral genome (as a double-stranded provirus) into the genome of the host cell. The term "retrovirus" encompasses Oncovirinae (e.g., Moloney murine leukemia virus (MoMOLV), Moloney murine sarcoma virus (MoMSV), and Mouse mammary tumor virus (MMTV), Spumavirinae, and Lentivirinae (e.g., Human immunodeficiency virus, Simian immunodeficiency virus, Equine infection anemia virus, and Caprine arthritis-encephalitis virus; See, e.g., U.S. Pat. Nos. 5,994,136 and 6,013,516, both of which are incorporated herein by reference).

As used herein, the term "retroviral vector" refers to a retrovirus that has been modified to express a gene of interest. Retroviral vectors can be used to transfer genes efficiently into host cells by exploiting the viral infectious process. Foreign or heterologous genes cloned (i.e., inserted using molecular biological techniques) into the retroviral genome can be delivered efficiently to host cells that are susceptible to infection by the retrovirus. Through well known genetic manipulations, the replicative capacity of the retroviral genome can be destroyed. The resulting replication-defective vectors can be used to introduce new genetic material to a cell but they are unable to replicate. A helper virus or packaging cell line can be used to permit vector particle assembly and egress from the cell. Such retroviral vectors comprise a replication-deficient retroviral genome containing a nucleic acid sequence encoding at least one gene of interest (i.e., a polycistronic nucleic acid sequence can encode more than one gene of interest), a 5' retroviral long terminal repeat (5' LTR); and a 3' retroviral long terminal repeat (3' LTR).

The term "pseudotyped retroviral vector" refers to a retroviral vector containing a heterologous membrane protein. The term "membrane-associated protein" refers to a protein (e.g., a viral envelope glycoprotein or the G proteins of viruses in the Rhabdoviridae family such as VSV, Piry, Chandipura and Mokola), which is associated with the membrane surrounding a viral particle; these membrane-associated proteins mediate the entry of the viral particle into the host cell. The membrane associated protein may bind to specific cell surface protein receptors, as is the case for retroviral envelope proteins or the membrane-associated protein may interact with a phospholipid component of the plasma membrane of the host cell, as is the case for the G proteins derived from members of the Rhabdoviridae family.

As used herein, the term "retroviral particle" refers to infections viral particles generated by packaging a retroviral vector in a packaging cell line (See e.g., Example 3).

As used herein, the term "retroviral particle library" refers to a plurality of retroviral particles comprising a plurality of unique antibody genes (e.g., heavy or light chain genes). In preferred embodiments, retroviral particle libraries comprise at least $10^2$, more preferably, at least $10^3$, even more preferably at least $10^4$, and still further more preferably, at least $10^5$ unique heavy and/or light chain genes.

As used herein, the term "plasmid" refers to a circular, extra-chromosomal nucleic acid molecule capable of autonomous replication in a host cell. In preferred embodiments, plasmids of the present invention further comprise retroviral LTRs and one or more heavy and/or light chain genes inserted between the retroviral LTRs.

As used herein, the term "plasmid library" refers to a plurality of plasmids comprising a plurality of unique antibody genes (e.g., heavy or light chain genes) inserted between retroviral LTRs. In preferred embodiments, retroviral particle libraries comprise at least $10^2$, more preferably, at least $10^3$, even more preferably at least $10^4$, and still further more preferably, at least $10^5$ unique heavy and/or light chain genes.

The term "heterologous membrane-associated protein" refers to a membrane-associated protein that is derived from a virus that is not a member of the same viral class or family as that from which the nucleocapsid protein of the vector particle is derived. "Viral class or family" refers to the taxonomic rank of class or family, as assigned by the International Committee on Taxonomy of Viruses.

The term "Rhabdoviridae" refers to a family of enveloped RNA viruses that infect animals, including humans, and plants. The Rhabdoviridae family encompasses the genus *Vesiculovirus* that includes vesicular stomatitis virus (VSV), Cocal virus, Piry virus, Chandipura virus, and Spring viremia of carp virus (sequences encoding the Spring viremia of carp virus are available under GenBank accession number U18101). The G proteins of viruses in the *Vesiculovirus* genera are virally-encoded integral membrane proteins that form externally projecting homotrimeric spike glycoproteins complexes that are required for receptor binding and membrane fusion. The G proteins of viruses in the *Vesiculovirus* genera have a covalently bound palmititic acid ($C_{16}$) moiety. The amino acid sequences of the G proteins from the *Vesiculoviruses* are fairly well conserved. For example, the Piry virus G proteins share about 38% identity and about 55% similarity with the VSV G proteins (several strains of VSV are known, e.g., Indiana, N.J., Orsay, San Juan, etc., and their G proteins are highly homologous). The Chandipura virus G protein and the VSV G proteins share about 37% identity and 52% similarity. Given the high degree of conservation (amino acid sequence) and the related functional characteristics (e.g., binding of the virus to the host cell and fusion of membranes, including syncytia formation) of the G proteins of the *Vesiculoviruses*, the G proteins from non-VSV *Vesiculoviruses* may be used in place of the VSV G protein for the pseudotyping of viral particles. The G proteins of the Lyssa viruses (another genera within the Rhabdoviridae family) also share a fair degree of conservation with the VSV G proteins and function in a similar manner (e.g., mediate fusion of membranes) and therefore may be used in place of the VSV G protein for the pseudotyping of viral particles. The Lyssa viruses include the Mokola virus and the Rabies viruses (several strains of Rabies virus are known and their G proteins have been cloned and sequenced). The Mokola virus G protein shares stretches of homology (particularly over the extracellular and transmembrane domains) with the VSV G proteins, which show about 31% identity, and 48% similarity with the VSV G proteins. Preferred G proteins share at least 25% identity, preferably at least 30% identity and most preferably at least 35% identity with the VSV G proteins. The VSV G protein from which New Jersey strain (the sequence of this G protein is provided in GenBank accession numbers M27165 and M21557) is employed as the reference VSV G protein.

As used herein, the term "lentivirus vector" refers to retroviral vectors derived from the Lentiviridae family (e.g., human immunodeficiency virus, simian immunodeficiency virus, equine infectious anemia virus, and caprine arthritis-encephalitis virus) that are capable of integrating into non-dividing cells (See, e.g., U.S. Pat. Nos. 5,994,136 and 6,013,516, both of which are incorporated herein by reference).

The term "pseudotyped lentivirus vector" refers to lentivirus vector containing a heterologous membrane protein (e.g., a viral envelope glycoprotein or the G proteins of viruses in the Rhabdoviridae family such as VSV, Piry, Chandipura and Mokola).

As used herein the term, the term "in vitro" refers to an artificial environment and to processes or reactions that occur within an artificial environment. In vitro environments can consist of, but are not limited to, test tubes and cell cultures. The term "in vivo" refers to the natural environment (e.g., an animal or a cell) and to processes or reactions that occur within a natural environment.

As used herein, the term "immunoglobulin" refers to proteins that bind a specific antigen. Immunoglobulins include, but are not limited to, polyclonal, monoclonal, chimeric, and humanized antibodies, Fab fragments, $F(ab')_2$ fragments, and includes immunoglobulins of the following classes: IgG, IgA, IgM, IgD, IbE, and secreted immunoglobulins (sIg). Immunoglobulins generally comprise two identical heavy chains and two light chains.

As used herein, the term "antigen binding protein" refers to proteins that bind to a specific antigen. "Antigen binding proteins" include, but are not limited to, immunoglobulins, including polyclonal, monoclonal, chimeric, and humanized antibodies; Fab fragments, $F(ab')_2$ fragments, and Fab expression libraries; and single chain antibodies.

As used herein, the term "antibody library" refers to a plurality of antibodies comprising a plurality of unique immunoglobulins or antibody chains (e.g., heavy or light chains). In preferred embodiments, antibody libraries comprise at least $10^2$, more preferably, at least $10^3$, even more preferably at least $10^4$, and still more preferably, at least $10^5$ unique antibodies or antibody chains.

As used herein, the term "pre-selected antigen" refers to a known antigen for which it is desired to identify an "antigen binding protein" or antibody that specifically binds the pre-selected antigen. Such antigen binding proteins or antibodies can be identified by "screening said antibody library." As used herein, the term "screening said antibody library" refers to the process of identifying antibodies within a antibody library that specifically bind to a pre-selected antigen. Screening may be carried out using any suitable method that is able to identify specific interactions between the pre-selected antigen and antibodies, including but not limited to, those screening methods disclosed herein. Preferably, screening is carried out in a high-throughput manner.

As used herein, the term "solution based detection assay" when used in the context of "screening said antibody library" refers to an assay for detecting the binding of antibodies to a pre-selected antigen that is conducted in solution (e.g., an aqueous solution). Examples of solution based detection assays include, but are not limited to, radioimmunoassay, ELISA (enzyme-linked immunosorbant assay), "sandwich" immunoassays, immunoradiometric assays, immunoprecipitation reactions, agglutination assays (e.g., hemagglutination assays, etc.), complement fixation assays, immunofluorescence assays, and protein A assays.

As used herein, the term "reporter gene" refers to a gene encoding a protein that may be assayed. Examples of reporter genes include, but are not limited to, luciferase (See, e.g., deWet et al., Mol. Cell. Biol. 7:725 [1987] and U.S. Pat Nos. 6,074,859; 5,976,796; 5,674,713; and 5,618,682; all of which are incorporated herein by reference), green fluorescent protein (e.g., GenBank Accession Number U43284; a number of GFP variants are commercially available from CLONTECH Laboratories, Palo Alto, Calif.), chloramphenicol acetyltransferase, β-galactosidase, alkaline phosphatase, and horse radish peroxidase.

As used herein, the term "purified" refers to molecules, either nucleic or amino acid sequences that are removed from their natural environment, isolated or separated. An "isolated nucleic acid sequence" is therefore a purified nucleic acid sequence. "Substantially purified" molecules are at least 60% free, preferably at least 75% free, and more preferably at least 90% free from other components with which they are naturally associated.

The term "test compound" refers to any chemical entity, pharmaceutical, drug, and the like contemplated to be useful in the treatment and/or prevention of a disease, illness, sickness, or disorder of bodily function, or otherwise alter the physiological or cellular status of a sample. Test compounds comprise both known and potential therapeutic compounds. A test compound can be determined to be therapeutic by screening using the screening methods of the present invention. A "known therapeutic compound" refers to a therapeutic compound that has been shown (e.g., through animal trials or prior experience with administration to humans) to be effective in such treatment or prevention.

DETAILED DESCRIPTION OF THE INVENTION

The present invention relates to the production of proteins in host cells, and more particularly to the production of antibody libraries. The present invention utilizes integrating retroviral vectors to create cell lines containing a library of unique antibody heavy and/or light chains. The antibody libraries of the present invention have the further advantage of strict control over MOI (e.g., only one antibody heavy chain and one antibody light chain per cell).

I. Vectors and Methods for Transfection

According to the present invention, antibody libraries are generated using integrating retroviral vectors comprising antibody heavy and/or light chain genes. The design, production, and use of these vectors in the present invention is described below.

A. Retroviral Vectors

Retroviruses (family Retroviridae) are divided into three groups: the spumaviruses (e.g., human foamy virus); the lentiviruses (e.g., human immunodeficiency virus and sheep visna virus) and the oncoviruses (e.g., MLV, Rous sarcoma virus).

Retroviruses are enveloped (i.e., surrounded by a host cell-derived lipid bilayer membrane) single-stranded RNA viruses that infect animal cells. When a retrovirus infects a cell, its RNA genome is converted into a double-stranded linear DNA form (i.e., it is reverse transcribed). The DNA form of the virus is then integrated into the host cell genome as a provirus. The provirus serves as a template for the production of additional viral genomes and viral mRNAs. Mature viral particles containing two copies of genomic RNA bud from the surface of the infected cell. The viral particle comprises the genomic RNA, reverse transcriptase and other pol gene products inside the viral capsid (which contains the viral gag gene products), which is surrounded by a lipid bilayer membrane derived from the host cell containing the viral envelope glycoproteins (also referred to as membrane-associated proteins).

The organization of the genomes of numerous retroviruses is well known to the art and this has allowed the adaptation of the retroviral genome to produce retroviral vectors. The production of a recombinant retroviral vector carrying antibody heavy or light chain genes of interest is typically achieved in two stages.

First, the antibody heavy or light chain genes of interest is inserted into a retroviral vector which contains the sequences necessary for the efficient expression of the antibody heavy or light chain genes of interest (including promoter and/or enhancer elements which may be provided by the viral long terminal repeats (LTRs) or by an internal promoter/enhancer and relevant splicing signals), sequences required for the efficient packaging of the viral RNA into infectious virions (e.g., the packaging signal (Psi), the tRNA primer binding site (−PBS), the 3' regulatory sequences required for reverse transcription (+PBS)) and the viral LTRs. The LTRs contain sequences required for the association of viral genomic RNA, reverse transcriptase and integrase functions, and sequences involved in directing the expression of the genomic RNA to be packaged in viral particles. For safety reasons, many recombinant retroviral vectors lack functional copies of the genes that are essential for viral replication (these essential genes are either deleted or disabled); therefore, the resulting virus is said to be replication defective.

Second, following the construction of the recombinant vector, the vector DNA is introduced into a packaging cell line. Packaging cell lines provide proteins required in trans for the packaging of the viral genomic RNA into viral particles having the desired host range (i.e., the viral-encoded gag, pol and env proteins). The host range is controlled, in part, by the type of envelope gene product expressed on the surface of the viral particle. Packaging cell lines may express ecotrophic, amphotropic or xenotropic envelope gene products. Alternatively, the packaging cell line may lack sequences encoding a viral envelope (env) protein. In this case the packaging cell line will package the viral genome into particles that lack a membrane-associated protein (e.g., an env protein). In order to produce viral particles containing a membrane associated protein that will permit entry of the virus into a cell, the packaging cell line containing the retroviral sequences is transfected with sequences encoding a membrane-associated protein (e.g., the G protein of vesicular stomatitis virus (VSV)). The transfected packaging cell will then produce viral particles that contain the membrane-associated protein expressed by the transfected packaging cell line; these viral particles, which contain viral genomic RNA derived from one virus encapsidated by the envelope proteins of another virus, are said to be pseudotyped virus particles.

The retroviral vectors utilized in the methods and compositions of the present invention can be further modified to include additional regulatory sequences. As described above, the retroviral vectors of the present invention include the following elements in operable association: a) a 5' LTR; b) a packaging signal; c) a 3' LTR and d) a nucleic acid encoding a protein of interest located between the 5' and 3' LTRs. In some embodiments of the present invention, the nucleic acid of interest may be arranged in opposite orientation to the 5' LTR when transcription from an internal promoter is desired. Suitable internal promoters include, but are not limited to, the alpha-lactalbumin promoter, the CMV promoter (human or ape), and the thymidine kinase promoter.

In other embodiments of the present invention, where secretion of the antibody heavy or light chains of interest is desired, the vectors are modified by including a signal peptide sequence in operable association with the protein of interest. The sequences of several suitable signal peptides are known to those in the art, including, but not limited to, those derived from tissue plasminogen activator, human growth hormone, lactoferrin, alpha-casein, and alpha-lactalbumin. In other embodiments, the native signal peptide sequence of the heavy and/or light chain gene is utilized.

In other embodiments of the present invention, the vectors are modified by incorporating an RNA export element (See, e.g., U.S. Pat. Nos. 5,914,267; 6,136,597; and 5,686,120; and WO99/14310, all of which are incorporated herein by reference) either 3' or 5' to the nucleic acid sequence encoding the protein of interest. It is contemplated that the use of RNA export elements allows high levels of expression of the antibody heavy or light chains of interest without incorporating splice signals or introns in the nucleic acid sequence encoding the antibody heavy or light chains of interest.

In still other embodiments, the vector further comprises at least one internal ribosome entry site (IRES) sequence. The sequences of several suitable IRES's are available, including, but not limited to, those derived from foot and mouth disease virus (FDV), encephalomyocarditis virus, and poliovirus. The IRES sequence can be interposed between two transcriptional units (e.g., nucleic acids encoding different proteins of interest or subunits of a multisubunit protein such as an antibody) to form a polycistronic sequence so that the two transcriptional units are transcribed from the same promoter.

The retroviral vectors of the present invention may also further comprise a selectable marker allowing selection of transformed cells. A number of selectable markers find use in the present invention, including, but not limited to the bacterial aminoglycoside 3' phosphotransferase gene (also referred to as the neo gene) that confers resistance to the drug G418 in mammalian cells, the bacterial hygromycin G phosphotransferase (hyg) gene that confers resistance to the antibiotic hygromycin and the bacterial xanthine-guanine phosphoribosyl transferase gene (also referred to as the gpt gene) that confers the ability to grow in the presence of mycophenolic acid.

In still other embodiments of the present invention, the retroviral vectors may comprise recombination elements recognized by a recombination system (e.g., the cre/loxP or flp recombinase systems, see, e.g., Hoess et al., Nucleic Acids Res. 14:2287-2300 [1986], O'Gorman et al., Science 251: 1351-55 [1991], van Deursen et al., Proc. Natl. Acad. Sci. USA 92:7376-80 [1995], and U.S. Pat. No. 6,025,192, herein incorporated by reference). After integration of the vectors into the genome of the host cell, the host cell can be transiently transfected (e.g., by electroporation, lipofection, or microinjection) with either a recombinase enzyme (e.g., Cre recombinase) or a nucleic acid sequence encoding the recombinase enzyme and one or more nucleic acid sequences encoding antibody heavy or light chains of interest flanked by sequences recognized by the recombination enzyme so that the nucleic acid sequence is inserted into the integrated vector.

Viral vectors, including recombinant retroviral vectors, provide a more efficient means of transferring genes into cells as compared to other techniques such as calcium phosphate-DNA co-precipitation or DEAE-dextran-mediated transfection, electroporation or microinjection of nucleic acids. It is believed that the efficiency of viral transfer is due in part to the fact that the transfer of nucleic acid is a receptor-mediated process (i.e., the virus binds to a specific receptor protein on the surface of the cell to be infected). In addition, the virally transferred nucleic acid once inside a cell integrates in controlled manner in contrast to the integration of nucleic acids which are not virally transferred; nucleic acids transferred by other means such as calcium phosphate-DNA co-precipitation are subject to rearrangement and degradation.

The most commonly used recombinant retroviral vectors are derived from the amphotropic Moloney murine leukemia virus (MoMLV) (See e.g., Miller and Baltimore Mol. Cell. Biol. 6:2895 [1986]). The MoMLV system has several advantages: 1) this specific retrovirus can infect many different cell types, 2) established packaging cell lines are available for the production of recombinant MoMLV viral particles and 3) the transferred genes are permanently integrated into the target cell chromosome. The established MoMLV vector systems comprise a DNA vector containing a small portion of the retroviral sequence (e.g., the viral long terminal repeat or "LTR" and the packaging or "psi" signal) and a packaging cell line. The antibody heavy or light chain genes to be transferred are inserted into the DNA vector. The viral sequences present on the DNA vector provide the signals necessary for the insertion or packaging of the vector RNA into the viral particle and for the expression of the inserted gene. The packaging cell line provides the proteins required for particle assembly (Markowitz et al., J. Virol. 62:1120 [1988]).

Despite these advantages, existing retroviral vectors based upon MoMLV are limited by several intrinsic problems: 1) they do not infect non-dividing cells (Miller et al., Mol. Cell. Biol. 10:4239 [1990]), except, perhaps, oocytes; 2) they produce low titers of the recombinant virus (Miller and Rosman, BioTechniques 7: 980 [1980] and Miller, Nature 357: 455 [1990]); and 3) they infect certain cell types (e.g., human lymphocytes) with low efficiency (Adams et al., Proc. Natl. Acad. Sci. USA 89:8981 [1992]). The low titers associated with MoMLV-based vectors have been attributed, at least in part, to the instability of the virus-encoded envelope protein. Concentration of retrovirus stocks by physical means (e.g., ultracentrifugation and ultrafiltration) leads to a severe loss of infectious virus.

The low titer and inefficient infection of certain cell types by MoMLV-based vectors has been overcome by the use of pseudotyped retroviral vectors that contain the G protein of VSV as the membrane associated protein. Unlike retroviral envelope proteins, which bind to a specific cell surface protein receptor to gain entry into a cell, the VSV G protein interacts with a phospholipid component of the plasma membrane (Mastromarino et al., J. Gen. Virol. 68:2359 [1977]). Because entry of VSV into a cell is not dependent upon the presence of specific protein receptors, VSV has an extremely broad host range. Pseudotyped retroviral vectors bearing the VSV G protein have an altered host range characteristic of VSV (i.e., they can infect almost all species of vertebrate, invertebrate and insect cells). Importantly, VSV G-pseudotyped retroviral vectors can be concentrated 2000-fold or more by ultracentrifugation without significant loss of infectivity (Burns et al. Proc. Natl. Acad. Sci. USA 90:8033 [1993]).

The present invention is not limited to the use of the VSV G protein when a viral G protein is employed as the heterologous membrane-associated protein within a viral particle (See, e.g., U.S. Pat. No. 5,512,421, which is incorporated herein by reference). The G proteins of viruses in the *Vesiculovirus* genera other than VSV, such as the Piry and Chandipura viruses, that are highly homologous to the VSV G protein and, like the VSV G protein, contain covalently linked palmitic acid (Brun et al. Intervirol. 38:274 [1995] and Masters et al., Virol. 171:285 (1990]). Thus, the G protein of the Piry and Chandipura viruses can be used in place of the VSV G protein for the pseudotyping of viral particles. In addition, the VSV G proteins of viruses within the Lyssa virus genera such as Rabies and Mokola viruses show a high degree of conservation (amino acid sequence as well as functional conservation) with the VSV G proteins. For example, the Mokola virus G protein has been shown to function in a manner similar to the VSV G protein (i.e., to mediate membrane fusion) and therefore may be used in place of the VSV G protein for the pseudotyping of viral particles (Mebatsion et al., J. Virol. 69:1444 [1995]). Viral particles may be pseudotyped using either the Piry, Chandipura or Mokola G protein as described in Example 2, with the exception that a plasmid containing sequences encoding either the Piry, Chandipura or Mokola G protein under the transcriptional control of a suitable promoter element (e.g., the CMV intermediate-early promoter; numerous expression vectors containing the CMV IE promoter are available, such as the pcDNA3.1 vectors (Invitrogen)) is used in place of pHCMV-G. Sequences encoding other G proteins derived from other members of the Rhabdoviridae family may be used; sequences encoding numerous rhabdoviral G proteins are available from the GenBank database.

The majority of retroviruses can transfer or integrate a double-stranded linear form of the virus (the provirus) into the genome of the recipient cell only if the recipient cell is cycling (i.e., dividing) at the time of infection. Retroviruses that have been shown to infect dividing cells exclusively, or more efficiently, include MLV, spleen necrosis virus, Rous sarcoma virus and human immunodeficiency virus (HIV; while HIV infects dividing cells more efficiently, HIV can infect non-dividing cells).

It has been shown that the integration of MLV virus DNA depends upon the host cell's progression through mitosis and it has been postulated that the dependence upon mitosis reflects a requirement for the breakdown of the nuclear envelope in order for the viral integration complex to gain entry into the nucleus (Roe et al., EMBO J. 12:2099 [1993]). However, as integration does not occur in cells arrested in metaphase, the breakdown of the nuclear envelope alone may not be sufficient to permit viral integration; there may be additional requirements such as the state of condensation of the genomic DNA (Roe et al., supra).

The present invention also contemplates the use of lentiviral vectors to generate high copy number cell lines. The lentiviruses (e.g., equine infectious anemia virus, caprine arthritis-encephalitis virus, human immunodeficiency virus) are a subfamily of retroviruses that are able to integrate into non-dividing cells. The lentiviral genome and the proviral DNA have the three genes found in all retroviruses: gag, pol, and env, which are flanked by two LTR sequences. The gag gene encodes the internal structural proteins (e.g., matrix, capsid, and nucleocapsid proteins); the pol gene encodes the reverse transcriptase, protease, and integrase proteins; and the pol gene encodes the viral envelope glycoproteins. The 5' and 3' LTRs control transcription and polyadenylation of the viral RNAs. Additional genes in the lentiviral genome include the vif, vpr, tat, rev, vpu, nef, and vpx genes.

A variety of lentiviral vectors and packaging cell lines are known in the art and find use in the present invention (See, e.g., U.S. Pat. Nos. 5,994,136 and 6,013,516, both of which are herein incorporated by reference). Furthermore, the VSV G protein has also been used to pseudotype retroviral vectors based upon the human immunodeficiency virus (HIV) (Naldini et al., Science 272:263 [1996]). Thus, the VSV G protein may be used to generate a variety of pseudotyped retroviral vectors and is not limited to vectors based on MoMLV. The lentiviral vectors may also be modified as described above to contain various regulatory sequences (e.g., signal peptide sequences, RNA export elements, and IRES's). After the lentiviral vectors are produced, they may be used to transfect host cells as described below for retroviral vectors.

II. Use of Host Cells To Produce Antibodies

In some preferred embodiments, the methods of the present invention are used to generate antibody libraries from immunoglobulin heavy and light chain genes. In some embodiments, the host cells express more than one exogenous protein. For example, the host cells may be transfected with vectors encoding different proteins of interest (e.g., cotransfection with one vector encoding a first protein of interest (e.g., immunoglobulin light chain) and a second vector encoding a second protein of interest (e.g., immunoglobulin heavy chain) or serial transfection or infection) so that the host cell contains at least one integrated copy of a first vector encoding a first antibody heavy or light chain of interest and at least one integrated copy of second integrating vector encoding a second antibody heavy or light chain of interest.

A. Antibody Genes

The present invention is not limited to the use of particular antibody genes. In some embodiments, antibody heavy and/or light chain genes are obtained commercially. Commercially available libraries included, but are not limited to, those available from Cambridge Antibody Technology (Cambridgeshire, United Kingdom), HUCAL libraries (See e.g., U.S. Pat. No. 5,514,548, herein incorporated by reference) available from Morphosys (Munich, Germany), Bioinvent (Lund, Sweden), and INTRACEL (Rockville, Md.). In other embodiments, antibody heavy and light chain genes are obtained by PCR (e.g., including but not limited to, the method disclosed in U.S. Pat. No. 6,291,650, herein incorporated by reference).

B. Generation of Antibody Libraries

In some embodiments, greater than one (e.g., two or more, preferably five or more, and more preferably, 10 or more) heavy and light chains are used to generate antibody libraries using retroviral vectors. In some embodiments, antibody genes are first cloned into GATEWAY (Invitrogen, Carlsbad, Calif.) entry vectors. In preferred embodiments, heavy chain antibody sequences (one gene per vector) are cloned into vectors comprising a first selectable marker and light chain antibody sequences are cloned into vectors comprising a second selectable marker.

In some embodiments, antibody genes are next transferred into retroviral vectors containing GATEWAY recombination sequences inserted in between retroviral LTR sequences (See e.g., the above description of retroviral vectors). In some embodiments, each retroviral vector contains either a heavy chain or a light chain antibody gene, as well as one of two selectable markers. In other embodiments, the retroviral vectors contain one heavy chain gene and one light chain gene separated by an IRES sequence.

In some embodiments, following transfer of antibody genes into retroviral vectors, the vectors are packaged in packaging cell line (e.g., 293 GP cells) to generate retroviral particles. Retroviral particles may be generated using any suitable method, including but not limited to, those described below. In some embodiments, each retroviral particle contains one antibody gene (e.g., either a heavy or a light chain gene). In other embodiments, each vector contains one heavy chain gene and one light chain gene separated by an IRES.

In some embodiments, retroviral particles are next used to transduce host cells (e.g., mammalian cells). Host cells may be transduced and cultured using any suitable method, including but not limited to, those described below. In preferred embodiments, prior to transduction, the viral titer is determined and the correct amount of virus necessary to obtain the desired MOI of infection is used. For example, if retroviral particles containing a single antibody heavy or light chain gene are utilized, a MOI of two is desired. In such embodiments, host cells are first transduced with virus containing either a heavy or light chain gene and grown under condition to select the associated selectable marker. Next, the host cells are transduced again with the other antibody gene and the second selectable marker is selected for, thus resulting in host cells comprising one heavy chain gene and one light chain gene. In other embodiments, both heavy chain containing and light chain containing retroviral particles are simultaneously used to transduce host cells, followed by selection for both markers.

In yet other embodiments, retroviral particles containing both heavy and light chain antibody genes are used to transduce host cells at a MOI of 1, followed by selection for both markers.

C. Screening Antibody Libraries

The present invention contemplates the use of cell lines for screening compounds for activity, and in particular to high throughput screening of compounds from combinatorial libraries (e.g., antibody libraries containing greater than $10^2$ unique antibodies or antibody heavy or light chains). The antibody libraries of the present invention can be screened using a variety of screening methods. In preferred embodiments, antibody libraries are screened for their ability to bind to a pre-selected antigen.

In some embodiments, antibodies are expressed on the cell surface of host cells as membrane bound antibodies (See e.g., U.S. Pat. Nos. 6,214,613 and 5,298,420, each of which is herein incorporated by reference). Membrane bound antibodies may be screened for antigen binding by any suitable method, including but not limited to, flow cytometry.

Flow cytometry objectively quantifies and separates single cells on the basis of one or more parameters (e.g., binding to a pre-selected antigen). Flow cytometry involves channeling individual cells in a narrow fluid stream past a laser beam, which is usually oriented at a right angle to the flow. Optical sensors detect signals generated as the cells pass through the laser beam. The cells scatter the laser light in proportion to their size and "complexity" (e.g. presence of granules in their cytoplasm). Thus, cells can be identified based on their light scatter characteristics, and a population chosen (gated) for further analysis.

In some embodiments, pre-selected antigens coupled to fluorochromes (different fluorochromes emit different wavelengths of light upon excitation by a laser) are used to label or "stain" the cells so that each cell can be identified and quantitated based upon its fluorescence signal. In other embodiments, secondary antibodies that specifically bind to the pre-selected antigen are coupled to fluorochromes and used for detection. A computer collects the fluorescence signature of each cell and displays the pattern of fluorescence for the user to analyze. In other applications, where one might want to separate cells which have a certain staining pattern from all other cells (e.g., due to binding to a labeled pre-selected antigen), the flow cytometry machine can direct those desired cells into a tube provided by the user. This is called fluorescence activated cell sorting (FACS).

In other embodiments, antibodies generated by the methods of the present invention are secreted into medium (e.g., using the methods described in Example 3). For example, in some embodiments, antibodies are secreted in 96 well plates. Each well of the plate can then be diluted, for example to 100 cells per well. The plates can be screened for binding to a pre-selected antigen using any suitable method. Any immunoassay that tests for binding specificity familiar to the skilled artisan may be used in this step and subsequent steps involving measures of binding with cells, including but not limited to, radioimmunoassay, ELISA (enzyme-linked immunosorbant assay), "sandwich" immunoassays, immunoradiometric assays, immunoprecipitation reactions, agglutination assays (e.g., hemagglutination assays, etc.), complement fixation assays, immunofluorescence assays, and protein A assays. Wells giving a positive signal can then be further diluted to contain 1-10 antibody producing cells. These plates can then be further screened in order to identify the antibody producing cell(s) with the desired binding properties. The desired cells can be used to generate stable cell lines (e.g., using the methods described in Example 3).

The present invention is not limited to the screening methods disclosed herein. One skilled in the art recognizes that any suitable method may be utilized that results in the identification of antibodies with the desired properties (e.g., antigen binding).

III. Generation of Host Cells Comprising Integrated Retroviral Vectors

The present invention further provides methods of generating host cells comprising integrated retroviral vectors comprising antibody heavy or light chain genes.

A. Transfection of Integrating Vectors

Once integrating vectors (e.g., retroviral vectors) encoding an antibody heavy or light chains of interest have been produced, they may be used to transfect or transduce host cells (examples of which are described below). Preferably, host cells are transfected or transduced with integrating vectors at a multiplicity of infection sufficient to result in the integration of the desired number of vectors (e.g., one or two). When non-pseudotyped retroviral vectors are utilized for infection, the host cells are incubated with the culture medium from the retroviral producing cells containing the desired titer (i.e., colony forming units, CFUs) of infectious vectors. When pseudotyped retroviral vectors are utilized, the vectors are concentrated to the appropriate titer by ultracentrifugation and then added to the host cell culture. Alternatively, the concentrated vectors can be diluted in a culture medium appropriate for the cell type.

In each case, the host cells are exposed to medium containing the infectious retroviral vectors for a sufficient period of time to allow infection and subsequent integration of the vectors. In general, the amount of medium used to overlay the cells should be kept to as small a volume as possible so as to encourage the maximum amount of integration events per cell. As a general guideline, the number of colony forming units (cfu) per milliliter should be about $10^5$ to $10^7$ cfu/ml, depending upon the number of integration events desired. The host cells (See below description of host cells) are then cultured (e.g., according to the methods described below).

B. Host Cells

The present invention contemplates the transfection of a variety of host cells with retroviral vectors in order to generate the antibody libraries of the present invention. A number of mammalian host cell lines are known in the art. In general, these host cells are capable of growth and survival when placed in either monolayer culture or in suspension culture in a medium containing the appropriate nutrients and growth factors, as is described in more detail below. Typically, the cells are capable of expressing and secreting large quantities of a particular antibody heavy or light chains of interest into the culture medium. Examples of suitable mammalian host cells include, but are not limited to Chinese hamster ovary cells (CHO-K1, ATCC CCl-61); bovine mammary epithelial cells (ATCC CRL 10274; bovine mammary epithelial cells); monkey kidney CV1 line transformed by SV40 (COS-7, ATCC CRL 1651); human embryonic kidney line (293 or 293 cells subcloned for growth in suspension culture; see, e.g., Graham et al., J. Gen Virol., 36:59 [1977]); baby hamster kidney cells (BHK, ATCC CCL 10); mouse sertoli cells (TM4, Mather, Biol. Reprod. 23:243-251 [1980]); monkey kidney cells (CV1 ATCC CCL 70); African green monkey kidney cells (VERO-76, ATCC CRL-1587); human cervical carcinoma cells (HELA, ATCC CCL 2); canine kidney cells (MDCK, ATCC CCL 34); buffalo rat liver cells (BRL 3A, ATCC CRL 1442); human lung cells (W138, ATCC CCL 75); human liver cells (Hep G2, HB 8065); mouse mammary tumor (MMT 060562, ATCC CCL51); TRI cells (Mather et al., Annals N.Y. Acad. Sci., 383:44-68 [1982]); MRC 5 cells; FS4 cells; rat fibroblasts (208F cells); MDBK cells (bovine kidney cells); and a human hepatoma line (Hep G2).

The present invention also contemplates the use of amphibian and insect host cell lines. Examples of suitable insect host cell lines include, but are not limited to, mosquito cell lines (e.g., ATCC CRL-1660). Examples of suitable amphibian host cell lines include, but are not limited to, toad cell lines (e.g., ATCC CCL-102).

C. Host Cell Culture

The transfected host cells are cultured according to methods known in the art. Suitable culture conditions for mammalian cells are well known in the art (See e.g., J. Immunol. Methods (1983)56:221-234 [1983], *Animal Cell Culture: A Practical Approach* 2nd Ed., Rickwood, D. and Hames, B. D., eds. Oxford University Press, New York [1992]).

The host cell cultures of the present invention are prepared in a media suitable for the particular cell being cultured. Commercially available media such as Ham's F10 (Sigma, St. Louis, Mo.), Minimal Essential Medium (MEM, Sigma), RPMI-1640 (Sigma), and Dulbecco's Modified Eagle's Medium (DMEM, Sigma) are exemplary nutrient solutions. Suitable media are also described in U.S. Pat. Nos. 4,767,704; 4,657,866; 4,927,762; 5,122,469; 4,560,655; and WO 90/03430 and WO 87/00195; the disclosures of which are herein incorporated by reference. Any of these media may be supplemented as necessary with serum, hormones and/or other growth factors (such as insulin, transferrin, or epidermal growth factor), salts (such as sodium chloride, calcium, magnesium, and phosphate), buffers (such as HEPES), nucleosides (such as adenosine and thymidine), antibiotics (such as gentamycin (gentamicin), trace elements (defined as inorganic compounds usually present at final concentrations in the micromolar range) lipids (such as linoleic or other fatty acids) and their suitable carriers, and glucose or an equivalent energy source. Any other necessary supplements may also be included at appropriate concentrations that would be known to those skilled in the art. For mammalian cell culture, the osmolality of the culture medium is generally about 290-330 mOsm.

The present invention also contemplates the use of a variety of culture systems (e.g., petri dishes, 96 well plates, roller bottles, and bioreactors) for the transfected host cells. For example, the transfected host cells can be cultured in a perfusion system. Perfusion culture refers to providing a continuous flow of culture medium through a culture maintained at high cell density. The cells are suspended and do not require a solid support to grow on. Generally, fresh nutrients must be supplied continuously with concomitant removal of toxic metabolites and, ideally, selective removal of dead cells. Filtering, entrapment and micro-capsulation methods are all suitable for refreshing the culture environment at sufficient rates.

As another example, in some embodiments a fed batch culture procedure can be employed. In the preferred fed batch culture the mammalian host, cells and culture medium are supplied to a culturing vessel initially and additional culture nutrients are fed, continuously or in discrete increments, to the culture during culturing, with or without periodic cell and/or product harvest before termination of culture. The fed batch culture can include, for example, a semi-continuous fed batch culture, wherein periodically whole culture (including cells and medium) is removed and replaced by fresh medium. Fed batch culture is distinguished from simple batch culture in which all components for cell culturing (including the cells and all culture nutrients) are supplied to the culturing vessel at the start of the culturing process. Fed batch culture can be further distinguished from perfusion culturing insofar as the supernate is not removed from the culturing vessel during the process (in perfusion culturing, the cells are restrained in the culture by, e.g., filtration, encapsulation, anchoring to microcarriers etc. and the culture medium is continuously or intermittently introduced and removed from the culturing vessel). In some particularly preferred embodiments, the batch cultures are performed in roller bottles.

Further, the cells of the culture may be propagated according to any scheme or routine that may be suitable for the particular host cell and the particular production plan contemplated. Therefore, the present invention contemplates a single step or multiple step culture procedure. In a single step culture the host cells are inoculated into a culture environment and the processes of the instant invention are employed during a single production phase of the cell culture. Alternatively, a multi-stage culture is envisioned. In the multi-stage culture cells may be cultivated in a number of steps or phases. For instance, cells may be grown in a first step or growth phase culture wherein cells, possibly removed from storage, are inoculated into a medium suitable for promoting growth and high viability. The cells may be maintained in the growth phase for a suitable period of time by the addition of fresh medium to the host cell culture.

Fed batch or continuous cell culture conditions are devised to enhance growth of the mammalian cells in the growth phase of the cell culture. In the growth phase cells are grown under conditions and for a period of time that is maximized for growth. Culture conditions, such as temperature, pH, dissolved oxygen ($dO_2$) and the like, are those used with the particular host and will be apparent to the ordinarily skilled artisan. Generally, the pH is adjusted to a level between about 6.5 and 7.5 using either an acid (e.g., $CO_2$) or a base (e.g., $Na_2CO_3$ or NaOH). A suitable temperature range for culturing mammalian cells such as CHO cells is between about 30° to 38° C. and a suitable $dO_2$ is between 5-90% of air saturation.

In some embodiments, following the antibody heavy and/or light chain production phase, the antibody heavy and/or light chains of interest are recovered from the culture medium using techniques that are well established in the art. In some embodiments, the heavy and/or light chains preferably recovered from the culture medium as secreted polypeptides (e.g., the secretion of the heavy and/or light chain of interest is directed by a signal peptide sequence), although it also may be recovered from host cell lysates. As a first step, the culture medium or lysate is centrifuged to remove particulate cell debris. The polypeptide thereafter is purified from contaminant soluble proteins and polypeptides, with the following procedures being exemplary of suitable purification procedures: by fractionation on immunoaffinity or ion-exchange columns; ethanol precipitation; reverse phase HPLC; chromatography on silica or on a cation-exchange resin such as DEAE; chromatofocusing; SDS-PAGE; ammonium sulfate precipitation; gel filtration using, for example, Sephadex G-75; and protein A Sepharose columns to remove contaminants such as IgG. A protease inhibitor such as phenyl methyl sulfonyl fluoride (PMSF) also may be useful to inhibit proteolytic degradation during purification. Additionally, the protein of interest can be fused in frame to a marker sequence, which allows for purification of the protein of interest. Non-limiting examples of marker sequences include a hexahistidine tag that may be supplied by a vector, preferably a pQE-9 vector, and a hemagglutinin (HA) tag. The HA tag corresponds to an epitope derived from the influenza hemagglutinin protein (See e.g., Wilson et al., Cell, 37:767 [1984]). One skilled in the art will appreciate that purification methods suitable for the polypeptide of interest may require modification to account for changes in the character of the polypeptide upon expression in recombinant cell culture.

EXPERIMENTAL

The following examples serve to illustrate certain preferred embodiments and aspects of the present invention and are not to be construed as limiting the scope thereof.

In the experimental disclosure which follows, the following abbreviations apply: M (molar); mM (millimolar); μM (micromolar); nM (nanomolar); mol (moles); mmol (millimoles); μmol (micromoles); nmol (nanomoles); gm (grams); mg (milligrams); μg (micrograms); pg (picograms); L (liters); ml (milliliters); μl (microliters); cm (centimeters); mm (millimeters); μm (micrometers); nm (nanometers); ° C. (degrees Centigrade); AMP (adenosine 5'-monophosphate); BSA (bovine serum albumin); cDNA (copy or complimentary DNA); CS (calf serum); DNA (deoxyribonucleic acid); ssDNA (single stranded DNA); dsDNA (double stranded DNA); dNTP (deoxyribonucleotide triphosphate); LH (luteinizing hormone); NIH (National Institutes of Health, Besthesda, Md.); RNA (ribonucleic acid); PBS (phosphate buffered saline); g (gravity); OD (optical density); HEPES (N-[2-Hydroxyethyl]piperazine-N-[2-ethanesulfonic acid]); HBS (HEPES buffered saline); PBS (phosphate buffered saline); SDS (sodium dodecylsulfate); Tris-HCl (tris[Hydroxymethyl]aminomethane-hydrochloride); Klenow (DNA polymerase I large (Klenow) fragment); rpm (revolutions per minute); EGTA (ethylene glycol-bis(β-aminoethyl ether) N, N, N', N'-tetraacetic acid); EDTA (ethylenediaminetetracetic acid); bla (β-lactamase or ampicillin-resistance gene); ORI (plasmid origin of replication); lacI (lac repressor); X-gal (5-bromo-4-chloro-3-indolyl-β-D-galactoside); ATCC (American Type Culture Collection, Rockville, Md.); GIBCO/BRL (GIBCO/BRL, Grand Island, N.Y.); Perkin-Elmer (Perkin-Elmer, Norwalk, Conn.); and Sigma (Sigma Chemical Company, St. Louis, Mo.).

EXAMPLE 1

Construction of Retroviral Vectors Containing Antibody Genes

This Example describes the cloning of the heavy chains of MN14 and LL2 antibodies into a Gateway vector (Invitrogen, CA) incorporating one selectable marker, and the light chains of MN14 and LL2 antibodies into a second Gateway vector with a second selectable marker. Co-transfection into retroviral vectors with both vector "libraries" and selection for both markers allows for the formation of antibodies with all possible heavy chain/light chain combinations.

A. Vector Construction

The GATEWAY (Invitrogen, Carslbad, Calif.) system is a cloning system based on site-specific recombination. Sequences of interest are cloned into a first GATEWAY vector (referred to as an entry clone). The sequences of interest can then be transferred to destination vectors (e.g., those containing retroviral LTRs) containing compatible recombination sequences through site-specific recombination.

Retroviral vectors were constructed containing the light and heavy chains form MN14 and LL2 antibodies. First, both the light chain genes and the heavy chain genes were cloned into the GATEWAY entry vector pENTR11 with the NcoI sites upstream of the 5' EcoRI site removed.

Figure 2:
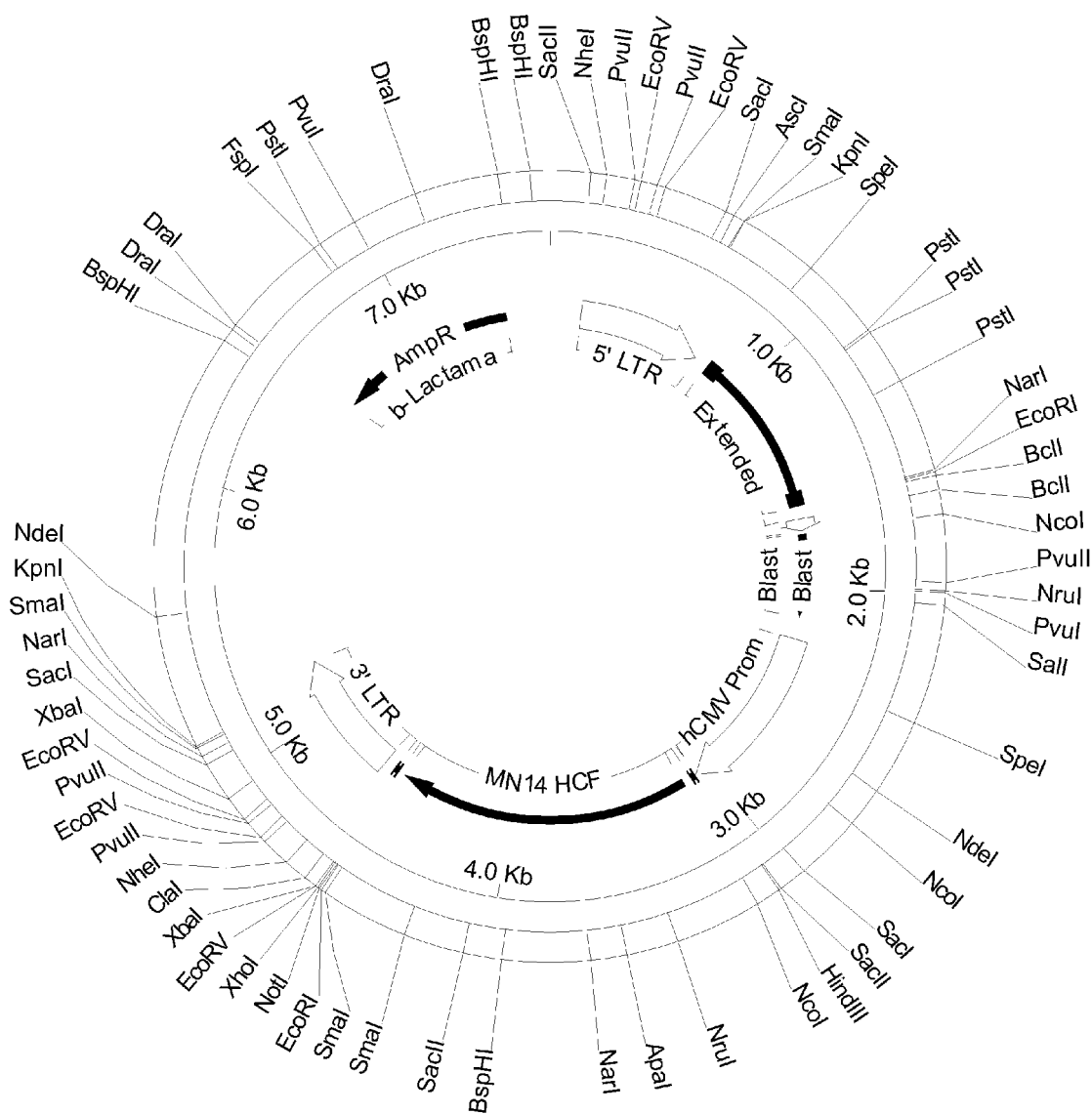
FIG. 2 shows a plasmid map of pLBC-M4HCF.

For heavy chain genes, the destination vector used was pLBCG-S, which contains the retroviral LTR sequences flanking GATEWAY recombination sequences and a Blastocidin selectable marker. The splicing site removed versions of both the MN14 and LL2 heavy chain genes were recombined from pENTR11-M4HCF or pENTR11-L2HCF into the pLBCG-S plasmid to give pLBC-L2HCF (SEQ ID NO:1) and pLBC-M4HCF (SEQ ID NO:2) (See FIGS. 1 and 2).

Figure 3:
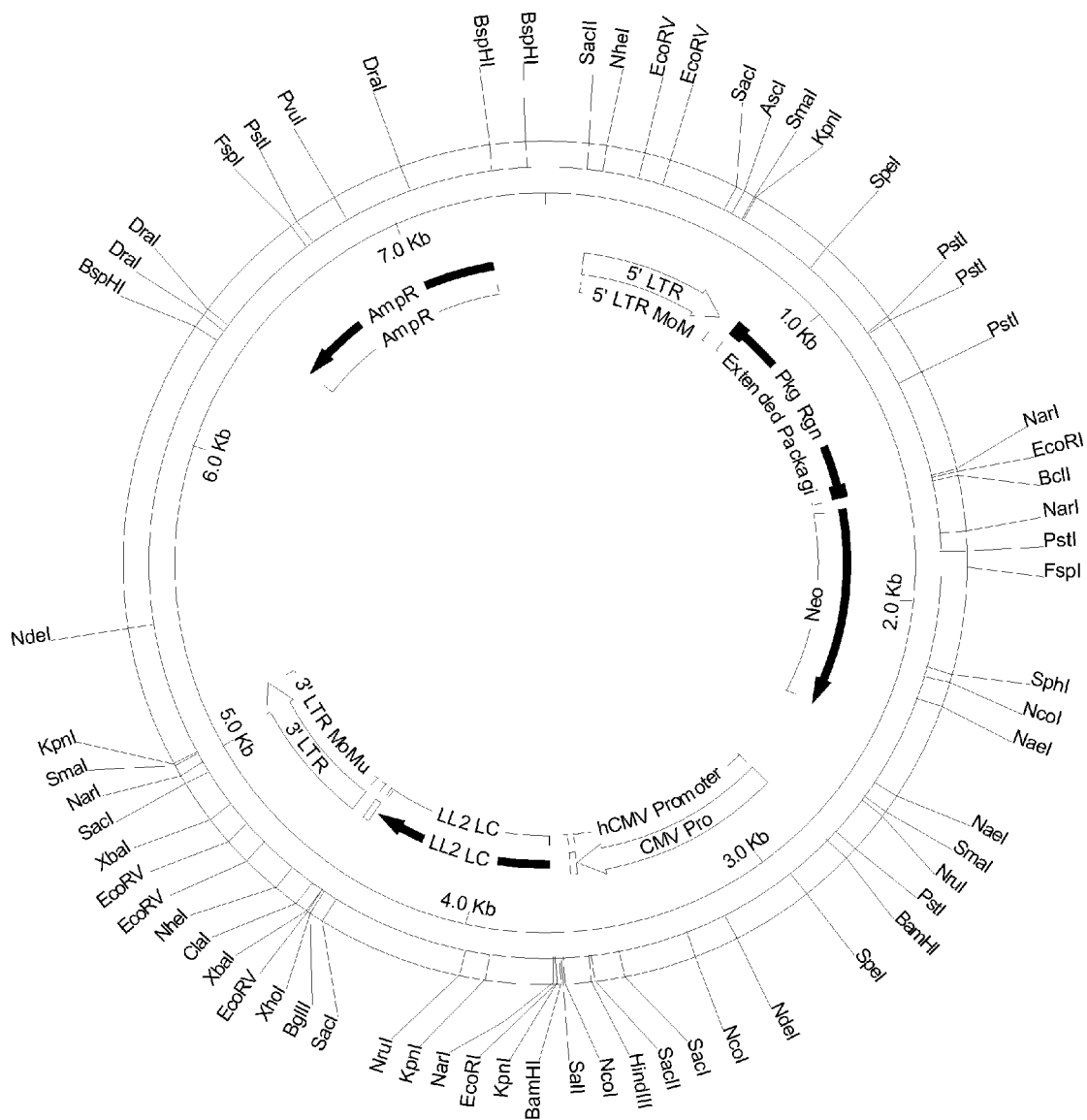
FIG. 3 shows a plasmid map of pLNC-L2LC.
Figure 4:
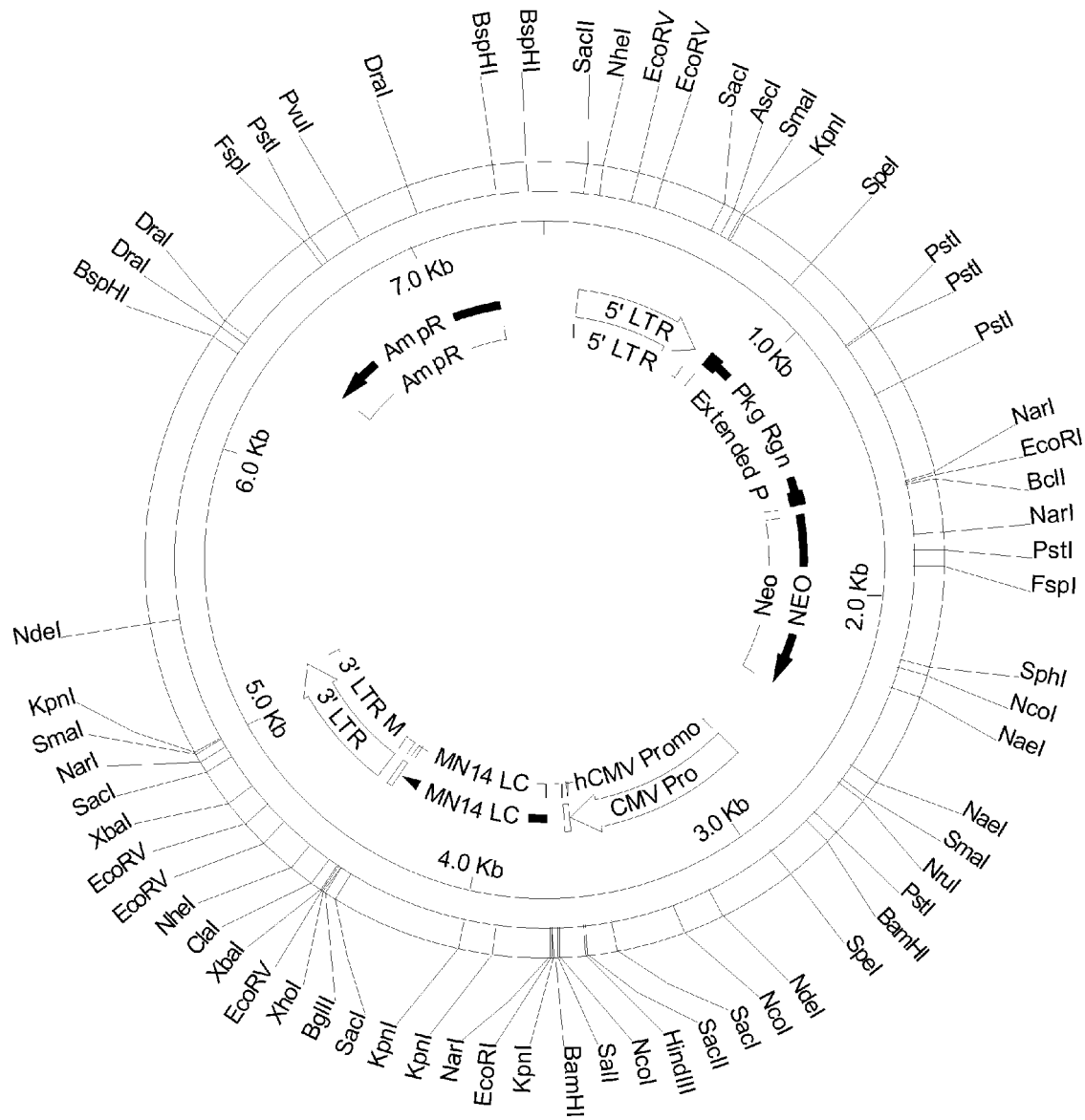
FIG. 4 shows a plasmid map of pLNC-M4LC.

The light chains were recombined into the Gateway version of pLNC to give plasmids pLNC-L2LC (SEQ ID NO:3) and pLNC-M4LC (SEQ ID NO:4) (See FIGS. 3 and 4).

A test of recombining different ratios of the light chain constructs into the expression vector (pLNC-G) was performed. Clones from the "library" were screened to determine the number of clones that can be obtained from a reaction, the frequency of clones without inserts and representation of the clones. Three recombination reactions were performed using different ratios of the light chain constructs (1:1 LL2 LC:MN14 LC, 1:4 and 4:1) in the expression vector (pLNC-G). All three reactions gave ~5000 clones from transforming 2 µl of a 22 µl recombination reaction. 150 ng Entry DNA to 300 ng of Destination vector was used. 15 clones from each of the reactions were screened by minipreps. All clones had either the MN14 or LL2 light chain insert; there were no clones without inserts. Of 15 clones screened from each of the 3 reactions, the products showed ~1:1 (10 LL2:8 MN14), ~4:1 (11 LL2:4 MN14) and ~1:4 (4 LL2:11 MN14)

B. Library Construction

The construction of the library was performed in two steps. 1) Creation of a light chain (LL2 and MN14) library in the 293 cell line and 2) The 'superinfection' of this cell line with the heavy chains from LL2 and MN14. The light chain construction led to a vector initial titer of $1.6 \times 10^5$. The heavy chain initial titer was $4.3 \times 10^4$. The double infected cells were maintained in two selection plates, one containing blasticidin (HC marker) the other containing blasticidin and neomycin. Both cultures grew well.

Single colonies were made and from an initial 50 clones, 38 viable clones were obtained. The supernatants of these clones were analyzed for human kappa light chain, human Fc (IgG) and CEA antigen binding. For the huLC and huFc assay, the plates were coated with anti-huFab, for the CEA binding assay, the plates were coated with CEA antigen. A summary of the results is shown in Table 1. All values are in ng/ml. Purified MN14 was used as a standard.

TABLE 1

| Clone # | MN14 CEA Activity | LC Activity | HC Activity | RATIOS HC:LC | HC:MN14 | MN14:LC |
|---|---|---|---|---|---|---|
| 1 | 211.4 | 106.6 | 433.0 | 4.06 | 2.05 | 1.98 |
| 2 |  | 198.7 | 680.6 | 3.43 |  |  |
| 5 |  | 39.9 | 189.5 | 4.75 |  |  |
| 6 | 4.8 | 287.6 | 1519.2 | 5.28 |  |  |
| 7 | 2.7 | 242.3 | 958.5 | 3.96 |  |  |
| 9 |  | 170.8 | 586.0 | 3.43 |  |  |
| 10 |  | 255.0 | 774.5 | 3.04 |  |  |
| 11 |  | 128.9 | 340.9 | 2.64 |  |  |
| 12 |  | 42.3 | 151.3 | 3.58 |  |  |
| 13 | 20.0 | 310.4 | 1482.9 | 4.78 |  |  |
| 14 | 0.6 | 220.1 | 825.4 | 3.75 |  |  |
| 15 | 1698.7 | 378.4 | 3496.1 | 9.24 | 2.06 | 4.49 |
| 16 |  | 287.2 | 1047.5 | 3.65 |  |  |
| 17 |  |  | 73.0 |  |  |  |
| 18 |  | 117.7 | 341.5 | 2.90 |  |  |
| 20 | 1375.5 | 361.2 | 2922.7 | 8.09 | 2.12 | 3.81 |
| 21 |  | 357.9 | 2824.6 | 7.89 |  |  |
| 22 | 239.3 | 209.1 | 658.2 | 3.15 | 2.75 | 1.14 |
| 23 | 2.5 | 277.7 | 1038.2 | 3.74 |  |  |
| 24 | 0.6 | 380.8 | 2136.8 | 5.61 |  |  |
| 25 |  | 322.5 | 1499.4 | 4.65 |  |  |
| 28 |  | 211.8 | 545.0 | 2.57 |  |  |
| 29 | 1383.0 | 348.1 | 2500.3 | 7.18 | 1.81 | 3.97 |
| 31 | 2213.5 | 357.7 | 3420.2 | 9.56 | 1.55 | 6.19 |
| 32 |  | 362.8 | 3256.2 | 8.97 |  |  |
| 33 | 1287.4 | 272.5 | 1329.2 | 4.88 | 1.03 | 4.72 |
| 34 |  | 297.7 | 1559.7 | 5.24 |  |  |
| 37 |  | 208.5 | 488.0 | 2.34 |  |  |
| 39 | 1953.8 | 347.0 | 2724.7 | 7.85 | 1.39 | 5.63 |
| 40 |  | 327.7 | 2762.6 | 8.43 |  |  |
| 41 |  | 294.3 | 2235.6 | 7.60 |  |  |
| 42 |  | 230.3 | 1127.2 | 4.89 |  |  |
| 43 | 1791.8 | 292.3 | 2793.4 | 9.56 | 1.56 | 6.13 |
| 44 | 682.2 | 257.3 | 1146.7 | 4.46 | 1.68 | 2.65 |
| 45 |  | 319.4 | 3475.8 | 10.88 |  |  |
| 46 | 345.0 | 265.8 | 1880.8 | 7.08 | 5.45 | 1.30 |
| 47 | 1281.5 | 241.1 | 1816.4 | 7.53 | 1.42 | 5.32 |
| 48 |  | 152.6 | 600.9 | 3.94 |  |  |

All of the 38 clones made anti-huFc reactive components—this can be assembled IgG or heavy chain. 12 out of 38 clones made CEA reactive immunoglobulin in a range between 200-2200 ng/ml. 25 out of 38 Fc reactive clones did not react with the CEA antigen. 37 out of 38 clones produced kappa light chain. The ratio of Fc reative:LC reactive components in the SNs is highest in clones producing high levels of Fc reactive components. All MN14 reactive clones are also reactive with the anti Fc antibody

EXAMPLE 2

Generation of Cell Lines Stably Expressing the MoMLV gag and pol Proteins

Example 1 describes the production of retroviral vectors containing antibody genes. These methods are generally applicable to the production of the vectors described above. The expression of the fusogenic VSV G protein on the surface of cells results in syncytium formation and cell death. Therefore, in order to produce retroviral particles containing the VSV G protein as the membrane-associated protein a two-step approach was taken. First, stable cell lines expressing the gag and pol proteins from MoMLV at high levels were generated (e.g., 293GP$^{SD}$ cells). The stable cell line, which expresses the gag and pol proteins, produces noninfectious viral particles lacking a membrane-associated protein (e.g., an envelope protein). The stable cell line was then co-transfected, using the calcium phosphate precipitation, with VSV-G and gene of interest plasmid DNAs. The pseudotyped vector generated was used to infect 293GP$^{SD}$ cells to produce stably transformed cell lines. Stable cell lines can be transiently transfected with a plasmid capable of directing the high level expression of the VSV G protein (see below). The transiently transfected cells produce VSV G-pseudotyped retroviral vectors that can be collected from the cells over a period of 3 to 4 days before the producing cells die as a result of syncytium formation.

The first step in the production of VSV G-pseudotyped retroviral vectors, the generation of stable cell lines expressing the MoMLV gag and pol proteins is described below. The human adenovirus Ad-5-transformed embryonal kidney cell line 293 (ATCC CRL 1573) was cotransfected with the pCMVgag-pol and the gene encoding for phleomycin. pCMV gag-pol contains the MoMLV gag and pol genes under the control of the CMV promoter (pCMV gag-pol is available from the ATCC).

The plasmid DNA was introduced into the 293 cells using calcium phosphate co-precipitation (Graham and Van der Eb, Virol. 52:456 [1973]). Approximately 5×10$^5$ 293 cells were plated into a 100 mm tissue culture plate the day before the DNA co-precipitate was added. Stable transformants were selected by growth in DMEM-high glucose medium containing 10% FCS and 10 µg/ml phleomycin (selective medium). Colonies that grew in the selective medium were screened for extracellular reverse transcriptase activity (Goff et al., J. Virol. 38:239 [1981]) and intracellular p30gag expression. The presence of p30gag expression was determined by Western blotting using a goat-anti p30 antibody (NCI antiserum 77S000087). A clone that exhibited stable expression of the retroviral genes was selected. This clone was named 293GP$^{SD}$ (293 gag-pol-San Diego). The 293GP$^{SD}$ cell line, a derivative of the human Ad-5-transformed embryonal kidney cell line 293, was grown in DMEM-high glucose medium containing 10% FCS.

EXAMPLE 3

Preparation of Pseudotyped Retroviral Vectors Bearing the G Glycoprotein of VSV In order to produce VSV G protein pseudotyped retrovirus the following steps were taken. The 293GP$^{SD}$ cell line was co-transfected with VSV-G plasmid and DNA plasmid of interest. This co-transfection generates the infectious particles used to infect 293GP$^{SD}$ cells to generate the packaging cell lines. This Example describes the production of pseudotyped LNBOTDC virus. This general method may be used to produce any of the vectors described in Example 1.

a) Cell Lines and Plasmids

The packaging cell line, 293GP$^{SD}$ was grown in alpha-MEM-high glucose medium containing 10% FCS. The titer of the pseudo-typed virus may be determined using either 208F cells (Quade, Virol. 98:461 [1979]) or NIH/3T3 cells (ATCC CRL 1658); 208F and NIH/3T3 cells are grown in DMEM-high glucose medium containing 10% CS.

The plasmids utilized were pLBC-L2HCF, pLBC-M4HCF, pLNC-L2LC and pLNC-M4L (See Example 1). The plasmid pHCMV-G contains the VSV G gene under the transcriptional control of the human cytomegalovirus intermediate-early promoter (Yee et al., Meth. Cell Biol. 43:99 [1994]).

b) Production of Stable Packaging Cell Lines, Pseudotyped Vector and Titering of Pseudotyped Vector DNA (SEQ ID NOs: 1, 2, 3, or 4) was co-transfected with pHCMV-G DNA into the packaging line 293GP$^{SD}$ to produce virus. The resulting virus was then used to infect 293GP$^{SD}$ cells to transform the cells. The procedure for producing pseudotyped virus was carried out as described (Yee et al., Meth. Cell Biol. 43:99 [1994].

This is a retroviral gene construct that upon creation of infectious replication defective retroviral vector will cause the insertion of the sequence described above into the cells of interest. The 3' viral LTR provides the poly-adenylation sequence for the mRNA.

Briefly, on day 1, approximately 7×10$^7$ 293GP$^{SD}$ cells were placed in a 75 cm$^2$ tissue culture flask. The flasks were incubated overnight at 37° C., 5.0% CO$_2$.

On the following day (day 2), the media in the 293GP$^{SD}$ flasks were changed with harvest medium 2 hours prior to transfection. 293GP$^{SD}$ cells were then co-transfected with 25 µg of plasmid DNA and 25 µg of VSV-G plasmid DNA using the standard calcium phosphate co-precipitation procedure (Graham and Van der Eb, Virol. 52:456 [1973]). Briefly, pHCMV-G DNA, construct DNA, 1:10 TE, and 2M CaCl$_2$ were combined and mixed. A range of 10 to 40 µg of plasmid DNA was used. 2×HBS (37° C.) was placed into a separate tube. While bubbling air through the 2×HBS, the DNA/1:10 TE/2M CaCl$_2$ mixture was added drop wise. The transfection mixture was allowed to incubate at room temperature for 20 minutes. Following the incubation period, the correct amount of transfection mixture was added to each culture vessel. The plates or flasks were returned to 37° C., 5% CO$_2$ incubator for approximately six hours. Following the incubation period, the transfections were checked for the presence of crystals/precipitate by viewing under an inverted scope. The transfection media was then removed from culture vessels by aspiration with a sterile Pasteur pipet and vacuum pump and fresh harvest medium was added to each culture vessel. The culture vessels were incubated at 37° C., 5% CO$_2$ for 24-72 hr.

On day 3, approximately 7.5×10$^5$ 293GP$^{SD}$ cells were placed in a 25 cm$^2$ tissue culture flask 24 hours prior to the harvest of the pseudotyped virus from the transfected 293GP$^{SD}$ cells. On day 4, culture medium was harvested from the transfected 293GP$^{SD}$ cells 48 hours after the application of the plasmid DNA with the gene of interest and VSV-G DNA. The culture medium was filtered through a 0.45 µm filter. The culture medium containing LNBOTDC virus was used to infect the 293GP$^{SD}$ cells as follows. The culture medium was removed from the 293GP$^{SD}$ cells and was replaced with the virus-containing culture medium. Polybrene was added to the medium at a final concentration of 8 µg/ml. The virus-containing medium was allowed to remain on the 293GP$^{SD}$ cells for 24 hours. Following the 16 hour infection period (on day 5), the medium was removed from the 293GP$^{SD}$ cells and was replaced with fresh medium containing 400 μg/ml G418 (GIBCO/BRL). The medium was changed approximately every 3 days until only those colonies that are G418-resistant colonies remain.

The G418-resistant 293GP$^{SD}$ colonies were plated as single cells in 96 wells. Sixty to one hundred G418-resistant colonies were screened for the expression of the BOTDC antibody in order to identify high producing clones. The top 10 clones in 96-well plates were transferred into 6-well plates and allowed to grow to confluency.

The top 10 clones were then expanded to screen for high titer production. Based on protein expression and titer production, 5 clonal cell lines were selected. One line was designated the master cell bank and the other 4 as backup cell lines. Pseudotyped vector was generated as follows. Approximately 7×10$^7$ 293GP$^{SD}$/cells were placed into a 75 cm$^2$ tissue culture flask. Twenty-four hours later, the cells were transfected with 25 μg of pHCMV-G plasmid DNA using calcium phosphate co-precipitation. Six to eight hours after the calcium-DNA precipitate was applied to the cells, the DNA solution was replaced with fresh culture medium (lacking G418). Longer transfection times (overnight) were found to result in the detachment of the majority of the 293GP$^{SD}$/cells from the plate and are therefore avoided. The transfected 293GP$^{SD}$/cells produce pseudotyped virus.

The pseudotyped virus generated from the transfected 293GP$^{SD}$ cells can be collected at least once a day between 24 and 96 hr after transfection. The highest virus titer was generated approximately 48 to 72 hr after initial pHCMV-G transfection. While syncytium formation became visible about 48 hr after transfection in the majority of the transfected cells, the cells continued to generate pseudotyped virus for at least an additional 48 hr as long as the cells remained attached to the tissue culture plate. The collected culture medium containing the VSV G-pseudotyped virus was pooled, filtered through a 0.45 μm filter and stored at −80° C. or concentrated immediately and then stored at −80° C.

The titer of the VSV G-pseudotyped virus was then determined as follows. Approximately 5×10$^5$ rat 208F fibroblasts cells were plated into 6 well plates. Twenty-fours hours after plating, the cells were infected with serial dilutions of the virus-containing culture medium in the presence of 8 μg/ml polybrene. Twenty four hours after infection with virus, the medium was replaced with fresh medium containing 400 μg/ml G418 and selection was continued for 14 days until only G418-resistant colonies remain. Viral titers were typically about 0.5 to 5.0×10$^6$ colony forming units (cfu)/ml. The titer of the virus stock could be concentrated to a titer of greater than 10$^9$ cfu/ml as described below.

EXAMPLE 4

Concentration of Pseudotyped Retroviral Vectors

The VSV G-pseudotyped viruses were concentrated to a high titer by one cycle of ultracentrifugation. However, in certain embodiments, two cycles are performed for further concentration. The culture medium collected and filtered as described in Example 2 which contained pseudotyped virus was transferred to Oakridge centrifuge tubes (50 ml Oakridge tubes with sealing caps, Nalge Nunc International) previously sterilized by autoclaving. The virus was sedimented in a JA20 rotor (Beckman) at 48,000×g (20,000 rpm) at 4° C. for 120 min. The culture medium was then removed from the tubes in a biosafety hood and the media remaining in the tubes was aspirated to remove the supernatant. The virus pellet was resuspended to 0.5 to 1% of the original volume in 0.1× HBSS. The resuspended virus pellet was incubated overnight at 4° C. without swirling. The virus pellet could be dispersed with gentle pipetting after the overnight incubation without significant loss of infectious virus. The titer of the virus stock was routinely increased 100- to 300-fold after one round of ultracentrifugation. The efficiency of recovery of infectious virus varied between 30 and 100%.

The virus stock was then subjected to low speed centrifugation in a microfuge for 5 min at 4° C. to remove any visible cell debris or aggregated virions that were not resuspended under the above conditions. It was noted that if the virus stock is not to be used for injection into oocytes or embryos, this centrifugation step may be omitted.

In some embodiments, the virus stock is subjected to another round of ultracentrifugation to further concentrate the virus stock. The resuspended virus from the first round of centrifugation is pooled and pelleted by a second round of ultracentrifugation that is performed as described above. Viral titers are increased approximately 2000-fold after the second round of ultracentrifugation (titers of the pseudotyped LNBOTDC virus are typically greater than or equal to 1×10$^9$ cfu/ml after the second round of ultracentrifugation).

The titers of the pre- and post-centrifugation fluids were determined by infection of 208F cells (NIH 3T3 or bovine mammary epithelial cells can also be employed) followed by selection of G418-resistant colonies as described above in Example 2.

Amplification of retroviral sequences in co-cultures may result in the generation of replication competent retroviruses, thus affecting the safety of the packaging cell line and vector production. Therefore, the cell lines were screened for production of replication competent vector. The 208F cells were expanded to approximately 30% confluency in a T25 flask (~10$^5$ cells). The cells were then infected with 5 ml of infectious vector at 10$^5$ CFU/ml+8 ug/ml polybrene and grown to confluency (~24 h), followed by the addition of media supplemented with G418. The cells were then expand to confluency and the media collected. The media from the infected cells was used to infect new 208F cells. The cells were plated in 6-well plates at 30% confluency (~10$^5$ cells) using the following dilutions: undiluted, 1:2, 1:4, 1:6, 1:8, 1:10. Cells were expanded to confluency, followed by the addition of G418. The cells were then maintained under selection for 14 days to determine the growth of any neo resistant colonies, which indicate the presence of replication competent virus.

EXAMPLE 5

Preparation of Pseudotyped Retrovirus For Infection of Host Cells

The concentrated pseudotyped retroviruses were resuspended in 0.1×HBS (2.5 mM HEPES, pH 7.12, 14 mM NaCl, 75 μM Na$_2$HPO$_4$-H$_2$O) and 18 μl aliquots were placed in 0.5 ml vials (Eppendorf) and stored at −80° C. until used. The titer of the concentrated vector was determined by diluting 1 μl of the concentrated virus 10$^{-7}$- or 10$^{-8}$-fold with 0.1×HBS. The diluted virus solution was then used to infect 208F and bovine mammary epithelial cells and viral titers were determined as described in Example 2. 8 μg/ml polybrene was added to each well. The plates were incubated for 24 hr. Media was removed from wells by aspiration with sterile Pasteur pipet and vacuum. The wells were replenished with appropriate selection medium. The media is replenished as necessary, noted by change (to yellow) in media color. In the beginning this was every two days, as fewer cells remain, the time decreased by virtue of the fact there are fewer cells. At day 10-14 (depending on selection used), the media was removed the cells were fixed with 100% methanol, 2.0 ml/well, minimum 10 minutes, washed, and stained with Giemsa stain, 2.0 ml/well, 15 minutes minimum. The number of stained colonies was counted and the titer was calculated by: average # colonies×dilution factor=# CFU/ml.

All publications and patents mentioned in the above specification are herein incorporated by reference. Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in molecular biology, protein fermentation, biochemistry, or related fields are intended to be within the scope of the following claims.

What is claimed is:

1. An isolated population of at least $10^5$ cells, containing unique antibody heavy chains and unique antibody light chains, wherein each cell comprises at least one first integrated pseudotyped retroviral vector comprising 5' and 3' long terminal repeat sequences, wherein said first pseudotyped retroviral vector comprises a promoter internal to the 5' and 3' retroviral long terminal repeats operably linked to an unique antibody light chain flanked by two recombination sites inserted in between said retroviral 5' and 3' long terminal repeats, wherein each cell further comprises at least one integrated second pseudotyped retroviral vector comprising 5' and 3' long terminal repeat sequences, wherein said second retroviral pseudotyped vector comprises a promoter internal to the 5' and 3' retroviral long terminal repeats operable linked to an unique antibody heavy chain flanked by two recombination sites inserted in between said second retroviral 5' and 3' long terminal repeats, and wherein each cell expresses a unique antibody comprising said unique heavy chain and said unique light chain encoded by said first and second integrated pseudotyped retroviral vectors.

* * * * *

SEQUENCE LISTING

```
<160> NUMBER OF SEQ ID NOS: 4

<210> SEQ ID NO 1
<211> LENGTH: 7617
<212> TYPE: DNA
<213> ORGANISM: Artificial Sequence
<220> FEATURE:
<223> OTHER INFORMATION: Synthetic

<400> SEQUENCE: 1
gaattaattc ataccagatc accgaaaact gtcctccaaa tgtgtccccc tcacactccc        60
aaattcgcgg gcttctgcct cttagaccac tctaccctat tccccacact caccggagcc      120
aaagccgcgg cccttccgtt tctttgcttt tgaaagaccc cacccgtagg tggcaagcta      180
gcttaagtaa cgccactttg caaggcatgg aaaaatacat aactgagaat agaaaagttc      240
agatcaaggt caggaacaaa gaaacagctg aataccaaac aggatatctg tggtaagcgg      300
ttcctgcccc ggctcagggc caagaacaga tgagacagct gagtgatggg ccaaacagga      360
tatctgtggt aagcagttcc tgccccggct cggggccaag aacagatggt ccccagatgc      420
ggtccagccc tcagcagttt ctagtgaatc atcagatgtt tccagggtgc cccaaggacc      480
tgaaaatgac cctgtacctt atttgaacta accaatcagt tcgcttctcg cttctgttcg      540
cgcgcttccg ctctccgagc tcaataaaag agcccacaac ccctcactcg gcgcgccagt      600
cttccgatag actgcgtcgc ccgggtaccc gtattcccaa taaagcctct tgctgtttgc      660
atccgaatcg tggtctcgct gttccttggg agggtctcct ctgagtgatt gactacccac      720 gacggggtc tttcatttgg gggctcgtcc gggatttgga gaccctgcc cagggaccac        780 cgacccacca ccgggaggta agctggccag caacttatct gtgtctgtcc gattgtctag      840
tgtctatgtt tgatgttatg cgcctgcgtc tgtactagtt agctaactag ctctgtatct      900
ggcggacccg tggtggaact gacgagttct gaacacccgg ccgcaaccct gggagacgtc      960
ccagggactt tgggggccgt ttttgtggcc cgacctgagg aagggagtcg atgtggaatc     1020
cgaccccgtc aggatatgtg gttctggtag gagacgagaa cctaaaacag ttcccgcctc     1080
cgtctgaatt tttgctttcg gtttggaacc gaagccgcgc gtcttgtctg ctgcagcgct     1140
gcagcatcgt tctgtgttgt ctctgtctga ctgtgtttct gtatttgtct gaaaattagg     1200
gccagactgt taccactccc ttaagtttga ccttaggtca ctggaaagat gtcgagcgga     1260
tcgctcacaa ccagtcggta gatgtcaaga agagacgttg ggttaccttc tgctctgcag     1320
aatggccaac ctttaacgtc ggatggccgc gagacggcac ctttaaccga gacctcatca     1380
cccaggttaa gatcaaggtc ttttcacctg gcccgcatgg acacccagac caggtcccct     1440
acatcgtgac ctgggaagcc ttggcttttg accccctcc ctgggtcaag ccctttgtac      1500
accctaagcc tccgcctcct cttcctccat ccgccccgtc tctccccctt gaacctcctc     1560
gttcgacccc gcctcgatcc tccctttatc cagccctcac tccttctcta ggcgccggaa     1620
```

```
ttccgatctg atcaagagac aggatgaggg agcttgtata tccattttcg gatctgatca    1680
gcacgtgttg acaattaatc atcggcatag tatatcggca tagtataata cgacaaggtg    1740
aggaactaaa ccatggccaa gcctttgtct caagaagaat ccaccctcat tgaaagagca    1800
acggctacaa tcaacagcat ccccatctct gaagactaca gcgtcgccag cgcagctctc    1860
tctagcgacg gccgcatctt cactggtgtc aatgtatatc attttactgg gggaccttgt    1920
gcagaactcg tggtgctggg cactgctgct gctgcggcag ctggcaaccct gacttgtatc    1980 gtcgcgatcg gaaatgagaa caggggcatc ttgagcccct gcggacggtg tcgacaggtg    2040
cttctcgatc tgcatcctgg gatcaaagcg atagtgaagg acagtgatgg acagccgacg    2100
gcagttggga ttcgtgaatt gctgccctct ggttatgtgt gggagggcta agcacttcgt    2160
ggccgaggag caggactgac acgtgctacg agatttcgat tccaccgccg ccttctatga    2220
aaggttgggc ttcggaatcg ttttccggga cgccgatccg gccattagcc atattattca    2280
ttggttatat agcataaatc aatattggct attggccatt gcatacgttg tatccatatc    2340
ataatatgta catttatatt ggctcatgtc caacattacc gccatgttga cattgattat    2400
tgactagtta ttaatagtaa tcaattacgg ggtcattagt tcatagccca tatatggagt    2460
tccgcgttac ataacttacg gtaaatggcc cgcctggctg accgcccaac gacccccgcc    2520
cattgacgtc aataatgacg tatgttccca tagtaacgcc aatagggact ttccattgac    2580
gtcaatgggt ggagtattta cggtaaactg cccacttggc agtacatcaa gtgtatcata    2640
tgccaagtac gccccctatt gacgtcaatg acggtaaatg gcccgcctgg cattatgccc    2700
agtacatgac cttatgggac tttcctactt ggcagtacat ctacgtatta gtcatcgcta    2760
ttaccatggt gatgcggttt tggcagtaca tcaatgggcg tggatagcgg tttgactcac    2820
ggggatttcc aagtctccac cccattgacg tcaatgggag tttgttttgg caccaaaatc    2880
aacgggactt tccaaaatgt cgtaacaact ccgccccatt gacgcaaatg ggcggtaggc    2940
atgtacggtg ggaggtctat ataagcagag ctcgtttagt gaaccgtcag atcgcctgga    3000
gacgccatcc acgctgtttt gacctccata agagacaccg ggaccgatcc agcctccgcg    3060
gccccaagct tgttatcaca agtttgtaca aaaaagcagg cttcgaagga gatagaacca    3120
attctctaag gaaatactta accatgggat ggagctgtat catcctcttc ttggtagcaa    3180
cagctacagg tgtccactcc caggtccagc tggtccaatc agggggctgaa gtcaagaaac    3240 ctgggtcatc agtgaaggtc tcctgcaagg cttctggcta caccttttact agctactggc    3300 tgcactgggt caggcaggca cctggacagg gtctggaatg gattggatac attaatccta    3360
ggaatgatta tactgagtac aatcagaact tcaaggacaa ggccacaata actgcagacg    3420
aatccaccaa tacagcctac atggagctga gcagcctgag gtctgaggac acggcatttt    3480 attttttgtgc aagaagggat attactacgt tctactgggg ccaaggcacc acggtcaccg    3540
tctcctcagc ctccaccaag ggcccatcgg tcttccccct ggcaccctcc tccaagagca    3600
cctctggggg cacagcggcc ctgggctgcc tggtcaagga ctacttcccc gaaccggtga    3660
cggtgtcgtg gaactcaggc gccctgacca gcggcgtgca caccttcccg gctgtcctac    3720
agtcctcagg actctactcc ctcagcagcg tggtgaccgt gccctccagc agcttgggca    3780
cccagaccta catctgcaac gtgaatcaca agcccagcaa caccaaggtg gacaagagag    3840
ttgagcccaa atcttgtgac aaaactcaca catgcccacc gtgcccagca cctgaactcc    3900
tggggggacc gtcagtcttc ctcttccccc caaaacccaa ggacaccctc atgatctccc    3960
ggacccctga ggtcacatgc gtggtggtgg acgtgagcca cgaagaccct gaggtcaagt    4020
```

```
tcaactggta cgtggacggc gtggaggtgc ataatgccaa gacaaagccg cgggaggagc    4080
agtacaacag cacgtaccgt gtggtcagcg tcctcaccgt cctgcaccag gactggctga    4140
atggcaagga gtacaagtgc aaggtctcca acaaagccct cccagccccc atcgagaaaa    4200
ccatctccaa agccaaaggg cagccccgag aaccacaggt gtacaccctg cccccatccc    4260
gggaggagat gaccaagaac caggtcagcc tgacctgcct ggtcaaaggc ttctatccca    4320
gcgacatcgc cgtggagtgg gagagcaatg ggcagccgga gaacaactac aagaccacgc    4380
ctcccgtgct ggactccgac ggctccttct cctctatag caagctcacc gtggacaaga    4440
gcaggtggca gcagggaac gtcttctcat gctccgtgat gcacgaggct ctgcacaacc    4500
actacacgca gaagagcctc tccctgtctc cgggaaatg aaagccgaat cgcggccgc    4560 actcgagata tctagaccca gctttcttgt acaaagtggt gataacatcg ataaaataaa    4620
agattttatt tagtctccag aaaaagggg gaatgaaaga ccccacctgt aggtttggca    4680
agctagctta agtaacgcca ttttgcaagg catgaaaaa tacataactg agaatagaga    4740
agttcagatc aaggtcagga acagatggaa cagctgaata tgggccaaac aggatatctg    4800
tggtaagcag ttcctgcccc ggctcagggc caagaacaga tggaacagct gaatatgggc    4860
caaacaggat atctgtggta agcagttcct gccccggctc agggccaaga acagatggtc    4920
cccagatgcg gtccagccct cagcagtttc tagagaacca tcagatgttt ccagggtgcc    4980
ccaaggacct gaaatgaccc tgtgccttat ttgaactaac caatcagttc gcttctcgct    5040
tctgttcgcg cgcttctgct ccccgagctc aataaaagag cccacaaccc ctcactcggg    5100
gcgccagtcc tccgattgac tgagtcgccc gggtacccgt gtatccaata aaccctcttg    5160
cagttgcatc cgacttgtgg tctcgctgtt ccttgggagg gtctcctctg agtgattgac    5220
tacccgtcag cgggggtctt tcattttttcc attgggggct cgtccgggat cgggagaccc    5280
ctgcccaggg accaccgacc caccaccggg aggtaagctg gctgcctcgc gcgtttcggt    5340
gatgacggtg aaaacctctg acacatgcag ctcccggaga cggtcacagc ttgtctgtaa    5400
gcggatgccg ggagcagaca gcccgtcag ggcgcgtcag cgggtgttgg cgggtgtcgg    5460
ggcgcagcca tgacccagtc acgtagcgat agcggagtgt atactggctt aactatgcgg    5520
catcagagca gattgtactg agagtgcacc atatgcggtg tgaaataccg cacagatgcg    5580
taaggagaaa ataccgcatc aggcgctctt ccgcttcctc gctcactgac tcgctgcgct    5640
cggtcgttcg gctgcggcga gcggtatcag ctcactcaaa ggcggtaata cggttatcca    5700
cagaatcagg ggataacgca ggaaagaaca tgtgagcaaa aggccagcaa aaggccagga    5760
accgtaaaaa ggccgcgttg ctggcgtttt tccataggct ccgcccccct gacgagcatc    5820
acaaaaatcg acgctcaagt cagaggtggc gaaacccgac aggactataa agataccagg    5880
cgtttccccc tggaagctcc ctcgtgcgct ctcctgttcc gaccctgccg cttaccggat    5940
acctgtccgc ctttctccct tcgggaagcg tggcgctttc tcatagctca cgctgtaggt    6000
atctcagttc ggtgtaggtc gttcgctcca agctgggctg tgtgcacgaa ccccccgttc    6060
agcccgaccg ctgcgcctta tccggtaact atcgtcttga gtccaacccg gtaagacacg    6120
acttatcgcc actggcagca gccactggta acaggattag cagagcgagg tatgtaggcg    6180
gtgctacaga gttcttgaag tggtggccta actacggcta cactagaagg acagtatttg    6240
gtatctgcgc tctgctgaag ccagttacct tcggaaaaag agttggtagc tcttgatccg    6300
gcaaacaaac caccgctggt agcggtggtt tttttgtttg caagcagcag attacgcgca    6360
gaaaaaaagg atctcaagaa gatcctttga tcttttctac ggggtctgac gctcagtgga    6420
```

```
acgaaaactc acgttaaggg attttggtca tgagattatc aaaaaggatc ttcacctaga    6480
tccttttaaa ttaaaaatga agttttaaat caatctaaag tatatatgag taaacttggt    6540
ctgacagtta ccaatgctta atcagtgagg cacctatctc agcgatctgt ctatttcgtt    6600
catccatagt tgcctgactc cccgtcgtgt agataactac gatacgggag ggcttaccat    6660
ctggccccag tgctgcaatg ataccgcgag acccacgctc accggctcca gatttatcag    6720
caataaacca gccagccgga agggccgagc gcagaagtgg tcctgcaact ttatccgcct    6780
ccatccagtc tattaattgt tgccgggaag ctagagtaag tagttcgcca gttaatagtt    6840
tgcgcaacgt tgttgccatt gctgcaggca tcgtggtgtc acgctcgtcg tttggtatgg    6900
cttcattcag ctccggttcc caacgatcaa ggcgagttac atgatccccc atgttgtgca    6960
aaaaagcggt tagctccttc ggtcctccga tcgttgtcag aagtaagttg gccgcagtgt    7020
tatcactcat ggttatggca gcactgcata attctcttac tgtcatgcca tccgtaagat    7080
gcttttctgt gactggtgag tactcaacca agtcattctg agaatagtgt atgcggcgac    7140
cgagttgctc ttgcccggcg tcaacacggg ataataccgc gccacatagc agaactttaa    7200
aagtgctcat cattggaaaa cgttcttcgg ggcgaaaact ctcaaggatc ttaccgctgt    7260
tgagatccag ttcgatgtaa cccactcgtg cacccaactg atcttcagca tcttttactt    7320
tcaccagcgt ttctgggtga gcaaaaacag gaaggcaaaa tgccgcaaaa aagggaataa    7380
gggcgacacg gaaatgttga atactcatac tcttcctttt tcaatattat tgaagcattt    7440
atcagggtta ttgtctcatg agcggataca tatttgaatg tatttagaaa aataaacaaa    7500
taggggttcc gcgcacattt ccccgaaaag tgccacctga cgtctaagaa accattatta    7560
tcatgacatt aacctataaa aataggcgta tcacgaggcc ctttcgtctt caagaat       7617

<210> SEQ ID NO 2
<211> LENGTH: 7626
<212> TYPE: DNA
<213> ORGANISM: Artificial Sequence
<220> FEATURE:
<223> OTHER INFORMATION: Synthetic

<400> SEQUENCE: 2
gaattaattc ataccagatc accgaaaact gtcctccaaa tgtgtccccc tcacactccc      60
aaattcgcgg gcttctgcct cttagaccac tctaccctat tccccacact caccggagcc     120
aaagccgcgg cccttccgtt tctttgcttt tgaaagaccc caccgtagg tggcaagcta      180 gcttaagtaa cgccactttg caaggcatgg aaaaatacat aactgagaat agaaaagttc     240
agatcaaggt caggaacaaa gaaacagctg aataccaaac aggatatctg tggtaagcgg     300
ttcctgcccc ggctcagggc caagaacaga tgagacagct gagtgatggg ccaaacagga    360
tatctgtggt aagcagttcc tgccccggct cggggccaag aacagatggt ccccagatgc    420
ggtccagccc tcagcagttt ctagtgaatc atcagatgtt tccagggtgc cccaaggacc    480
tgaaaatgac cctgtacctt atttgaacta accaatcagt tcgcttctcg cttctgttcg    540
cgcgcttccg ctctccgagc tcaataaaag agcccacaac ccctcactcg gcgcgccagt    600
cttccgatag actgcgtcgc ccgggtaccc gtattcccaa taaagcctct tgctgtttgc    660
atccgaatcg tggtctcgct gttccttggg agggtctcct ctgagtgatt gactacccac    720 gacggggtc tttcatttgg gggctcgtcc gggatttgga cccctgcc cagggaccac       780 cgacccacca ccgggaggta agctggccag caacttatct gtgtctgtcc gattgtctag    840
tgtctatgtt tgatgttatg cgcctgcgtc tgtactagtt agctaactag ctctgtatct    900
```

```
ggcggacccg tggtggaact gacgagttct gaacacccgg ccgcaaccct gggagacgtc    960
ccagggactt tgggggccgt ttttgtggcc cgacctgagg aagggagtcg atgtggaatc   1020
cgaccccgtc aggatatgtg gttctggtag gagacgagaa cctaaaacag ttcccgcctc   1080
cgtctgaatt tttgctttcg gtttggaacc gaagccgcgc gtcttgtctg ctgcagcgct   1140
gcagcatcgt tctgtgttgt ctctgtctga ctgtgtttct gtatttgtct gaaaattagg   1200
gccagactgt taccactccc ttaagtttga ccttaggtca ctggaaagat gtcgagcgga   1260
tcgctcacaa ccagtcggta gatgtcaaga agagacgttg ggttaccttc tgctctgcag   1320
aatggccaac ctttaacgtc ggatggccgc gagacggcac ctttaaccga gacctcatca   1380
cccaggttaa gatcaaggtc ttttcacctg gcccgcatgg acacccagac caggtccccct  1440
acatcgtgac ctgggaagcc ttggcttttg acccccctcc ctgggtcaag ccctttgtac   1500
accctaagcc tccgcctcct cttcctccat ccgcccgtc tctccccctt gaacctcctc    1560
gttcgacccc gcctcgatcc tcccttatc cagccctcac tccttctcta ggcgccggaa    1620
ttccgatctg atcaagagac aggatgaggg agcttgtata tccattttcg gatctgatca   1680
gcacgtgttg acaattaatc atcggcatag tatatcggca tagtataata cgacaaggtg   1740
aggaactaaa ccatggccaa gcctttgtct caagaagaat ccaccctcat gaaagagca    1800
acggctacaa tcaacagcat ccccatctct gaagactaca cgtcgccag cgcagctctc    1860
tctagcgacg gccgcatctt cactggtgtc aatgtatatc attttactgg gggaccttgt   1920
gcagaactcg tggtgctggg cactgctgct gctgcggcag ctggcaacct gacttgtatc   1980
gtcgcgatcg gaaatgagaa cagggggcatc ttgagcccct gcggacggtg tcgacaggtg  2040
cttctcgatc tgcatcctgg gatcaaagcg atagtgaagg acagtgatgg acagccgacg   2100
gcagttggga ttcgtgaatt gctgccctct ggttatgtgt gggagggcta agcacttcgt   2160
ggccgaggag caggactgac acgtgctacg agatttcgat tccaccgccg ccttctatga   2220
aaggttgggc ttcggaatcg ttttccggga cgccgatccg gccattagcc atattattca   2280
ttggttatat agcataaatc aatattggct attggccatt gcatacgttg tatccatatc   2340
ataatatgta catttatatt ggctcatgtc caacattacc gccatgttga cattgattat   2400
tgactagtta ttaatagtaa tcaattacgg ggtcattagt tcatagccca tatatggagt   2460
tccgcgttac ataacttacg gtaaatggcc cgcctggctg accgcccaac gaccccgcc   2520
cattgacgtc aataatgacg tatgttccca tagtaacgcc aatagggact ttccattgac   2580
gtcaatgggt ggagtattta cggtaaactg cccacttggc agtacatcaa gtgtatcata   2640
tgccaagtac gccccctatt gacgtcaatg acggtaaatg gcccgcctgg cattatgccc   2700
agtacatgac cttatgggac tttcctactt ggcagtacat ctacgtatta gtcatcgcta   2760
ttaccatggt gatgcggttt tggcagtaca tcaatgggcg tggatagcgg tttgactcac   2820
ggggatttcc aagtctccac cccattgacg tcaatgggag tttgttttgg caccaaaatc   2880
aacgggactt tccaaaatgt cgtaacaact ccgccccatt gacgcaaatg ggcggtaggc   2940
atgtacggtg ggaggtctat ataagcagag ctcgtttagt gaaccgtcag atcgcctgga   3000
gacgccatcc acgctgtttt gacctccata aagacaccg ggaccgatcc agcctccgcg    3060
gccccaagct tgttatcaca gtttgtaca aaaaagcagg cttcgaagga gatagaacca    3120
attctctaag gaaatactta accatgggat ggagctgtat catcctcttc ttggtagcaa   3180
cagctacagg tgtccactcc gaggtccaac tggtggagag cggtggaggt gttgtgcaac   3240
ctggccggtc cctgcgcctg tcctgctccg catctggctt cgatttcacc acatattgga   3300
```

```
tgagttgggt gagacaggca cctggaaaag gtcttgagtg gattggagaa attcatccag    3360
atagcagtac gattaactat gcgccgtctc taaaggatag atttacaata tcgcgagaca    3420
acgccaagaa cacattgttc ctgcaaatgg acagcctgag acccgaagac accggggtct    3480 attttttgtgc aagcctttac ttcggcttcc cctggtttgc ttattggggc caagggaccc    3540
cggtcaccgt ctcctcagcc tccaccaagg gcccatcggt cttccccctg gcaccctcct    3600
ccaagagcac ctctgggggc acagcggccc tgggctgcct ggtcaaggac tacttccccg    3660
aaccggtgac ggtgtcgtgg aactcaggcg ccctgaccag cggcgtgcac accttcccgg    3720
ctgtcctaca gtcctcagga ctctactccc tcagcagcgt ggtgaccgtg ccctccagca    3780
gcttgggcac ccagacctac atctgcaacg tgaatcacaa gcccagcaac accaaggtgg    3840
acaagagagt tgagcccaaa tcttgtgaca aaactcacac atgcccaccg tgcccagcac    3900
ctgaactcct ggggggaccg tcagtcttcc tcttcccccc aaaacccaag gacaccctca    3960
tgatctcccg gacccctgag gtcacatgcg tggtggtgga cgtgagccac gaagaccctg    4020
aggtcaagtt caactggtac gtggacggcg tggaggtgca taatgccaag acaaagccgc    4080
gggaggagca gtacaacagc acgtaccgtg tggtcagcgt cctcaccgtc ctgcaccagg    4140
actggctgaa tggcaaggag tacaagtgca aggtctccaa caaagccctc ccagccccca    4200
tcgagaaaac catctccaaa gccaaagggc agccccgaga accacaggtg tacaccctgc    4260
ccccatcccg ggaggagatg accaagaacc aggtcagcct gacctgcctg gtcaaaggct    4320
tctatcccag cgacatcgcc gtggagtggg agagcaatgg gcagccggag aacaactaca    4380
agaccacgcc tcccgtgctg gactccgacg gctccttctt cctctatagc aagctcaccg    4440
tggacaagag caggtggcag caggggaacg tcttctcatg ctccgtgatg cacgaggctc    4500
tgcacaacca ctacacgcag aagagcctct ccctgtctcc gggaaatgaa agccgaatt    4560 cgcggccgca ctcgagatat ctagacccag cttctcttgta caaagtggtg ataacatcga    4620
taaaataaaa gatttttattt agtctccaga aaaaggggggg aatgaaagac cccacctgta    4680
ggtttggcaa gctagcttaa gtaacgccat tttgcaaggc atggaaaaat acataactga    4740
gaatagagaa gttcagatca aggtcaggaa cagatggaac agctgaatat gggccaaaca    4800
ggatatctgt ggtaagcagt tcctgccccg gctcagggcc aagaacagat ggaacagctg    4860
aatatgggcc aaacaggata tctgtggtaa gcagttcctg ccccggctca gggccaagaa    4920
cagatggtcc ccagatgcgg tccagccctc agcagtttct agagaaccat cagatgtttc    4980
cagggtgccc caaggacctg aaatgaccct gtgccttatt tgaactaacc aatcagttcg    5040
cttctcgctt ctgttcgcgc gcttctgctc ccgagctca ataaaagagc ccacaacccc    5100
tcactcgggg cgccagtcct ccgattgact gagtcgcccg ggtacccgtg tatccaataa    5160
accctcttgc agttgcatcc gacttgtggt ctcgctgttc cttgggaggg tctcctctga    5220
gtgattgact accecgtcagc gggggtcttt cattttttcca ttggggctc gtccgggatc    5280 gggagacccc tgcccaggga ccaccgaccc accaccggga ggtaagctgg ctgcctcgcg    5340
cgtttcggtg atgacggtga aacctctga cacatgcagc tcccgagac ggtcacagct    5400 tgtctgtaag cggatgccgg gagcagacaa gcccgtcagg gcgcgtcagc gggtgttggc    5460
gggtgtcggg gcgcagccat gacccagtca cgtagcgata gcggagtgta tactggctta    5520
actatgcggc atcagagcag attgtactga gagtgcacca tatgcggtgt gaaataccgc    5580
acagatgcgt aaggagaaaa taccgcatca ggcgctcttc cgcttcctcg ctcactgact    5640
cgctgcgctc ggtcgttcgg ctgcggcgag cggtatcagc tcactcaaag gcggtaatac    5700
```

| | | |
|---|---|---|
| ggttatccac agaatcaggg gataacgcag gaaagaacat gtgagcaaaa ggccagcaaa | 5760 | |
| aggccaggaa ccgtaaaaag gccgcgttgc tggcgttttt ccataggctc cgcccccctg | 5820 | |
| acgagcatca caaaaatcga cgctcaagtc agaggtggcg aaacccgaca ggactataaa | 5880 | |
| gataccaggc gtttccccct ggaagctccc tcgtgcgctc tcctgttccg accctgccgc | 5940 | |
| ttaccggata cctgtccgcc tttctccctt cgggaagcgt ggcgctttct catagctcac | 6000 | |
| gctgtaggta tctcagttcg gtgtaggtcg ttcgctccaa gctgggctgt gtgcacgaac | 6060 | |
| cccccgttca gcccgaccgc tgcgccttat ccggtaacta tcgtcttgag tccaacccgg | 6120 | |
| taagacacga cttatcgcca ctggcagcag ccactggtaa caggattagc agagcgaggt | 6180 | |
| atgtaggcgg tgctacagag ttcttgaagt ggtggcctaa ctacggctac actagaagga | 6240 | |
| cagtatttgg tatctgcgct ctgctgaagc cagttacctt cggaaaaaga gttggtagct | 6300 | |
| cttgatccgg caaacaaacc accgctggta gcggtggttt ttttgtttgc aagcagcaga | 6360 | |
| ttacgcgcag aaaaaaagga tctcaagaag atcctttgat cttttctacg ggtctgacg | 6420 | |
| ctcagtggaa cgaaaactca cgttaaggga ttttggtcat gagattatca aaaaggatct | 6480 | |
| tcacctagat ccttttaaat taaaatgaa gttttaaatc aatctaaagt atatatgagt | 6540 | |
| aaacttggtc tgacagttac caatgcttaa tcagtgaggc acctatctca gcgatctgtc | 6600 | |
| tatttcgttc atccatagtt gcctgactcc ccgtcgtgta gataactacg atacgggagg | 6660 | |
| gcttaccatc tggccccagt gctgcaatga taccgcgaga cccacgctca ccggctccag | 6720 | |
| atttatcagc aataaaccag ccagccgaa gggccgagcg cagaagtggt cctgcaactt | 6780 | |
| tatccgcctc catccagtct attaattgtt gccgggaagc tagagtaagt agttcgccag | 6840 | |
| ttaatagttt gcgcaacgtt gttgccattg ctgcaggcat cgtggtgtca cgctcgtcgt | 6900 | |
| ttggtatggc ttcattcagc tccggttccc aacgatcaag gcgagttaca tgatccccca | 6960 | |
| tgttgtgcaa aaaagcggtt agctccttcg gtcctccgat cgttgtcaga agtaagttgg | 7020 | |
| ccgcagtgtt atcactcatg gttatggcag cactgcataa ttctcttact gtcatgccat | 7080 | |
| ccgtaagatg cttttctgtg actggtgagt actcaaccaa gtcattctga atagtgta | 7140 | |
| tgcggcgacc gagttgctct tgcccggcgt caacacggga taataccgcg ccacatagca | 7200 | |
| gaactttaaa agtgctcatc attggaaaac gttcttcggg gcgaaaactc tcaaggatct | 7260 | |
| taccgctgtt gagatccagt tcgatgtaac ccactcgtgc acccaactga tcttcagcat | 7320 | |
| cttttacttt caccagcgtt tctgggtgag caaaaacagg aaggcaaaat gccgcaaaaa | 7380 | |
| agggaataag ggcgacacgg aaatgttgaa tactcatact cttcctttt caatattatt | 7440 | |
| gaagcattta tcagggttat tgtctcatga gcggatacat atttgaatgt atttagaaaa | 7500 | |
| ataaacaaat aggggttccg cgcacatttc cccgaaaagt gccacctgac gtctaagaaa | 7560 | |
| ccattattat catgacatta acctataaaa ataggcgtat cacgaggccc tttcgtcttc | 7620 | |
| aagaat | 7626 | |

<210> SEQ ID NO 3
<211> LENGTH: 7490
<212> TYPE: DNA
<213> ORGANISM: Artificial Sequence
<220> FEATURE:
<223> OTHER INFORMATION: Synthetic

<400> SEQUENCE: 3

| | | |
|---|---|---|
| gaattaattc ataccagatc accgaaaact gtcctccaaa tgtgtccccc tcacactccc | 60 | |
| aaattcgcgg gcttctgcct cttagaccac tctaccctat tccccacact caccggagcc | 120 | |

```
aaagccgcgg cccttccgtt tctttgcttt tgaaagaccc cacccgtagg tggcaagcta    180
gcttaagtaa cgccactttg caaggcatgg aaaatacat aactgagaat agaaaagttc     240
agatcaaggt caggaacaaa gaaacagctg aataccaaac aggatatctg tggtaagcgg    300
ttcctgcccc ggctcagggc caagaacaga tgagacagct gagtgatggg ccaaacagga    360
tatctgtggt aagcagttcc tgccccggct cggggccaag aacagatggt ccccagatgc    420
ggtccagccc tcagcagttt ctagtgaatc atcagatgtt tccagggtgc cccaaggacc    480
tgaaaatgac cctgtacctt atttgaacta accaatcagt tcgcttctcg cttctgttcg    540
cgcgcttccg ctctccgagc tcaataaaag agcccacaac ccctcactcg gcgcgccagt    600
cttccgatag actgcgtcgc ccgggtaccc gtattcccaa taaagcctct tgctgtttgc    660
atccgaatcg tggtctcgct gttccttggg agggtctcct ctgagtgatt gactaccac     720 gacgggggtc tttcatttgg gggctcgtcc gggatttgga daccctgcc cagggaccac     780 cgacccacca ccgggaggta agctggccag caacttatct gtgtctgtcc gattgtctag    840
tgtctatgtt tgatgttatg cgcctgcgtc tgtactagtt agctaactag ctctgtatct    900
ggcggacccg tggtggaact gacgagttct gaacacccgg ccgcaaccct gggagacgtc    960
ccagggactt tgggggccgt ttttgtggcc cgacctgagg aagggagtcg atgtggaatc   1020
cgaccccgtc aggatatgtg gttcggtag agacgagaa cctaaaacag ttcccgcctc    1080
cgtctgaatt tttgctttcg gtttggaacc gaagccgcgc gtcttgtctg ctgcagcgct   1140
gcagcatcgt tctgtgttgt ctctgtctga ctgtgtttct gtatttgtct gaaaattagg   1200
gccagactgt taccactccc ttaagtttga ccttaggtca ctggaaagat gtcgagcgga   1260
tcgctcacaa ccagtcggta gatgtcaaga agagacgttg ggttaccttc tgctctgcag   1320
aatggccaac cttaacgtc ggatggccgc gagacggcac ctttaaccga gacctcatca    1380
cccaggttaa gatcaaggtc ttttcacctg gcccgcatgg acacccagac caggtccccct  1440 acatcgtgac ctgggaagcc ttggcttttg accccctcc ctgggtcaag cccttgtac     1500 accctaagcc tccgcctcct cttcctccat ccgccccgtc tctccccctt gaacctcctc   1560
gttcgacccc gcctcgatcc tccctttatc cagccctcac tccttctcta ggcgccggaa   1620
ttccgatctg atcaagagac aggatgagga tcgtttcgca tgattgaaca agatggattg   1680
cacgcaggtt ctccggccgc ttgggtggag aggctattcg gctatgactg ggcacaacag   1740
acaatcggct gctctgatgc cgccgtgttc cggctgtcag cgcaggggcg cccggttctt   1800
tttgtcaaga ccgacctgtc cggtgccctg aatgaactgc aggacgaggc agcgcggcta   1860
tcgtggctgg ccacgacggg cgttccttgc gcagctgtgc tcgacgttgt cactgaagcg   1920
ggaagggact ggctgctatt gggcgaagtg ccggggcagg atctcctgtc atctcacctt   1980
gctcctgccg agaaagtatc catcatggct gatgcaatgc ggcggctgca tacgcttgat   2040
ccggctacct gcccattcga ccaccaagcg aaacatcgca tcgagcgagc acgtactcgg   2100
atggaagccg gtcttgtcga tcaggatgat ctggacgaag agcatcaggg gctcgcgcca   2160
gccgaactgt tcgccaggct caaggcgcgc atgcccgacg cgaggatct cgtcgtgacc    2220 catggcgatg cctgcttgcc gaatatcatg gtgaaaatg ccgcttttc tggattcatc     2280 gactgtggcc ggctgggtgt ggcggaccgc tatcaggaca tagcgttggc tacccgtgat   2340
attgctgaag agcttggcgg cgaatgggct gaccgcttcc tcgtgcttta cggtatcgcc   2400
gctcccgatt cgcagcgcat cgccttctat cgccttcttg acgagttctt ctgagcggga   2460
ctctggggtt cgaaatgacc gaccaagcga cgcccaacct gccatcacga gatttcgatt   2520
```

```
ccaccgccgc cttctatgaa aggttgggct tcggaatcgt tttccgggac gccggctgga   2580
tgatcctcca gcgcgggat ctcatgctgg agttcttcgc ccaccccggg ctcgatcccc    2640
tcgcgagttg gttcagctgc tgcctgaggc tggacgacct cgcggagttc taccggcagt   2700
gcaaatccgt cggcatccag gaaaccagca gcggctatcc gcgcatccat gcccccgaac   2760
tgcaggagtg gggaggcacg atggccgctt tggtcgaggc ggatccggcc attagccata   2820
ttattcattg gttatatagc ataaatcaat attggctatt ggccattgca tacgttgtat   2880
ccatatcata atatgtacat ttatattggc tcatgtccaa cattaccgcc atgttgacat   2940
tgattattga ctagttatta atagtaatca attacggggt cattagttca tagcccatat   3000
atggagttcc gcgttacata acttacggta aatggcccgc ctggctgacc gcccaacgac   3060
ccccgcccat tgacgtcaat aatgacgtat gttcccatag taacgccaat agggactttc   3120
cattgacgtc aatgggtgga gtatttacgg taaactgccc acttggcagt acatcaagtg   3180
tatcatatgc caagtacgcc ccctattgac gtcaatgacg gtaaatggcc cgcctggcat   3240
tatgcccagt acatgacctt atgggacttt cctacttggc agtacatcta cgtattagtc   3300
atcgctatta ccatggtgat gcggttttgg cagtacatca atgggcgtgg atagcggttt   3360
gactcacggg gatttccaag tctccacccc attgacgtca atgggagttt gttttggcac   3420
caaaatcaac gggactttcc aaaatgtcgt aacaactccg ccccattgac gcaaatgggc   3480
ggtaggcatg tacggtggga ggtctatata agcagagctc gtttagtgaa ccgtcagatc   3540
gcctggagac gccatccacg ctgttttgac ctccatagaa gacaccggga ccgatccagc   3600
ctccgcggcc ccaagcttgt tatcacaagt ttgtacaaaa aagcaggctt cgaaggagat   3660
agaaccaatt ctctaaggaa atacttaacg tcgactggat ccggtaccga attcggcgcc   3720
gccaccatga tgtcctttgt ctctctgctc ctggtaggca tcctattcca tgccacccag   3780
gccgacatcc agctgaccca gtctccatca tctctgagcg catctgttgg agatagggtc   3840
actatgagct gtaagtccag tcaaagtgtt ttatacagtg caaatcacaa gaactacttg   3900
gcctggtacc agcagaaacc agggaaagca cctaaactgc tgatctactg ggcatccact   3960
agggaatctg gtgtcccttc gcgattctct ggcagcggat ctgggacaga ttttactttc   4020
accatcagct ctcttcaacc agaagacatt gcaacatatt attgtcacca ataccteecc   4080
tcgtggacgt tcggtggagg gaccaaggtg cagatcaaac gaactgtggc tgcaccatct   4140
gtcttcatct tcccgccatc tgatgagcag ttgaaatctg gaactgcctc tgttgtgtgc   4200
ctgctgaata acttctatcc cagagaggcc aaagtacagt ggaaggtgga taacgccctc   4260
caatcgggta actcccagga gagtgtcaca gagcaggaca gcaaggacag cacctacagc   4320
ctcagcagca ccctgacgct gagcaaagca gactacgaga aacacaaagt ctacgcctgc   4380
gaagtcaccc atcagggcct gagctcgccc gtcacaaaga gcttcaacag gggagagtgt   4440
tagatctcga gatatctaga cccagctttc ttgtacaaag tggtgataac atcgataaaa   4500
taaaagattt tatttagtct ccagaaaaag gggggaatga agacccccac ctgtaggttt   4560
ggcaagctag cttaagtaac gccattttgc aaggcatgga aaaatacata actgagaata   4620
gagaagttca gatcaaggtc aggaacagat ggaacagctg aatatgggcc aaacaggata   4680
tctgtggtaa gcagttcctg ccccggctca gggccaagaa cagatggaac agctgaatat   4740
gggccaaaca ggatatctgt ggtaagcagt tcctgccccg gctcagggcc aagaacagat   4800
ggtccccaga tgcggtccag ccctcagcag tttctagaga accatcagat gtttccaggg   4860
tgccccaagg acctgaaatg accctgtgcc ttatttgaac taaccaatca gttcgcttct   4920
```

```
cgcttctgtt cgcgcgcttc tgctccccga gctcaataaa agagcccaca accccctcact    4980 cggggcgcca gtcctccgat tgactgagtc gcccgggtac ccgtgtatcc aataaaccct    5040
cttgcagttg catccgactt gtggtctcgc tgttccttgg gagggtctcc tctgagtgat    5100
tgactacccg tcagcggggg tctttcattt gggggctcgt ccgggatcgg gagacccctg    5160 cccaggacc accgacccac caccgggagg taagctggct gcctcgcgcg tttcggtgat     5220
gacggtgaaa acctctgaca catgcagctc ccggagacgg tcacagcttg tctgtaagcg    5280
gatgccggga gcagacaagc ccgtcagggc gcgtcagcgg gtgttggcgg gtgtcggggc    5340
gcagccatga cccagtcacg tagcgatagc ggagtgtata ctggcttaac tatgcggcat    5400
cagagcagat tgtactgaga gtgcaccata tgcggtgtga ataccgcac agatgcgtaa     5460 ggagaaaata ccgcatcagg cgctcttccg cttcctcgct cactgactcg ctgcgctcgg    5520
tcgttcggct gcggcgagcg gtatcagctc actcaaaggc ggtaatacgg ttatccacag    5580
aatcagggga taacgcagga agaacatgt gagcaaaagg ccagcaaaag gccaggaacc     5640
gtaaaaaggc cgcgttgctg cgttttttcc ataggctccg ccccctgac gagcatcaca     5700 aaaatcgacg ctcaagtcag aggtggcgaa acccgacagg actataaaga taccaggcgt    5760
ttccccctgg aagctccctc gtgcgctctc ctgttccgac cctgccgctt accggatacc    5820
tgtccgcctt tctcccttcg ggaagcgtgg cgctttctca tagctcacgc tgtaggtatc    5880
tcagttcggt gtaggtcgtt cgctccaagc tgggctgtgt gcacgaaccc cccgttcagc    5940
ccgaccgctg cgccttatcc ggtaactatc gtcttgagtc aacccggta agacacgact     6000 tatcgccact ggcagcagcc actggtaaca ggattagcag agcgaggtat gtaggcggtg    6060
ctacagagtt cttgaagtgg tggcctaact acggctacac tagaaggaca gtatttggta    6120
tctgcgctct gctgaagcca gttaccttcg gaaaaagagt tggtagctct tgatccggca    6180
aacaaaccac cgctggtagc ggtggttttt ttgtttgcaa gcagcagatt acgcgcagaa    6240
aaaaaggatc tcaagaagat cctttgatct tttctacggg gtctgacgct cagtggaacg    6300
aaaactcacg ttaagggatt ttggtcatga gattatcaaa aaggatcttc acctagatcc    6360
ttttaaatta aaaatgaagt tttaaatcaa tctaaagtat atatgagtaa acttggtctg    6420
acagttacca atgcttaatc agtgaggcac ctatctcagc gatctgtcta tttcgttcat    6480
ccatagttgc ctgactcccc gtcgtgtaga taactacgat acgggagggc ttaccatctg    6540
gccccagtgc tgcaatgata ccgcgagacc cacgctcacc ggctccagat ttatcagcaa    6600
taaaccagcc agccggaagg gccgagcgca gaagtggtcc tgcaacttta tccgcctcca    6660
tccagtctat taattgttgc cgggaagcta gagtaagtag ttcgccagtt aatagtttgc    6720
gcaacgttgt tgccattgct gcaggcatcg tggtgtcacg ctcgtcgttt ggtatggctt    6780
cattcagctc cggttcccaa cgatcaaggc gagttacatg atccccatg ttgtgcaaaa     6840 aagcggttag ctccttcggt cctccgatcg ttgtcagaag taagttggcc gcagtgttat    6900
cactcatggt tatggcagca ctgcataatt ctcttactgt catgccatcc gtaagatgct    6960
tttctgtgac tggtgagtac tcaaccaagt cattctgaga atagtgtatg cggcgaccga    7020
gttgctcttg cccggcgtca cacgggata ataccgcgcc acatagcaga actttaaaag    7080
tgctcatcat tggaaaacgt tcttcgggc gaaaactctc aaggatctta ccgctgttga     7140
gatccagttc gatgtaaccc actcgtgcac ccaactgatc ttcagcatct tttactttca    7200
ccagcgtttc tgggtgagca aaaacaggaa ggcaaaatgc cgcaaaaaag ggaataaggg    7260
cgacacggaa atgttgaata ctcatactct tccttttca atattattga agcatttatc     7320
```

-continued

| | |
|---|---|
| agggttattg tctcatgagc ggatacatat ttgaatgtat ttagaaaaat aaacaaatag | 7380 |
| gggttccgcg cacatttccc cgaaaagtgc cacctgacgt ctaagaaacc attattatca | 7440 |
| tgacattaac ctataaaaat aggcgtatca cgaggccctt tcgtcttcaa | 7490 |

<210> SEQ ID NO 4
<211> LENGTH: 7472
<212> TYPE: DNA
<213> ORGANISM: Artificial Sequence
<220> FEATURE:
<223> OTHER INFORMATION: Synthetic

<400> SEQUENCE: 4

| | |
|---|---|
| gaattaattc ataccagatc accgaaaact gtcctccaaa tgtgtccccc tcacactccc | 60 |
| aaattcgcgg gcttctgcct cttagaccac tctaccctat tccccacact caccggagcc | 120 |
| aaagccgcgg cccttccgtt tctttgcttt tgaaagaccc caccccgtagg tggcaagcta | 180 |
| gcttaagtaa cgccactttg caaggcatgg aaaaatacat aactgagaat agaaaagttc | 240 |
| agatcaaggt caggaacaaa gaaacagctg aataccaaac aggatatctg tggtaagcgg | 300 |
| ttcctgcccc ggctcagggc caagaacaga tgagacagct gagtgatggg ccaaacagga | 360 |
| tatctgtggt aagcagttcc tgccccggct cggggccaag aacagatggt ccccagatgc | 420 |
| ggtccagccc tcagcagttt ctagtgaatc atcagatgtt tccagggtgc ccaaggacc | 480 |
| tgaaaatgac cctgtacctt atttgaacta accaatcagt tcgcttctcg cttctgttcg | 540 |
| cgcgcttccg ctctccgagc tcaataaaag agcccacaac ccctcactcg gcgcgccagt | 600 |
| cttccgatag actgcgtcgc ccgggtaccc gtattcccaa taaagcctct tgctgtttgc | 660 |
| atccgaatcg tggtctcgct gttccttggg agggtctcct ctgagtgatt gactacccac | 720 |
| gacggggggtc tttcatttgg gggctcgtcc gggatttgga gaccctgcc cagggaccac | 780 |
| cgacccacca ccgggaggta agctggccag caacttatct gtgtctgtcc gattgtctag | 840 |
| tgtctatgtt tgatgttatg cgcctgcgtc tgtactagtt agctaactag ctctgtatct | 900 |
| ggcggacccg tggtggaact gacgagttct gaacacccgg ccgcaaccct gggagacgtc | 960 |
| ccagggactt tgggggccgt ttttgtggcc cgacctgagg aagggagtcg atgtggaatc | 1020 |
| cgacccccgtc aggatatgtg gttctggtag gagacgagaa cctaaaacag ttcccgcctc | 1080 |
| cgtctgaatt tttgctttcg gtttggaacc gaagccgcgc gtcttgtctg ctgcagcgct | 1140 |
| gcagcatcgt tctgtgttgt ctctgtctga ctgtgtttct gtatttgtct gaaaattagg | 1200 |
| gccagactgt taccactccc ttaagtttga ccttaggtca ctggaaagat gtcgagcgga | 1260 |
| tcgctcacaa ccagtcggta gatgtcaaga agagacgttg ggttaccttc tgctctgcag | 1320 |
| aatggccaac ctttaacgtc ggatggccgc gagacggcac ctttaaccga gacctcatca | 1380 |
| cccaggttaa gatcaaggtc ttttcacctg gcccgcatgg acacccagac caggtccccct | 1440 |
| acatcgtgac ctgggaagcc ttggcttttg accccctcc ctgggtcaag ccctttgtac | 1500 |
| accctaagcc tccgcctcct cttcctccat ccgccccgtc tctccccctt gaacctcctc | 1560 |
| gttcgacccc gcctcgatcc tccctttatc cagccctcac tccttctcta ggcgccggaa | 1620 |
| ttccgatctg atcaagagac aggatgagga tcgtttcgca tgattgaaca agatggattg | 1680 |
| cacgcaggtt ctccggccgc ttgggtgagg aggctattcg gctatgactg ggcacaacag | 1740 |
| acaatcggct gctctgatgc cgccgtgttc cggctgtcag cgcaggggcg cccggttctt | 1800 |
| tttgtcaaga ccgacctgtc cggtgccctg aatgaactgc aggacgaggc agcgcggcta | 1860 |
| tcgtggctgg ccacgacggg cgttccttgc gcagctgtgc tcgacgttgt cactgaagcg | 1920 |

```
ggaagggact ggctgctatt gggcgaagtg ccggggcagg atctcctgtc atctcacctt   1980
gctcctgccg agaaagtatc catcatggct gatgcaatgc ggcggctgca tacgcttgat   2040
ccggctacct gcccattcga ccaccaagcg aaacatcgca tcgagcgagc acgtactcgg   2100
atggaagccg gtcttgtcga tcaggatgat ctggacgaag agcatcaggg gctcgcgcca   2160
gccgaactgt tcgccaggct caaggcgcgc atgcccgacg cgaggatctc gtcgtgacc    2220 catgcgatg cctgcttgcc gaatatcatg gtggaaaatg gccgcttttc tggattcatc    2280
gactgtggcc ggctgggtgt ggcggaccgc tatcaggaca tagcgttggc tacccgtgat   2340
attgctgaag agcttggcgg cgaatgggct gaccgcttcc tcgtgcttta cggtatcgcc   2400
gctcccgatt cgcagcgcat cgccttctat cgccttcttg acgagttctt ctgagcggga   2460
ctctggggtt cgaaatgacc gaccaagcga cgcccaacct gccatcacga gatttcgatt   2520
ccaccgccgc cttctatgaa aggttgggct tcggaatcgt tttccgggac gccggctgga   2580
tgatcctcca gcgcggggat ctcatgctgg agttcttcgc ccaccccggg ctcgatcccc   2640
tcgcgagttg gttcagctgc tgcctgaggc tggacgacct cgcggagttc taccggcagt   2700
gcaaatccgt cggcatccag gaaaccagca gcggctatcc gcgcatccat gcccccgaac   2760
tgcaggagtg gggaggcacg atggccgctt ggtcgaggc ggatccggcc attagccata    2820
ttattcattg gttatatagc ataaatcaat attggctatt ggccattgca tacgttgtat   2880
ccatatcata atatgtacat ttatattggc tcatgtccaa cattaccgcc atgttgacat   2940
tgattattga ctagttatta atagtaatca attacgggt cattagttca tagcccatat    3000
atggagttcc gcgttacata acttacggta aatggcccgc ctggctgacc gcccaacgac   3060
ccccgcccat tgacgtcaat aatgacgtat gttcccatag taacgccaat agggactttc   3120
cattgacgtc aatgggtgga gtatttacgg taaactgccc acttggcagt acatcaagtg   3180
tatcatatgc caagtacgcc ccctattgac gtcaatgacg gtaaatggcc cgcctggcat   3240
tatgcccagt acatgacctt atgggacttt cctacttggc agtacatcta cgtattagtc   3300
atcgctatta ccatggtgat gcggttttgg cagtacatca atgggcgtgg atagcggttt   3360
gactcacggg gatttccaag tctccacccc attgacgtca atgggagttt gttttggcac   3420
caaaatcaac gggactttcc aaaatgtcgt aacaactccg ccccattgac gcaaatgggc   3480
ggtaggcatg tacggtggga ggtctatata agcagagctc gtttagtgaa ccgtcagatc   3540
gcctggagac gccatccacg ctgttttgac ctccatagaa gacaccggga ccgatccagc   3600
ctccgcggcc ccaagcttgt tatcacaagt ttgtacaaaa aagcaggctt cgaaggagat   3660
agaaccaatt ctctaaggaa atacttaacg tcgactggat ccggtaccga attcggcgcc   3720
gccaccatga tgtcctttgt ctctctgctc ctggtaggca tcctattcca tgccacccag   3780
gccgacatcc agctgaccca gagcccaagc agcctgagcg ccagcgtggg tgacagagtg   3840
accatcacct gtaaggccag tcaggatgtg ggtacttctg tagcctggta ccagcagaag   3900
ccaggtaagg ctccaaagct gctgatctac tggacatcca cccggcacac tggtgtgcca   3960
agcagattca gcggtagcgg tagcggtacc gacttcacct tcaccatcag cagcctccag   4020
ccagaggaca tcgccaccta ctactgccag caatatagcc tctatcggtc gttcggccaa   4080
gggaccaagg tggaaatcaa acgaactgtg ctgcaccat ctgtcttcat cttcccgcca    4140
tctgatgagc agttgaaatc tggaactgcc tctgttgtgt gcctgctgaa taacttctat   4200
cccagagagg ccaaagtaca gtggaaggtg ataacgccc tccaatcggg taactcccag    4260
gagagtgtca cagagcagga cagcaaggac agcacctaca gcctcagcag caccctgacg   4320
```

```
ctgagcaaag cagactacga gaaacacaaa gtctacgcct gcgaagtcac ccatcagggc    4380
ctgagctcgc ccgtcacaaa gagcttcaac aggggagagt gttagatctc gagatatcta    4440
gacccagctt tcttgtacaa agtggtgata acatcgataa aataaaagat tttatttagt    4500
ctccagaaaa aggggggaat gaaagacccc acctgtaggt ttggcaagct agcttaagta    4560
acgccatttt gcaaggcatg gaaaaataca taactgagaa tagagaagtt cagatcaagg    4620
tcaggaacag atggaacagc tgaatatggg ccaaacagga tatctgtggt aagcagttcc    4680
tgccccggct cagggccaag aacagatgga acagctgaat atgggccaaa caggatatct    4740
gtggtaagca gttcctgccc cggctcaggg ccaagaacag atggtcccca gatgcggtcc    4800
agccctcagc agtttctaga gaaccatcag atgtttccag ggtgccccaa ggacctgaaa    4860
tgaccctgtg ccttatttga actaaccaat cagttcgctt ctcgcttctg ttcgcgcgct    4920
tctgctcccc gagctcaata aaagagccca cacccctca ctcggggcgc cagtcctccg    4980
attgactgag tcgcccgggt acccgtgtat ccaataaacc ctcttgcagt tgcatccgac    5040
ttgtggtctc gctgttcctt ggagggtct cctctgagtg attgactacc cgtcagcggg    5100 ggtcttcat ttgggggctc gtccgggatc gggagacccc tgcccaggga ccaccgaccc    5160
accaccggga ggtaagctgg ctgcctcgcg cgtttcggtg atgacggtga aaacctctga    5220
cacatgcagc tcccggagac ggtcacagct tgtctgtaag cggatgccgg gagcagacaa    5280
gcccgtcagg gcgcgtcagc gggtgttggc gggtgtcggg gcgcagccat gacccagtca    5340
cgtagcgata gcggagtgta tactggctta actatgcggc atcagagcag attgtactga    5400
gagtgcacca tatgcggtgt gaaataccgc acagatgcgt aaggagaaaa taccgcatca    5460
ggcgctcttc cgcttcctcg ctcactgact cgctgcgctc ggtcgttcgg ctgcggcgag    5520
cggtatcagc tcactcaaag gcggtaatac ggttatccac agaatcaggg gataacgcag    5580
gaaagaacat gtgagcaaaa ggccagcaaa aggccaggaa ccgtaaaaag gccgcgttgc    5640
tggcgttttt ccataggctc cgcccccctg acgagcatca caaaaatcga cgctcaagtc    5700
agaggtggcg aaacccgaca ggactataaa gataccaggc gtttccccct ggaagctccc    5760
tcgtgcgctc tcctgttccg accctgccgc ttaccggata cctgtccgcc tttctccctt    5820
cgggaagcgt ggcgctttct catagctcac gctgtaggta tctcagttcg gtgtaggtcg    5880
ttcgctccaa gctgggctgt gtgcacgaac cccccgttca gcccgaccgc tgcgccttat    5940
ccggtaacta tcgtcttgag tccaacccgg taagacacga cttatcgcca ctggcagcag    6000
ccactggtaa caggattagc agagcgaggt atgtaggcgg tgctacagag ttcttgaagt    6060
ggtggcctaa ctacggctac actagaagga cagtatttgg tatctgcgct ctgctgaagc    6120
cagttacctt cggaaaaaga gttggtagct cttgatccgg caaacaaacc accgctggta    6180
gcggtggttt ttttgtttgc aagcagcaga ttacgcgcag aaaaaaagga tctcaagaag    6240
atcctttgat cttttctacg gggtctgacg ctcagtggaa cgaaaactca cgttaaggga    6300
ttttggtcat gagattatca aaaaggatct cacctagat cctttttaaat taaaaatgaa    6360 gttttaaatc aatctaaagt atatatgagt aaacttggtc tgacagttac caatgcttaa    6420
tcagtgaggc acctatctca gcgatctgtc tatttcgttc atccatagtt gcctgactcc    6480
ccgtcgtgta gataactacg atacgggagg gcttaccatc tggccccagt gctgcaatga    6540
taccgcgaga cccacgctca ccggctccag atttatcagc aataaaccag ccagccggaa    6600
gggccgagcg cagaagtggt cctgcaactt tatccgcctc catccagtct attaattgtt    6660
gccgggaagc tagagtaagt agttcgccag ttaatagttt gcgcaacgtt gttgccattg    6720
```

```
ctgcaggcat cgtggtgtca cgctcgtcgt ttggtatggc ttcattcagc tccggttccc    6780
aacgatcaag gcgagttaca tgatccccca tgttgtgcaa aaaagcggtt agctccttcg    6840
gtcctccgat cgttgtcaga agtaagttgg ccgcagtgtt atcactcatg gttatggcag    6900
cactgcataa ttctcttact gtcatgccat ccgtaagatg cttttctgtg actggtgagt    6960
actcaaccaa gtcattctga gaatagtgta tgcggcgacc gagttgctct tgcccggcgt    7020
caacacggga taataccgcg ccacatagca gaactttaaa agtgctcatc attggaaaac    7080
gttcttcggg gcgaaaactc tcaaggatct taccgctgtt gagatccagt tcgatgtaac    7140
ccactcgtgc acccaactga tcttcagcat cttttacttt caccagcgtt tctgggtgag    7200
caaaaacagg aaggcaaaat gccgcaaaaa agggaataag ggcgacacgg aaatgttgaa    7260
tactcatact cttcctttt caatattatt gaagcattta tcagggttat tgtctcatga    7320
gcggatacat atttgaatgt atttagaaaa ataaacaaat aggggttccg cgcacatttc    7380
cccgaaaagt gccacctgac gtctaagaaa ccattattat catgacatta acctataaaa    7440
ataggcgtat cacgaggccc tttcgtcttc aa                                  7472
```